(12) United States Patent
Bennani et al.

(10) Patent No.: US 8,163,732 B2
(45) Date of Patent: Apr. 24, 2012

(54) TRICYCLIC HETEROARYL COMPOUNDS USEFUL AS INHIBITORS OF JANUS KINASE

(75) Inventors: Youssef Bennani, Boston, MA (US); Tiansheng Wang, Concord, MA (US); Francesco Salituro, Marlboro, MA (US); John Duffy, Northborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/434,154

(22) Filed: May 1, 2009

(65) Prior Publication Data

US 2010/0081645 A1    Apr. 1, 2010

Related U.S. Application Data

(63) Continuation of application No. PCT/US2007/083134, filed on Oct. 31, 2007.

(60) Provisional application No. 60/855,862, filed on Nov. 1, 2006, provisional application No. 60/738,646, filed on Nov. 21, 2005, provisional application No. 60/737,008, filed on Nov. 15, 2005.

(51) Int. Cl.
*A61K 31/55* (2006.01)
*C07D 471/12* (2006.01)

(52) U.S. Cl. .................... 514/213.01; 540/478
(58) Field of Classification Search .................... None
See application file for complete search history.

(56) References Cited

FOREIGN PATENT DOCUMENTS
WO    2006/096270 A    9/2006

OTHER PUBLICATIONS

Thompson. Drug News Perspectives, 2005, 18(5), 305-310.*
Yang. Journal of Molecular Structure, 2002, 618, 191-200.*
International Search Report from corresponding International Application No. PCT/US2007/083134 filed Jul. 7, 2008.

* cited by examiner

*Primary Examiner* — Noble Jarrell
(74) *Attorney, Agent, or Firm* — Lisa A. Dixon; Susan C. Kelly

(57) ABSTRACT

The present invention relates to compounds useful as inhibitors of protein kinases, particularly of JAK family kinases. The invention also provides pharmaceutically acceptable compositions comprising said compounds and methods of using the compositions in the treatment of various disease, conditions, or disorders.

16 Claims, No Drawings

TRICYCLIC HETEROARYL COMPOUNDS USEFUL AS INHIBITORS OF JANUS KINASE

CROSS-REFERENCE TO RELATED APPLICATIONS

The present application is a continuation application of International Patent Application No. PCT/US2007/83134 filed Oct. 31, 2007, which in turn claims the benefit, under 35 U.S.C. §111(a), of U.S. Provisional Application No. 60/737,008, filed on 15 Nov. 2005, and U.S. Provisional Application No. 60/738,646, filed on 21 Nov. 2005, and U.S. Provisional Application No. 60/855,862, filed on 1 Nov. 2006, the entire contents of each of the above applications is incorporated herein by reference.

TECHNICAL FIELD OF THE INVENTION

The present invention relates to compounds useful as inhibitors of Janus kinases (JAK). The invention also provides pharmaceutically acceptable compositions that include the compounds of the invention and methods of using these compositions in the treatment of various disorders.

BACKGROUND OF THE INVENTION

The Janus kinases (JAK) are a family of tyrosine kinases that play a critical role in cytokine signaling. The family consists of JAK-1, JAK-2, JAK-3 and TYK-2, and the downstream substrates of this family of kinases include the signal transducer and activator of transcription (STAT) proteins. JAK/STAT signaling has been implicated in the mediation of many abnormal immune responses, such as allergies and asthma; autoimmune diseases, such as transplant rejection, rheumatoid arthritis, amyotrophic lateral sclerosis and multiple sclerosis; as well as in solid and hematologic malignancies, such as leukemias and lymphomas. JAK-2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome, and systematic mast cell disease.

Therefore, there is a need to develop compounds that bind to the JAK family kinases and thereby moderate JAK/STAT signaling.

SUMMARY OF THE INVENTION

It has been found that compounds of the present invention, and pharmaceutically acceptable compositions thereof, are effective as inhibitors of protein kinases, particularly the JAK family kinases. Accordingly, the invention features compounds having the formula:

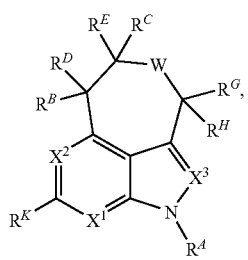

(formula I)

or a pharmaceutically acceptable salt or prodrug thereof, where $R^A$, $R^B$, $R^C$, $R^D$, $R^E$, $R^G$, $R^H$, $R^K$, W, $X^1$, $X^2$, and $X^3$ are as defined below.

The invention also provides pharmaceutical compositions that include a compound of the invention and a pharmaceutically acceptable carrier, adjuvant, or vehicle. In addition, the invention provides methods of treating or lessening the severity of a disease, condition, or disorder in a patient selected from: a proliferative disorder, a cardiac disorder, a neurodegenerative disorder, an autoimmune disorder, a condition associated with organ transplant, an inflammatory disorder, an immunologically mediated disorder, or a bone disorder that includes the step of administering to the patient a therapeutically effective dose of a compound of the invention or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with a non-hydrogen radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent hydrocarbon group derived from a straight or branched chain saturated hydrocarbon by the removal of two hydrogen atoms, and is exemplified by methylene, ethylene, isopropylene and the like. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" means alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

In some embodiments, an aryl (including aralkyl, aralkoxy, aryloxyalkyl, and the like) or heteroaryl (including heteroaralkyl, heteroarylalkoxy, and the like) group may contain one or more substituents. Suitable substituents on the unsaturated carbon atom of an aryl or heteroaryl group include: halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1-2}$(Ph), optionally substituted with R°; —CH=CH(Ph), optionally substituted with R°; —NO₂; —CN; —N(R°)₂; —NR°C(O)R°; —NR°C(S)R°; —NR°C(O)N(R°)₂; —NR°C(S)N(R°)₂; —NR°C(O)OR°; —NR°NR°C(O)R°; —NR°NR°C(O)N(R°)₂; —NR°NR°C(O)OR°; —C(O)C(O)R°; —C(O)CH₂C(O)R°; —C(O)OR°; —C(O)R°; —C(S)R°; —C(O)N(R°)₂; —C(S)N(R°)₂; —B(OR°)₂; —OC(O)N(R°)₂; —OC(O)R°; —C(O)N(OR°)R°; —C(NOR°)R°; —S(O)₂R°; —S(O)₃R°; —S(O)₂N(R°)₂; —S(O)R°; —NR°S(O)₂N(R°)₂; —NR°S(O)₂R°; —N(OR°)R°; —C(=NH)—N(R°)₂; —(CH₂)₀₋₂NHC(O)R°; -L-R°; -L-N(R°)₂; -L-SR°; -L-OR°; -L-(C₃₋₁₀ cycloaliphatic), -L-(C₆₋₁₀ aryl), -L-(5-10 membered heteroaryl), -L-(5-10 membered heterocyclyl), oxo, C₁₋₄ haloalkoxy, C₁₋₄ haloalkyl, -L-NO₂, -L-CN, -L-OH, -L-CF₃; or two substituents, on the same carbon or on different carbons, together with the carbon or intervening carbons to which they are bound, form a 5-7 membered saturated, unsaturated, or partially saturated ring, wherein L is a C₁₋₆ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)₂NH—, —S(O)₂NR°—, —NHS(O)₂—, —NR°S(O)₂—, —NHC(O)NH—, —NR°C(O)NH—, —NHC(O)NR°—, —NR°C(O)NR°, —OC(O)NH—, —OC(O)NR°—, —NHS(O)₂NH—, —NR°S(O)₂NH—, —NHS(O)₂NR°—, —NR°S(O)₂NR°—, —S(O)—, or —S(O)₂—, and wherein each occurrence of R° is independently selected from hydrogen, optionally substituted C₁₋₆ aliphatic, an unsubstituted 5- to 6-membered heteroaryl or heterocyclic ring, phenyl, or —CH₂(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur. Optional substituents on the aliphatic group of R° are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —O(haloC₁₋₄ aliphatic), or haloC₁₋₄ aliphatic, wherein each of the foregoing C₁₋₄ aliphatic groups of R° is unsubstituted.

In some embodiments, an aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHC(O)O(alkyl), =NNHS(O)₂(alkyl), or =NR*, where each R* is independently selected from hydrogen or an optionally substituted C₁₋₆ aliphatic. Optional substituents on the aliphatic group of R* are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —O(halo-C₁₋₄ aliphatic), and halo(C₁₋₄ aliphatic), where each of the foregoing C₁₋₄ aliphatic groups of R* is unsubstituted.

In some embodiments, optional substituents on the nitrogen of a non-aromatic heterocyclic ring include —R⁺, —N(R⁺)₂, —C(O)R⁺, —C(O)OR⁺, —C(O)C(O)R⁺, —C(O)CH₂C(O)R⁺, —S(O)₂R⁺, —S(O)₂N(R⁺)₂, —C(=S)N(R⁺)₂, —C(=NH)—N(R⁺)₂, or —NR⁺S(O)₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of R⁺, on the same substituent or different substituents, taken together with the atom(s) to which each R⁺ group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R⁺ are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —C(O)OH, —C(O)O(C₁₋₄ aliphatic), —O(halo C₁₋₄ aliphatic), or halo(C₁₋₄ aliphatic), wherein each of the foregoing C₁₋₄ aliphatic groups of R⁺ is unsubstituted.

As detailed above, in some embodiments, two independent occurrences of R° (or R⁺, or any other variable similarly defined herein), may be taken together with the atom(s) to which each variable is bound to form a 5-8-membered heterocyclyl, aryl, or heteroaryl ring or a 3-8-membered cycloalkyl ring. Exemplary rings that are formed when two independent occurrences of R° (or R⁺, or any other variable similarly defined herein) are taken together with the atom(s) to which each variable is bound include, but are not limited to the following: a) two independent occurrences of R° (or R⁺, or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

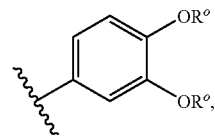

these two occurrences of R° are taken together with the oxygen atoms to which they are bound to form a fused 6-membered oxygen containing ring:

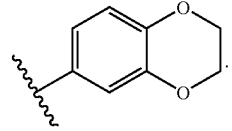

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —C(O)O—, —OC(O)—, —C(O)CO—, —C(O)—, —C(O)NR—, —C(=N—CN)—, —NRCO—, —NRC(O)O—, —S(O)$_2$NR—, —NRS(O)$_2$—, —NRC(O)NR—, —OC(O)NR—, —NRS(O)$_2$NR—, —S(O)—, or —S(O)$_2$—, wherein R is defined herein. Unless otherwise specified, the optional replacements form a chemically stable compound. Optional interruptions can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below), represents substitution of the substituent at any substitutable position in any of the rings within the multiple ring system. For example, FIG. a represents possible substitution in any of the positions shown in FIG. b.

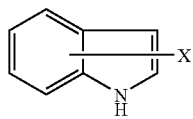

Figure a

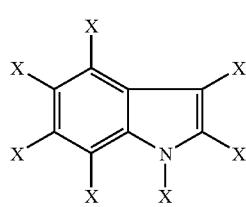

Figure b

This also applies to multiple ring systems fused to optional ring systems (which would be represented by dotted lines). For example, in FIG. c, X is an optional substituent both for ring A and ring B.

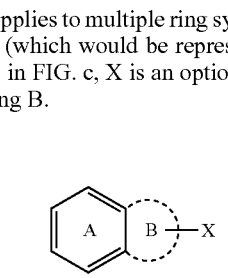

Figure c

If, however, two rings in a multiple ring system each have different substituents drawn from the center of each ring, then, unless otherwise specified, each substituent only represents substitution on the ring to which it is attached. For example, in FIG. d, Y is an optionally substituent for ring A only, and X is an optional substituent for ring B only.

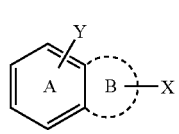

Figure d

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound which is transformed in vivo into a compound of the invention. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

Description of Compounds of the Invention

In one aspect, the present invention features compounds having the formula:

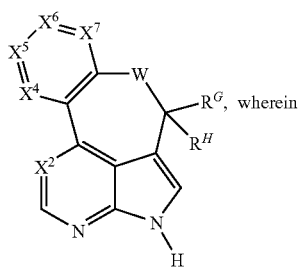

(I-a)

W is —N($R^F$)-, —C(X)N($R^F$)- or —N($R^F$)C(X)-;
X is O, S, [hydrogen, hydrogen] or [hydrogen, R];
$X^2$ is N or C—$R^{X2}$, wherein $R^{X2}$ is hydrogen, halogen, —CN, —NO$_2$, —OR$^{X2B}$, —OC(O)R$^{X2B}$, —OC(O)OR$^{X2B}$, —OC(O)NR$^{X2A}$R$^{X2B}$, —OC(S)R$^{X2B}$, —SR$^{X2B}$, —SC(O)R$^{X2B}$, —SC(S)R$^{X2B}$, —C(O)OR$^{X2B}$, —C(O)NR$^{X2A}$R$^{X2B}$, —C(S)NR$^{X2A}$R$^{X2B}$, —NR$^{X2A}$R$^{X2B}$, —S(O)R$^{X2B}$, —S(O)$_2$R$^{X2B}$, —S(O)$_2$NR$^{X2A}$R$^{X2B}$, C$_{1-4}$haloaliphatic, optionally substituted C$_{3-8}$ cycloaliphatic, C$_{1-6}$ aliphatic;
$X^4$ is N or C—$R^{B4}$, $X^5$ is N or C—$R^{B5}$, $X^6$ is N or C—$R^{B6}$, and $X^7$ is N or C—$R^{B7}$, where optionally up to two of $X^4$, $X^5$, $X^6$, and $X^7$ are N and each of $R^{B4}$, $R^{B5}$, $R^{B6}$, and $R^{B7}$ is, independently, hydrogen, halogen, —CN, —NO$_2$, —OR, —OC(O)R, —OC(O)OR, —OC(O)NRR, —OC(S)R, —SR, —SC(O)R, —SC(S)R, —C(O)OR, —C(O)NRR, —C(S)NRR, —NRR, —S(O)R, —S(O)$_2$R, —S(O)$_2$NRR, optionally substituted C$_{1-4}$ haloaliphatic, C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl;
each of $R^F$ and $R^G$ is, independently, hydrogen, optionally substituted C$_{1-6}$ aliphatic, C$_{1-4}$ haloaliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, 8- to 12-membered bicyclic heteroaryl, or when W is N($R^F$), $R^F$ and $R^G$ and the intervening atoms together optionally form a N=C bond;
$R^H$ is hydrogen, optionally substituted C$_{1-6}$ aliphatic, C$_{1-4}$haloaliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl;
$R^{X2A}$ is hydrogen, optionally substituted C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, 8- to 12-membered bicyclic heteroaryl, —C(O)R, —C(O)NRR, —C(O)OR, —S(O)R, —S(O)$_2$R, or —S(O)$_2$NRR;
each of R, R, and $R^{X2B}$ is, independently, hydrogen, optionally substituted C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl;
each of said heterocyclyl and heteroaryl rings contains one to four heteroatoms independently selected from oxygen, sulfur, or nitrogen;
the optional substituents on one or more carbon atoms of each of said aryl and heteroaryl groups are: halogen; —R°; —OR°; —SR°; 1,2-methylenedioxy; 1,2-ethylenedioxy; phenyl optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(=NOR°)R°; —S(O)$_2$R°; —S(O)$_2$OR°; —S(O)$_2$N(R°)$_2$; —S(O)R°; —NR°S(O)$_2$N(R°)$_2$; —NR°S(O)$_2$R°; —N(OR°)R°; —C(=NH)—N(R°)$_2$; or —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)C(O)—, —C(O)—, —C(O)NH—, —C(O)NR°—, —C(=N—CN)—, —NHC(O)—, —NR°C(O)—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from hydrogen, optionally substituted C$_{1-6}$ aliphatic, an unsubstituted 5- to 6-membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur, wherein optional substituents on the aliphatic group of R° are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, C(O)O(C$_{1-4}$ aliphatic), O(haloC$_{1-4}$ aliphatic), or haloC$_{1-4}$ aliphatic, wherein each of the C$_{1-4}$ aliphatic groups of R° is unsubstituted; and the optional substituents on one or more carbon atoms of each of said aliphatic, haloaliphatic, cyclo aliphatic, and heterocyclyl groups are as defined for said aryl and heteroaryl groups and additionally comprise: =O, =S, =NNHR*, =NN(R*)$_2$, =NNHC(O)R*, =NNHC(O)O(alkyl), =NNHS(O)$_2$(alkyl), or =NR*, wherein each R* is independently selected from hydrogen or an optionally substituted C$_{1-6}$ aliphatic, and where optional substituents on said aliphatic group of R* are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo-C$_{1-4}$ aliphatic), and halo(C$_{1-4}$ aliphatic), wherein each of the foregoing C$_{1-4}$ aliphatic groups of R* is unsubstituted.

In one embodiment, a compound of formula I-a has the formula:

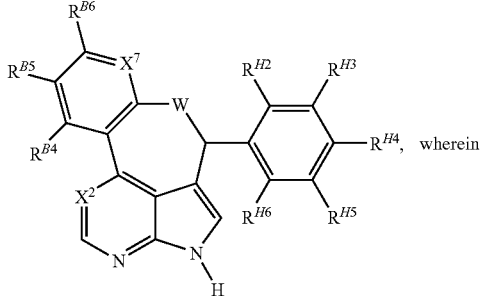

(I-b)

each of $R^{H2}$, $R^{H3}$, $R^{H4}$, $R^{H5}$, and $R^{H6}$ is, independently, hydrogen, halogen, —CN, —NO$_2$, —OR, —B(OR)$_2$, —OC(O)R, —OC(O)OR, —OC(S)R, —SR, —SC(O)R, —SC(S)R, —C(O)OR, —C(O)NRR, —C(S)NRR, —NRR, —S(O)R, —S(O)$_2$R, —S(O)$_2$NRR, optionally substituted C$_{1-4}$ haloaliphatic, C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl. In a further embodiment, $R^{H4}$ is —OR, —B(OR)$_2$, —OC(O)R, —OC(O)OR, or —OC(S)R; each of $R^{B4}$, $R^{B5}$, and $R^{B6}$ is hydrogen; and X$^2$ is N or C—H. Desirably, $R^{H4}$ is —OH. In another further embodiment, one or both of $R^{H3}$ and $R^{H5}$ is a halogen. In yet another example, both of $R^{H3}$ and $R^{H5}$ is a halogen, such as, for example, fluorine.

In another embodiment of a compound of formula I-a, W is —N(R$^F$)-. In another embodiment, at least one of R$^G$ or R$^H$ is not hydrogen. In a further embodiment, R$^H$ is an optionally substituted C$_{1-6}$ aliphatic, C$_{3-8}$ cycloaliphatic, C$_{6-10}$ aryl, 3- to 8-membered monocyclic heterocyclyl, or 5- to 8-membered monocyclic heteroaryl. Further still, R$^H$ is an optionally substituted C$_{6-10}$ aryl or 5- to 8-membered monocyclic heteroaryl.

In yet another embodiment of a compound of formula I-a, or a pharmaceutically acceptable salt thereof, the compound has the formula:

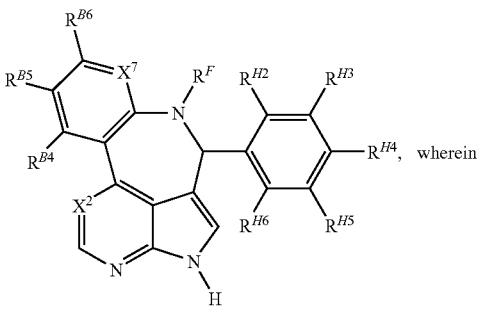

(II-a)

each of $R^{H2}$, $R^{H3}$, $R^{H4}$, $R^{H5}$, and $R^{H6}$ is, independently, hydrogen, halogen, —CN, —NO$_2$, —OR, —B(OR)$_2$, —OC(O)R, —OC(O)OR, —OC(S)R, —SR, —SC(O)R, —SC(S)R, —C(O)OR, —C(O)NRR, —C(S)NRR, —NRR, —S(O)R, —S(O)$_2$R, —S(O)$_2$NRR, optionally substituted C$_{1-4}$haloaliphatic, C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl.

In a further embodiment of compounds of formula II-a, $R^{H4}$ is —OR, —B(OR)$_2$, —OC(O)R, —OC(O)OR, or —OC(S)R; each of $R^{B4}$, $R^{B5}$, and $R^{B6}$ is hydrogen; and X$^2$ is N or C—H. Further still, in another embodiment, $R^{H4}$ is —OH.

In another embodiment, compounds of formula I-a have the formula:

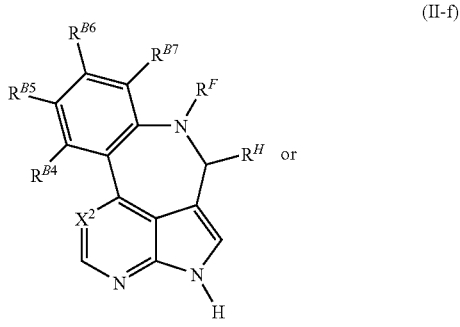

(II-f)

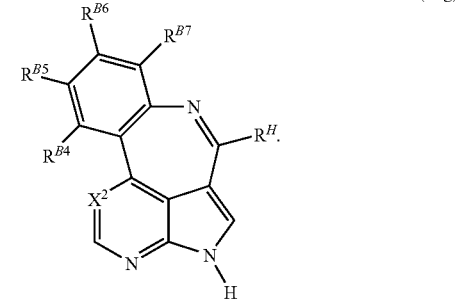

(II-g)

In a further embodiment of compounds of formula II-f or II-g, each of $R^{B4}$, $R^{B5}$, $R^{B6}$, and $R^{B7}$ is hydrogen.

In another embodiment for any of the compounds of the invention, each of $R^{B4}$, $R^{B5}$, and $R^{B6}$ is hydrogen; X$^7$ is N or C—H; X$^2$ is N or C—H; and each of $R^{H2}$, $R^{H3}$, $R^{H5}$, and $R^{H6}$ is, independently, hydrogen, halogen, —CN, —NO$_2$, —OR, —B(OR)$_2$, —OC(O)R, —OC(O)OR, —C(O)OR, —C(O)NRR, —C(S)NRR, —NRR, —S(O)$_2$R, —S(O)$_2$NRR, optionally substituted C$_{1-4}$haloaliphatic, C$_{1-6}$ aliphatic, C$_{3-8}$ cycloaliphatic, wherein each of R and R is, independently, hydrogen or optionally substituted C$_{1-6}$ aliphatic.

In another aspect, the invention features a compound selected from the group of compounds listed in Table 1.

JAK-2 and JAK-3 inhibition assays were performed as described elsewhere herein. Table 1 presents enzyme inhibition data for certain exemplary compounds, where "A" represents a K$_i$ of 0.25 μM or less, "B" represents a K$_i$ of greater than 0.25 μM and less than or equal to 2.5 μM, and "C" represents a K$_i$ value of greater than 2.5 μM.

TABLE 1
| Structure | JAK-2 | JAK-3 |
|---|---|---|
| 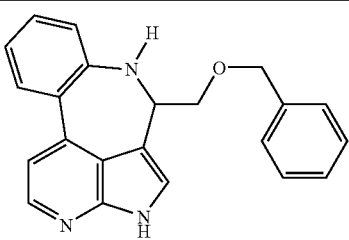<br>1 | C | B |
| 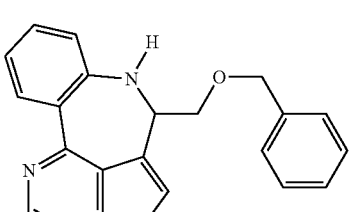<br>2 | C | C |
| 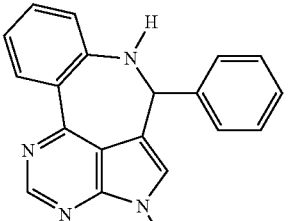<br>3 | C | B |
| 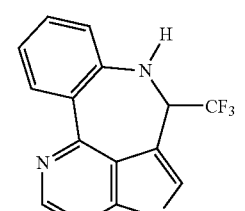<br>4 | C | C |
| 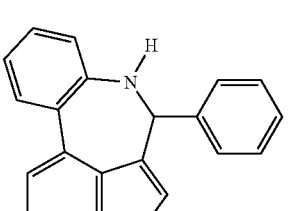<br>5 | B | B |
TABLE 1-continued
| Structure | JAK-2 | JAK-3 |
|---|---|---|
| 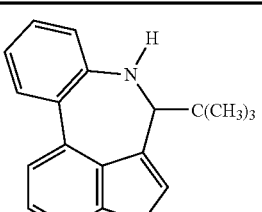<br>6 | B | B |
| 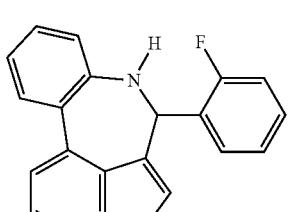<br>7 | A | B |
| 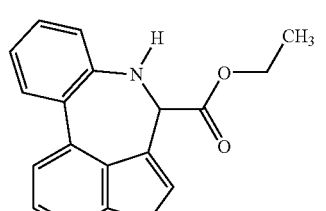<br>8 | B | B |
| 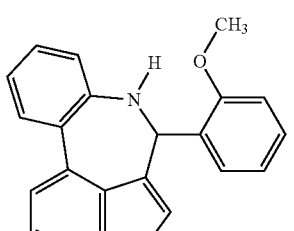<br>9 | B | B |
| 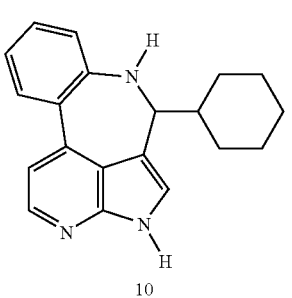<br>10 | C | C |

TABLE 1-continued
| Structure | JAK-2 | JAK-3 |
|---|---|---|
| 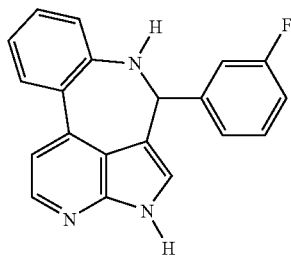 11 | A | B |
| 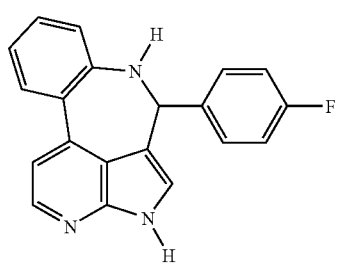 12 | B | B |
| 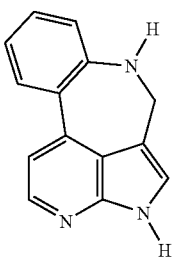 13 | B | B |
| 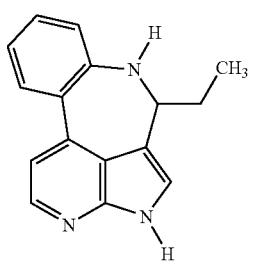 14 | B | B |
| 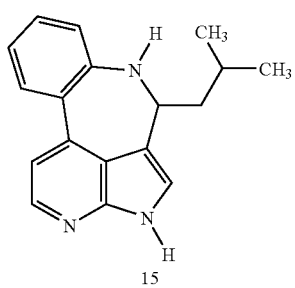 15 | C | C |
TABLE 1-continued
| Structure | JAK-2 | JAK-3 |
|---|---|---|
| 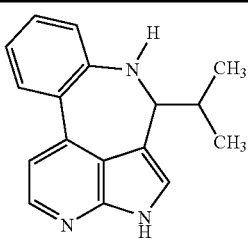 16 | B | C |
| 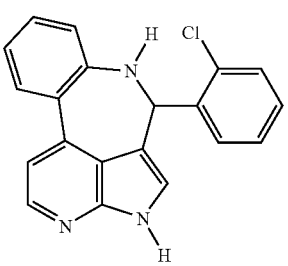 17 | B | B |
| 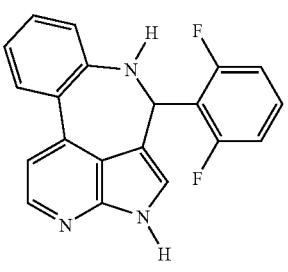 18 | A | B |
| 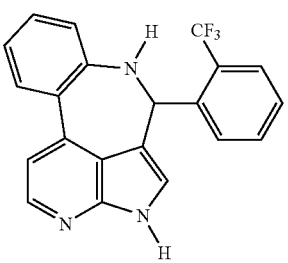 19 | B | B |
| 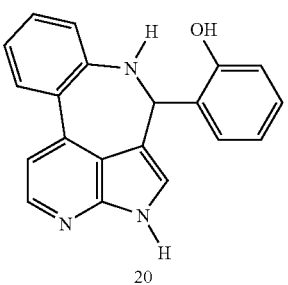 20 | B | B |

TABLE 1-continued
| Structure | JAK-2 | JAK-3 |
|---|---|---|
| 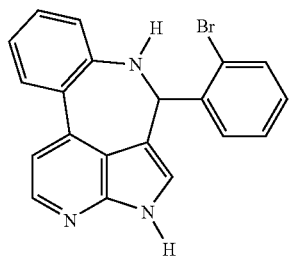 21 | B | B |
| 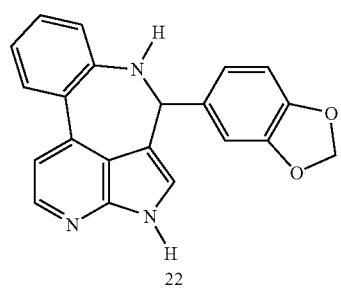 22 | A | B |
| 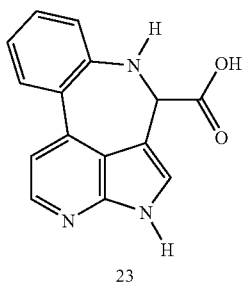 23 | B | B |
| 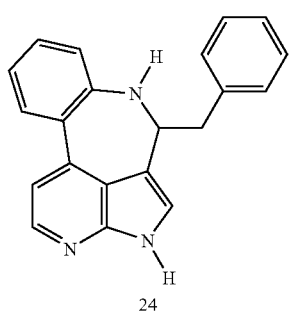 24 | B | B |
| 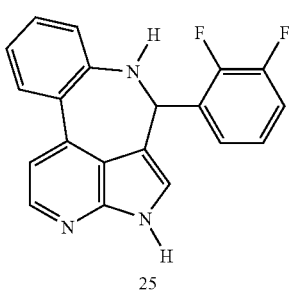 25 | A | B |
TABLE 1-continued
| Structure | JAK-2 | JAK-3 |
|---|---|---|
| 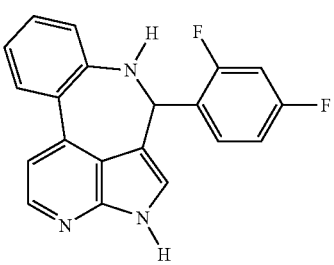 26 | A | B |
| 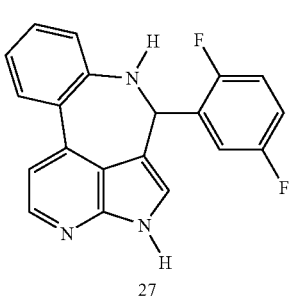 27 | A | A |
| 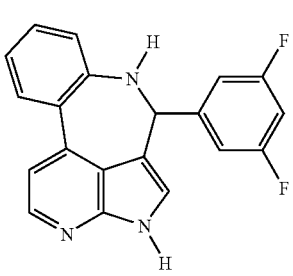 28 | B | B |
| 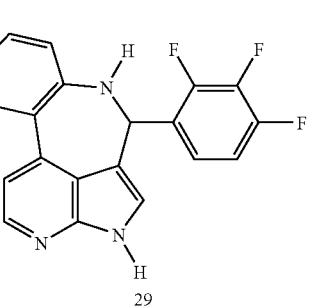 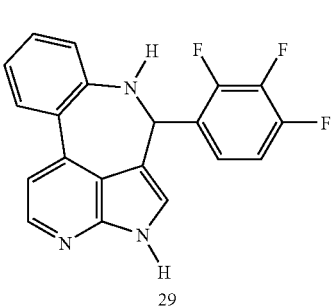 29 | B | B |
| 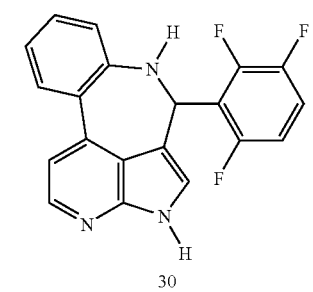 30 | A | A |

TABLE 1-continued
| Structure | JAK-2 | JAK-3 |
|---|---|---|
| 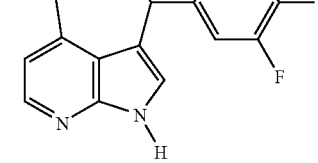 31 | A | B |
| 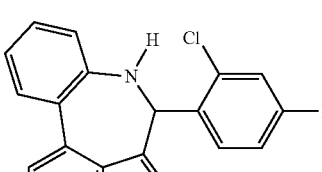 32 | B | C |
| 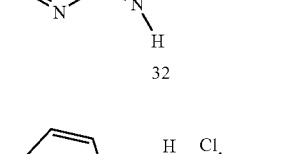 33 | B | B |
| 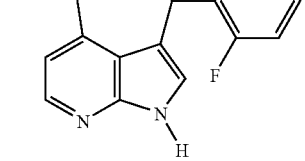 34 | B | B |
| 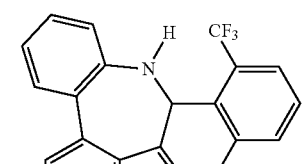 35 | B | B |
| 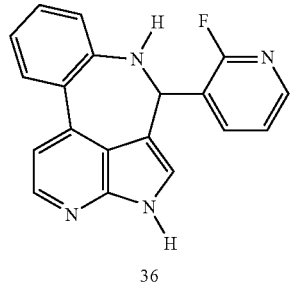 36 | B | B |
| 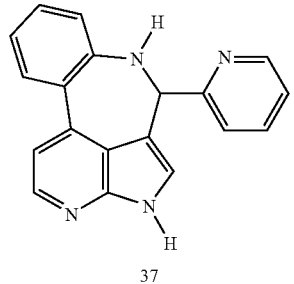 37 | C | C |
| 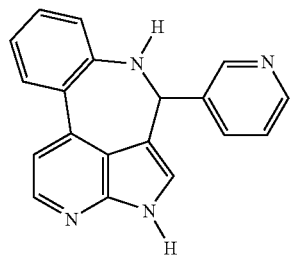 38 | B | B |
| 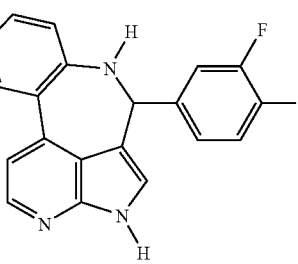 39 | A | B |
| 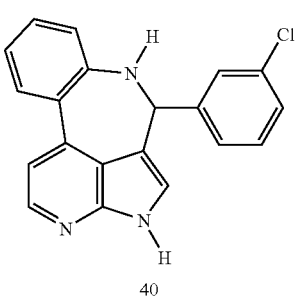 40 | B | B |

TABLE 1-continued
| Structure | JAK-2 | JAK-3 |
|---|---|---|
| 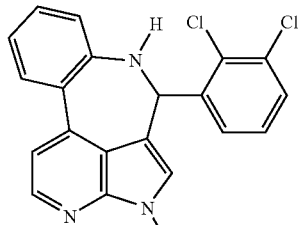 41 | B | C |
| 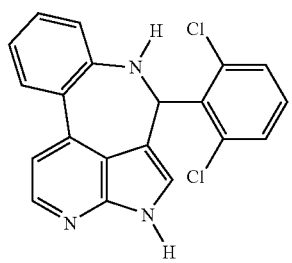 42 | B | B |
| 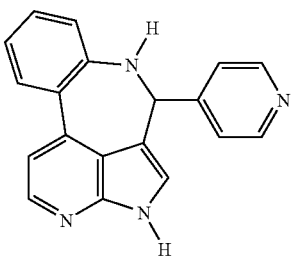 43 | B | C |
| 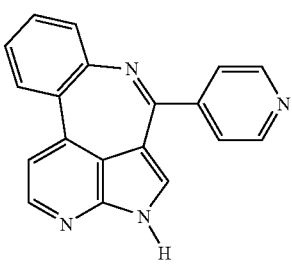 44 | A | B |
| 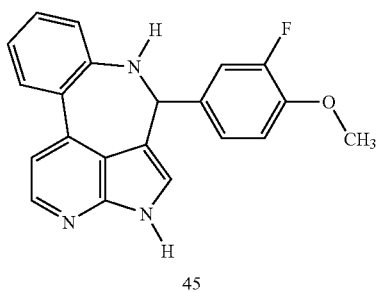 45 | A | B |
TABLE 1-continued
| Structure | JAK-2 | JAK-3 |
|---|---|---|
| 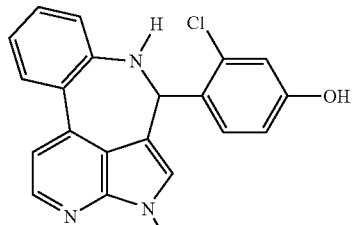 46 | A | A |
| 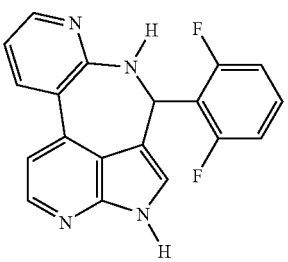 47 | B | B |
| 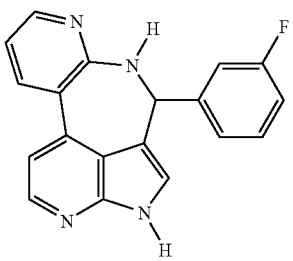 48 | B | B |
| 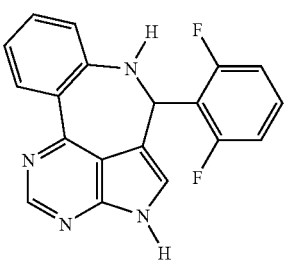 49 | A | B |
| 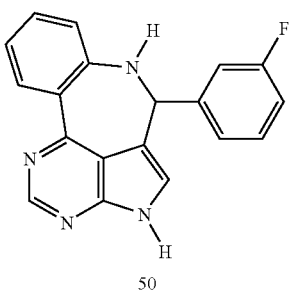 50 | B | C |

TABLE 1-continued
| Structure | JAK-2 | JAK-3 |
|---|---|---|
| 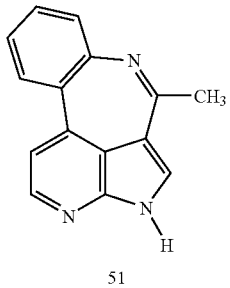 51 | B | B |
| 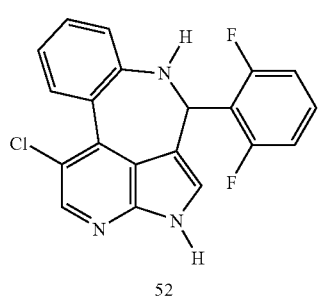 52 | B | B |
| 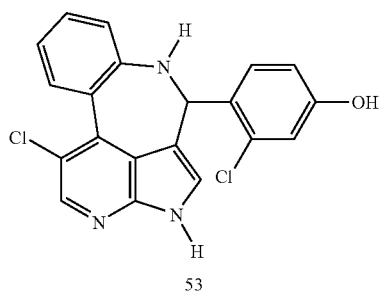 53 | A | A |
| 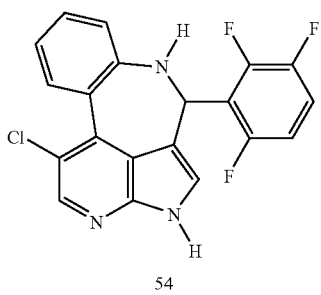 54 | A | B |
| 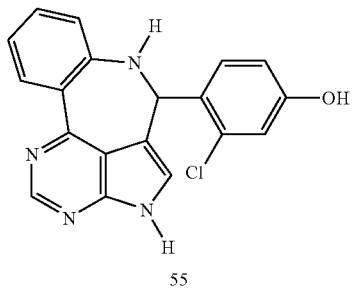 55 | A | A |
TABLE 1-continued
| Structure | JAK-2 | JAK-3 |
|---|---|---|
| 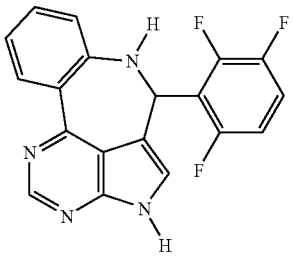 56 | A | A |
| 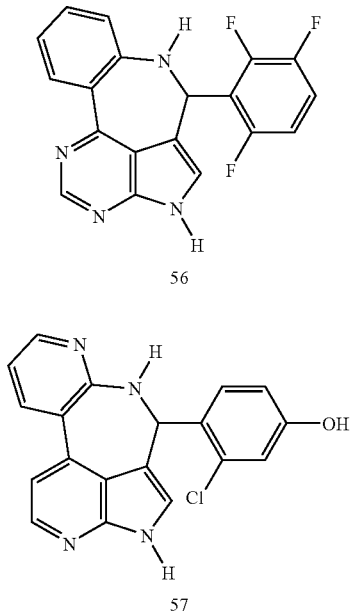 57 | A | A |
| 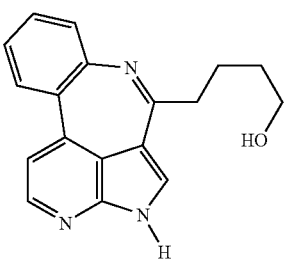 58 | B | B |
| 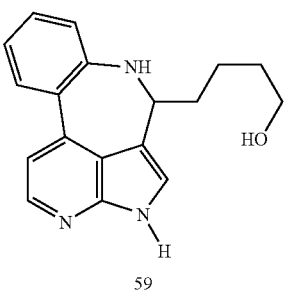 59 | B | C |
| 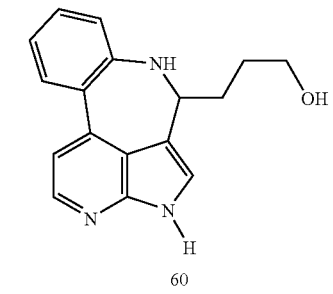 60 | B | C |

TABLE 1-continued

| Structure | JAK-2 | JAK-3 |
|---|---|---|
| 61 | A | A |
| 62 | A | A |
| 63 | A | A |
| 64 | A | A |
| 65 | A | A |
| 66 | A | A |
| 67 | A | A |
| 68 | A | A |
| 69 | A | A |
| 70 | A | B |

TABLE 1-continued

| Structure | JAK-2 | JAK-3 |
|---|---|---|
| 71 | A | A |
| 72 | C | B |
| 73 | A | A |
| 74 | A | A |
| 75 | A | A |
| 76 | A | A |
| 77 | A | A |
| 78 | B | B |
| 79 | B | B |
| 80 | C | C |

TABLE 1-continued
| Structure | JAK-2 | JAK-3 |
|---|---|---|
| 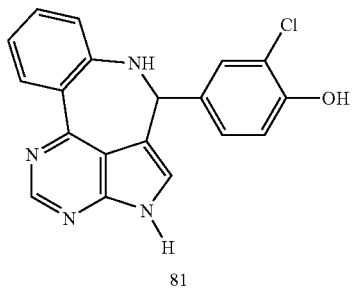 81 | A | A |
| 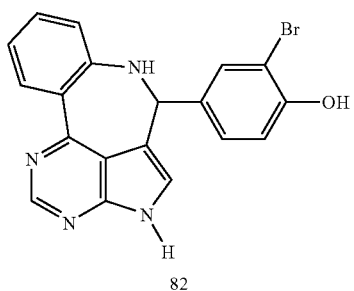 82 | A | A |
| 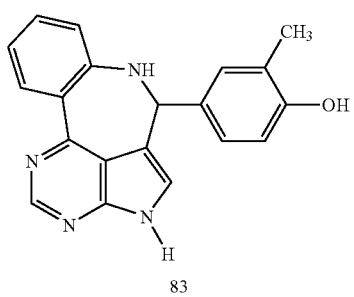 83 | A | A |
| 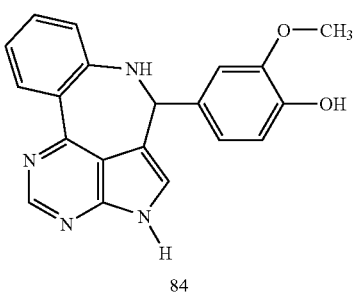 84 | A | A |
| 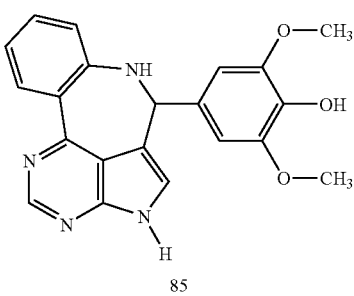 85 | B | B |
TABLE 1-continued
| Structure | JAK-2 | JAK-3 |
|---|---|---|
| 86 | C | C |
| 87 | C | C |
| 88 | C | C |
| 89 | B | C |
| 90 | B | B |

TABLE 1-continued
| Structure | JAK-2 | JAK-3 |
|---|---|---|
| 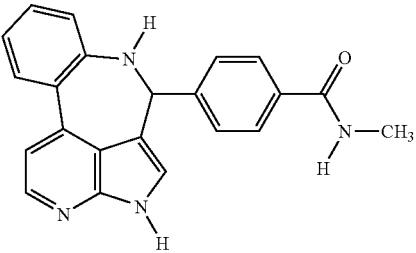 91 | C | C |
| 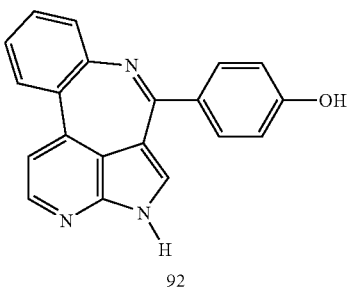 92 | A | A |
| 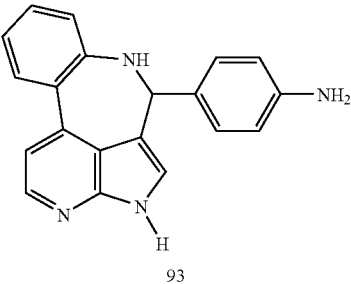 93 | A | A |
| 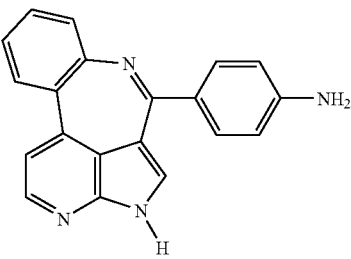 94 | A | A |
| 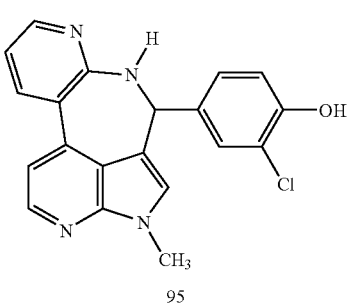 95 | A | A |
| 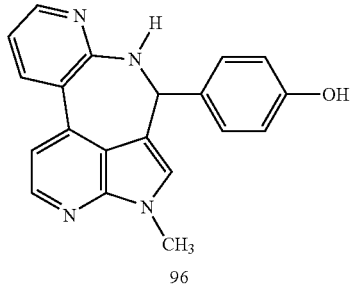 96 | A | B |
| 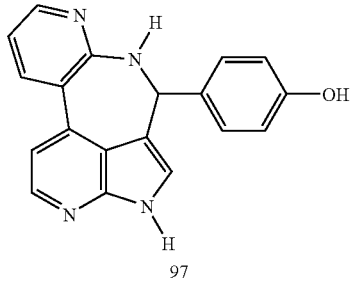 97 | A | A |
| 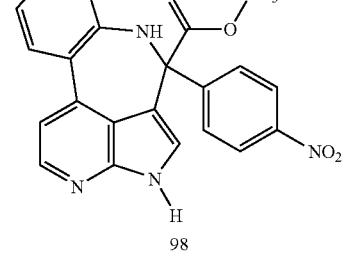 98 | A | B |
| 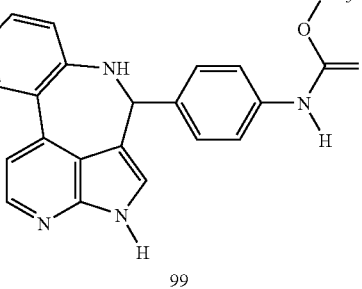 99 | C | B |
| 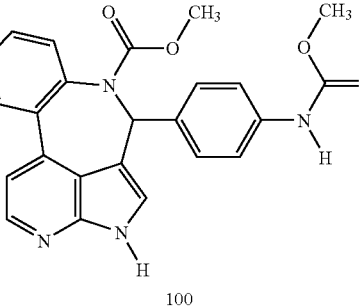 100 | C | B |

TABLE 1-continued

| Structure | JAK-2 | JAK-3 |
|---|---|---|
| 101 | C | C |
| 102 | C | C |
| 103 | A | A |
| 104 | B | B |
| 105 | A | A |
| 106 | A | A |
| 107 | A | A |
| 108 | C | C |
| 109 | B | B |
| 110 | C | C |

TABLE 1-continued
| Structure | JAK-2 | JAK-3 |
|---|---|---|
| 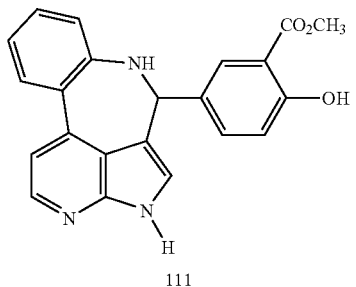 111 | C | C |
| 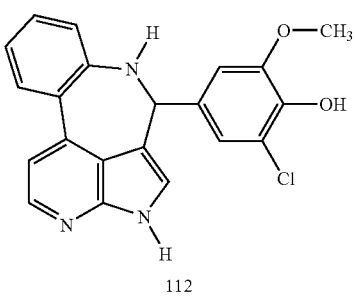 112 | A | A |
| 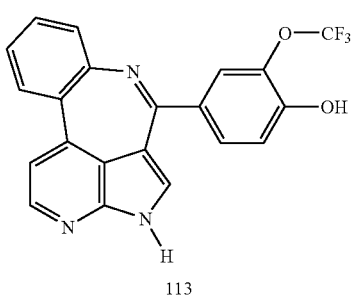 113 | A | A |
| 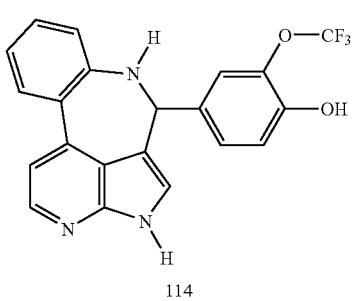 114 | B | B |
| 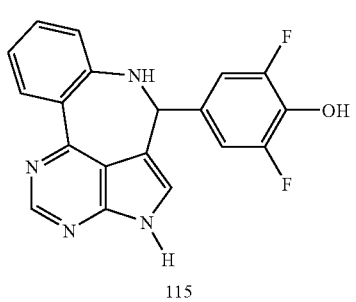 115 | A | A |
| 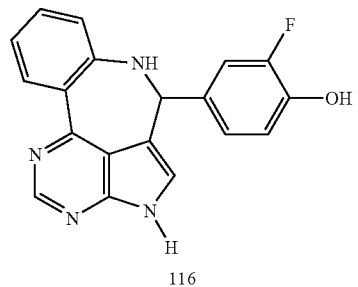 116 | A | A |
| 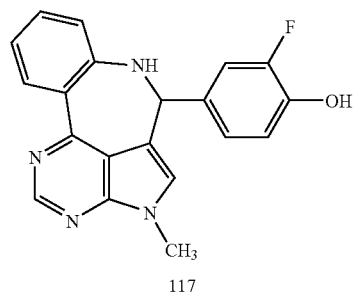 117 | A | A |
| 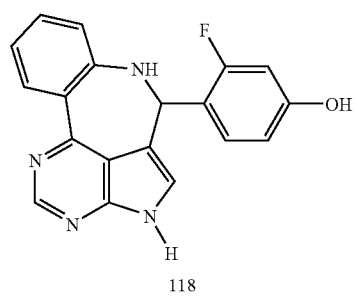 118 | A | A |
| 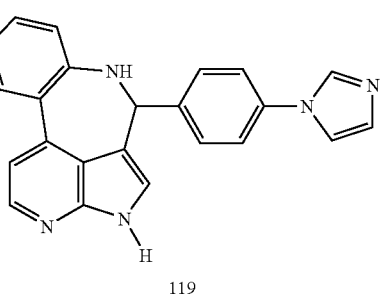 119 | B | B |
| 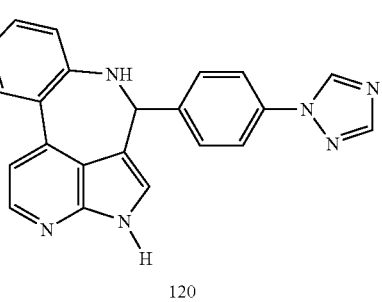 120 | C | C |

TABLE 1-continued

| Structure | JAK-2 | JAK-3 |
|---|---|---|
| 121 | C | C |
| 122 | C | C |
| 123 | B | C |
| 124 | B | B |
| 125 | A | A |
| 126 | C | C |
| 127 | A | B |
| 128 | A | A |
| 129 | C | C |
| 130 | A | B |

TABLE 1-continued
| Structure | JAK-2 | JAK-3 |
|---|---|---|
| 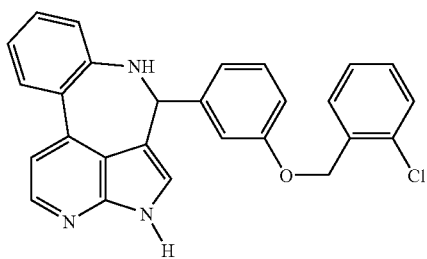 131 | A | B |
| 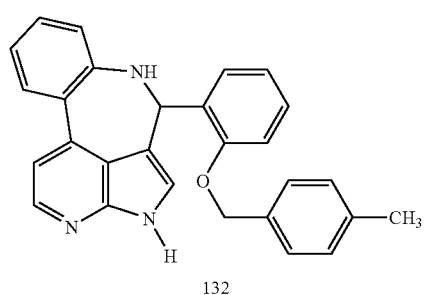 132 | C | C |
| 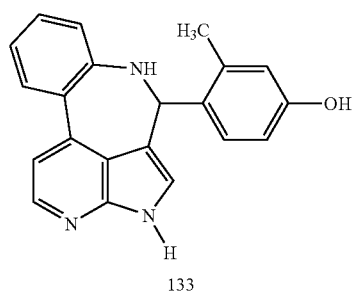 133 | A | A |
| 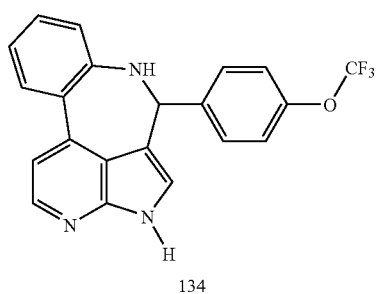 134 | B | B |
| 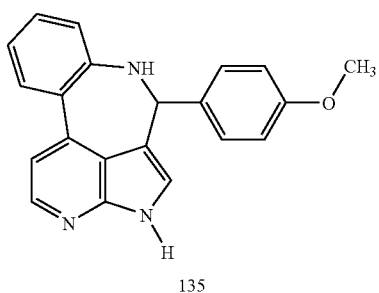 135 | A | A |
TABLE 1-continued
| Structure | JAK-2 | JAK-3 |
|---|---|---|
| 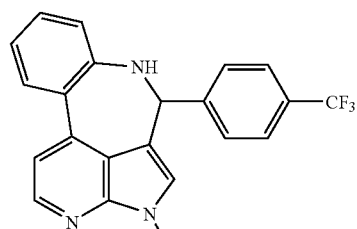 136 | C | C |
| 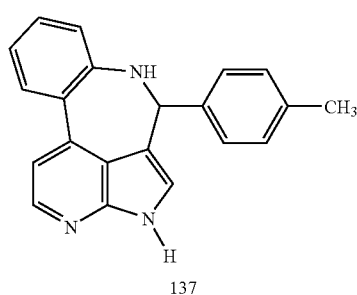 137 | B | C |
| 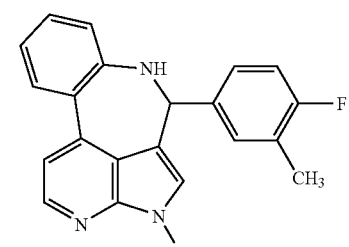 138 | C | C |
| 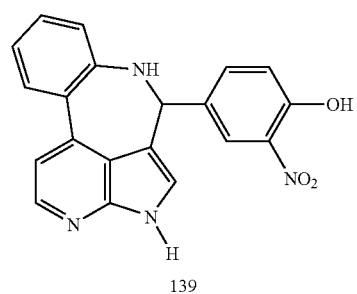 139 | B | B |
| 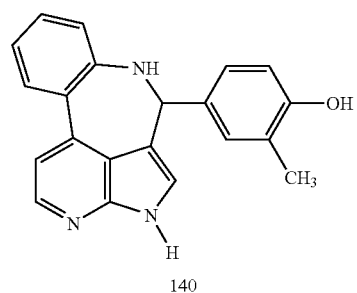 140 | A | A |

TABLE 1-continued
| Structure | JAK-2 | JAK-3 |
|---|---|---|
| 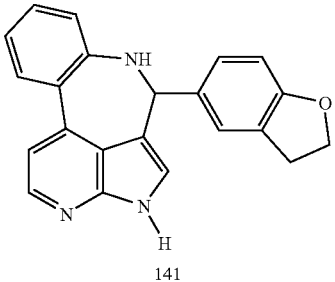 141 | A | B |
| 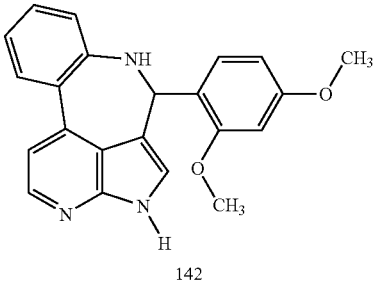 142 | C | C |
| 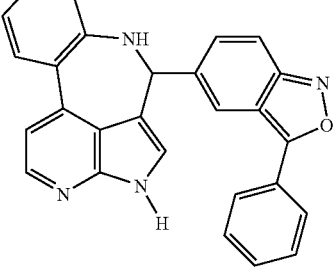 143 | C | C |
| 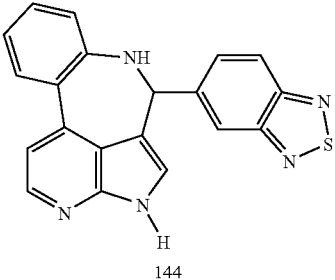 144 | B | C |
| 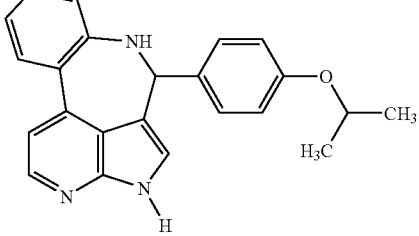 145 | A | B |
TABLE 1-continued
| Structure | JAK-2 | JAK-3 |
|---|---|---|
| 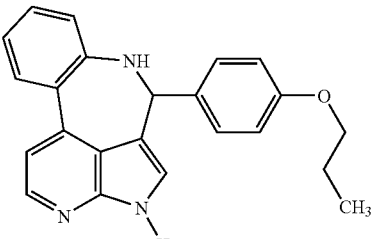 146 | A | A |
| 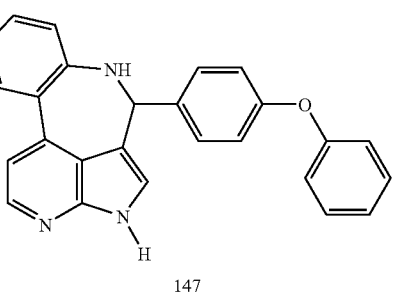 147 | C | C |
| 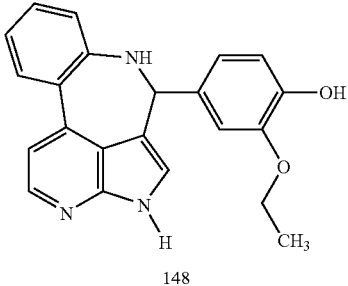 148 | B | B |
| 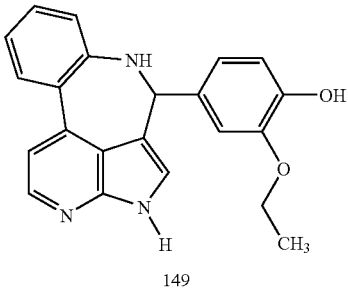 149 | B | C |
| 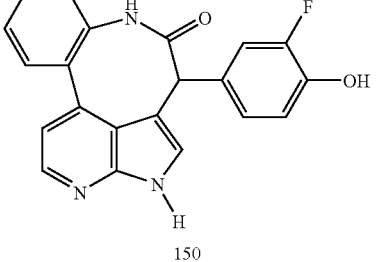 150 | A | A |

TABLE 1-continued
| Structure | JAK-2 | JAK-3 |
|---|---|---|
| 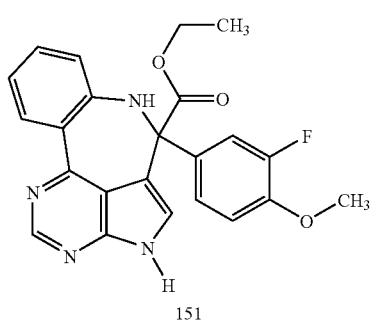 151 | B | B |
| 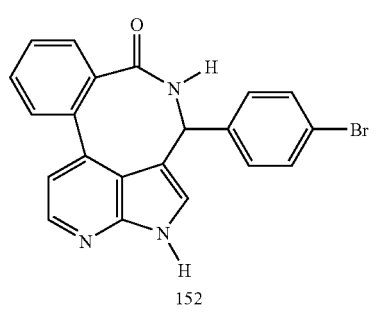 152 | C | C |
| 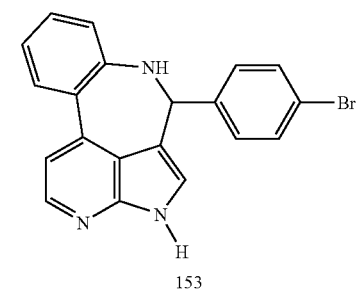 153 | C | C |
| 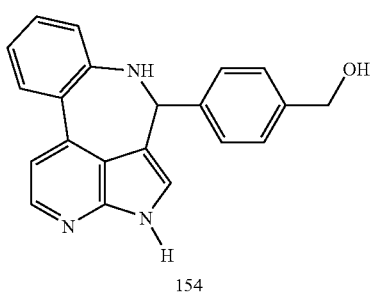 154 | A | A |
| 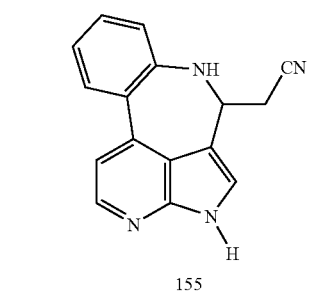 155 | A | A |
TABLE 1-continued
| Structure | JAK-2 | JAK-3 |
|---|---|---|
| 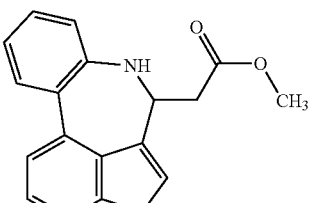 156 | B | B |
| 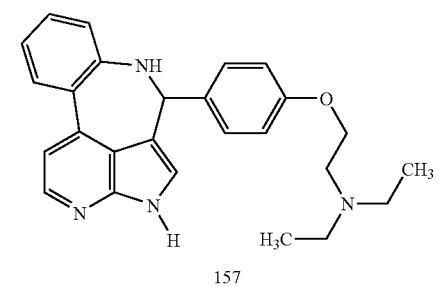 157 | A | A |
| 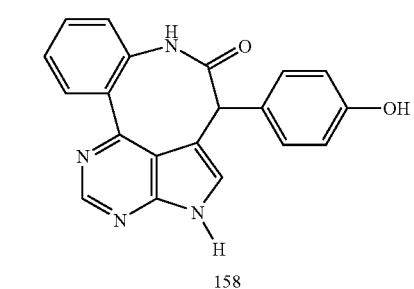 158 | A | A |
| 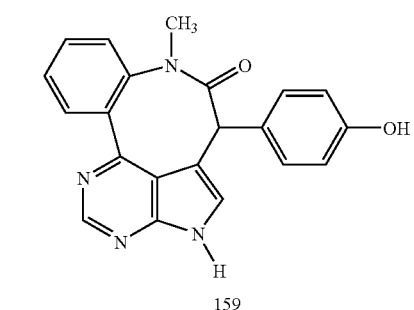 159 | A | A |
| 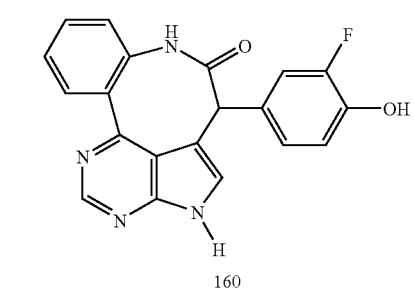 160 | A | A |

TABLE 1-continued

| Structure | JAK-2 | JAK-3 |
|---|---|---|
| 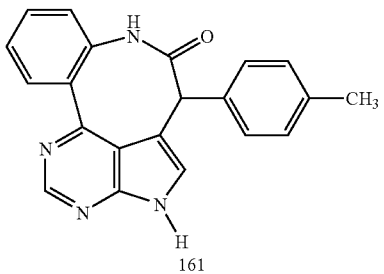
161 | A | B |
| 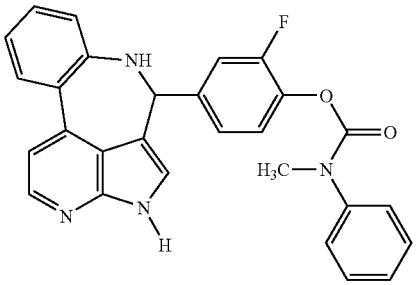
162 | B | B |

In another aspect, the invention features a process for the preparation of a compound having the formula:

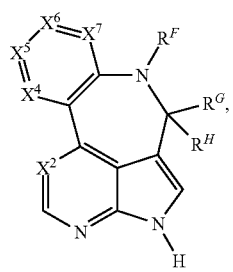
(formula II-b)

where $X^2$, $X^4$, $X^5$, $X^6$, $X^7$, $R^F$, $R^G$, and $R^H$ are as defined above for a compound of formula I-a. The process includes the following steps:
(a) reacting a compound having the formula:

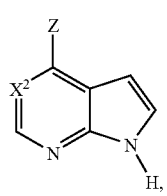
(formula III)

with a compound having the formula:

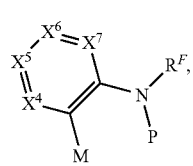
(formula IV)

where Z is Cl, Br, I, —OP(O)(OR)$_2$, —OTs, or —OTf; M is —B(OR)$_2$, —SnR$_3$, —SiR$_3$, —ZnR$_2$, —Mg-Hal, —Zn-Hal, —Cu-Hal, —ZrCp$_2$Hal, or —AlR$_2$, where each R is, independently, $C_{1-6}$ aliphatic, $C_{3-8}$ cycloaliphatic, or $C_{6-10}$ aryl; and P is a protecting group, to produce a compound having the formula:

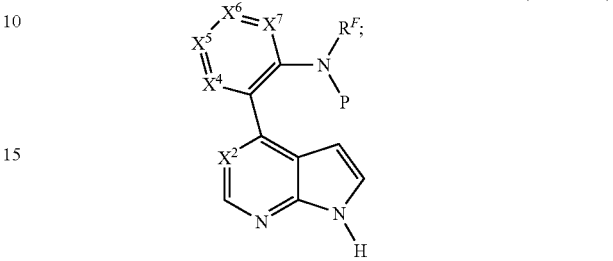
(formula V)

(b) removing protecting group P to produce a compound having the formula:

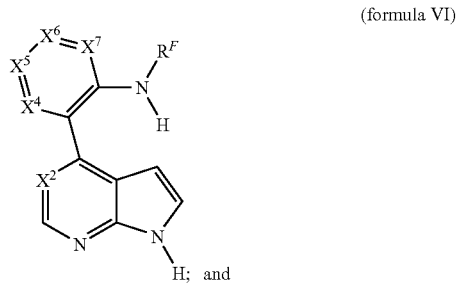
(formula VI)

(c) reacting the compound of formula V-a with a compound having the formula:

(formula VI)

under acidic conditions to produce the compound of formula II-b.

In one embodiment, the compound of formula II-b has the formula:

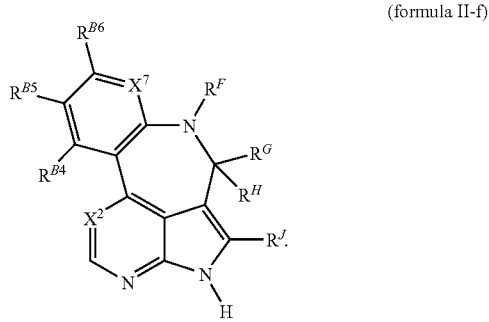
(formula II-f)

In another aspect, the invention features a process for the preparation of a compound of having the formula:

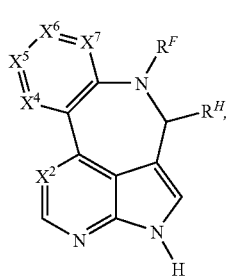

(formula II-d)

where $X^2, X^4, X^5, X^6, X^7, R^F$ and $R^H$ are as defined above for a compound of formula I-a. The process includes the following steps:

(a) reacting a compound having the formula:

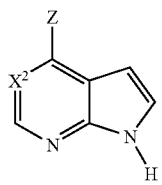

(formula III)

with a compound having the formula:

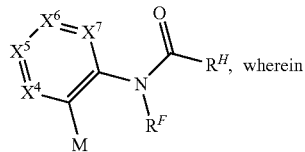

(formula IV-a)

Z is, Cl, Br, I, —OP(O)(OR)$_2$, —OTs, or —OTf and M is —B(OR)$_2$, —SnR$_3$, —SiR$_3$, —ZnR$_2$, —Mg-Hal, —Zn-Hal, —CuHal, —ZrCp$_2$Hal, or —AlR$_2$, where each R is, independently, $C_{1-6}$ aliphatic, $C_{3-8}$ cycloaliphatic, or $C_{6-10}$ aryl, to produce a compound having the formula:

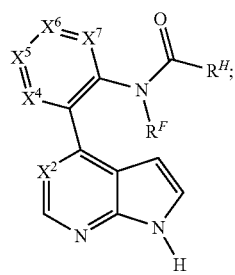

(formula V-b)

(b) subjecting said compound of formula V-b to dehydration conditions to produce an intermediate having the formula:

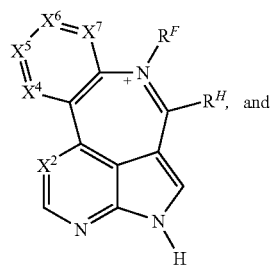

(formula II-c)

and (c) reacting said intermediate of formula II-c with a reducing agent to produce said compound having formula II-d.

In one embodiment, each of $X^2, X^4, X^5, X^6, X^7$ is C—H.

In one example, the process provides a compound of formula II-d having the formula:

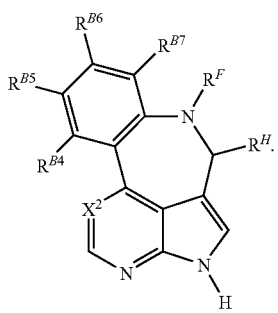

(formula II-f)

In another example, $R^F$ is hydrogen and step (c) is not performed, such that the process produces a compound having the formula:

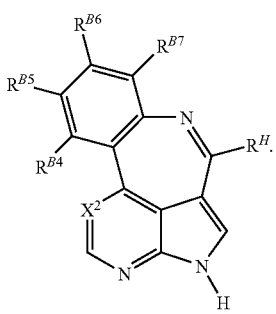

(formula II-g)

For compounds of formulae II-f and II-g, $R^{B4}, R^{B5}, R^{B6}$, and $R^{B7}$ is as defined for a compound of formula I-a. In one embodiment, $X^2$ is C—H and each of $R^{B4}, R^{B5}, R^{B6}$, and $R^{B7}$ is hydrogen.

Compositions, Formulations, and Administration of Compounds of the Invention

The invention also provides pharmaceutical compositions that include a compound of the invention and a pharmaceutically acceptable carrier, adjuvant, or vehicle. In one embodiment, the composition further includes a therapeutic agent selected from: a chemotherapeutic or anti-proliferative agent, an anti-inflammatory agent, an immunomodulatory or immunosuppressive agent, a neurotrophic factor, an agent for treating cardiovascular disease, an agent for treating destructive bone disorders, an agent for treating liver disease, an antiviral agent, an agent for treating blood disorders, an agent for treating diabetes, or an agent for treating immunodeficiency disorders. Desirably, the therapeutic agent is an immunomodulatory or immunosuppressive agent.

The invention also features the use of a compound of the invention, or a pharmaceutical composition thereof, for treating or lessening the severity of a disease, condition, or disorder in a patient selected from: a proliferative disorder, a cardiac disorder, a neurodegenerative disorder, an autoimmune disorder, a condition associated with organ transplant, an inflammatory disorder, an immunologically mediated disorder, or a bone disorder. The use includes the step of administering to the patient a therapeutically effective dose of a compound of the invention, or a pharmaceutical composition thereof. In one embodiment, the use further includes a step of administering to the patient an additional therapeutic agent selected from: a chemotherapeutic or anti-proliferative agent, an anti-inflammatory agent, an immunomodulatory or immunosuppressive agent, an agent for treating cardiovascular disease, an agent for treating destructive bone disorders, an agent for treating blood disorders, an agent for treating diabetes, or an agent for treating immunodeficiency disorders, in which the additional therapeutic agent is appropriate for the disease being treated and the additional therapeutic agent is administered together with a compound or composition of the invention as a single dosage form formulation or separately from a compound or composition of the invention as part of a multiple dosage form formulation.

In an embodiment of any treatment method of the invention, the disease, condition, or disorder is allergy, asthma, chronic obstructive pulmonary disease (COPD), diabetes, osteoarthritis, rheumatoid arthritis, Alzheimer's disease, Huntington's disease, Parkinson's disease, AIDS-associated dementia, amyotrophic lateral sclerosis (AML), multiple sclerosis (MS), schizophrenia, cardiomyocyte hypertrophy, perivascular fibrosis, benign prostatic hyperplasia, vascular smooth muscle cell proliferation, endothelial dysfunction, ischemia/reperfusion-induced injury, stroke, baldness, cancer, malignoma, hepatomegaly, hypertension, cardiovascular disease, cardiomegaly, cystic fibrosis, restenosis, psoriasis, inflammation, hypertension, angina pectoris, cerebrovascular contraction, peripheral circulation disorder, premature birth, preterm labor, atherosclerosis, vasospasm, cerebral vasospasm, coronary vasospasm, retinopathy, neurite outgrowth, glaucoma, erectile dysfunction (ED), AIDS, a respiratory syncytial viral (RSV) infection, osteoporosis, Crohn's Disease, colitis, or Raynaud's Disease. Desirably, the disease, condition, or disorder is atherosclerosis, hypertension, multiple sclerosis, erectile dysfunction, ischemia/reperfusion-induced injury, stroke, cerebral vasospasm, coronary vasospasm, cardiac hypertrophy, or glaucoma. Most desirably, the disease, disorder, or condition is asthma or transplant rejection.

The invention also features a method of measurably inhibiting JAK kinase activity in a biological sample that includes contacting the biological sample with a compound of the invention, or a pharmaceutical composition thereof.

The amount of compound in a composition of this invention is such that it measurably inhibits a protein kinase, such as, for example, a JAK family kinase, in a biological sample or in a patient. The term "measurably inhibit," as used herein means a measurable change in kinase activity, particularly JAK family activity, between a sample comprising a compound of this invention and a JAK kinase and an equivalent sample comprising JAK kinase, respectively, in the absence of said compound.

The term "patient," as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitory active metabolite or residue thereof. As used herein, the term "inhibitory active metabolite or residue thereof" means that a metabolite or residue thereof is also an inhibitor of a JAK family kinase.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology,* eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled.

Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

A compound or composition of the invention can be used as a monotheraphy to treat or lessen the severity of a disease, condition or disorder in a patient selected from: a proliferative disorder, a cardiac disorder, a neurodegenerative disorder, a psychotic disorder, an autoimmune disorder, a condition associated with organ transplant, an inflammatory disorder, an immunologically-mediated disorder, a viral disease, or a bone disorder by administering to the patient a compound or a composition of the invention in an effective amount.

The treatment method can further include the additional step of administering to the patient an additional therapeutic agent (combination therapy) selected from: a chemotherapeutic or anti-proliferative agent, an anti-inflammatory agent, an immunomodulatory or immunosuppressive agent, a neurotrophic factor, an anti-psychotic agent, an agent for treating cardiovascular disease, an agent for treating destructive bone disorders, an agent for treating liver disease, an anti-viral agent, an agent for treating blood disorders, an agent for treating diabetes, or an agent for treating immunodeficiency disorders, wherein the additional therapeutic agent is appropriate for the disease being treated and the additional therapeutic agent is administered together with a compound or composition of the invention as a single dosage form or separately from the compound or composition as part of a multiple dosage form.

Diseases, conditions, or disorders that can be so treated by monotherapy or combination therapy include allergy, asthma, chronic obstructive pulmonary disease (COPD), diabetes, osteoarthritis, rheumatoid arthritis, Alzheimer's disease, Huntington's disease, Parkinson's disease, AIDS-associated dementia, amyotrophic lateral sclerosis (AML), multiple sclerosis (MS), schizophrenia, cardiomyocyte hypertrophy, perivascular fibrosis, benign prostatic hyperplasia, vascular smooth muscle cell proliferation, endothelial dysfunction, ischemia/reperfusion-induced injury, stroke, baldness, cancer, malignoma, hepatomegaly, hypertension, cardiovascular disease, cardiomegaly, cystic fibrosis, restenosis, psoriasis, inflammation, hypertension, angina pectoris, cerebrovascular contraction, peripheral circulation disorder, premature birth, preterm labor, atherosclerosis, vasospasm, cerebral vasospasm, coronary vasospasm, retinopathy, neurite outgrowth, glaucoma, erectile dysfunction (ED), AIDS, a respiratory syncytial viral (RSV) infection, osteoporosis, Crohn's Disease, colitis, or Raynaud's Disease.

In some embodiments, the present invention relates to a method for treating or lessening the severity of a cancer. In further embodiments, the present invention relates to a method for treating or lessening the severity of a cancer selected from brain (gliomas), breast, colon, head and neck, kidney, lung, liver, melanoma, ovarian, pancreatic, prostate, sarcoma, or thyroid. In yet further embodiments, the present invention relates to a method for treating or lessening the severity of pancreatic, prostate, or ovarian cancer.

The invention provides a method of inhibiting JAK kinase activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly JAK kinase activity, in a biological sample is useful for a variety of purposes known to one of skill in the art. Examples of such purposes include, but are not limited to, biological specimen storage and biological assays. Inhibition of JAK kinase activity in a biological sample does not relate to therapeutic methods, such as, for example, blood transfusions or organ transplantations.

The invention also provides a method of inhibiting JAK kinase activity in a patient, comprising administering to the patient a compound or composition of the invention. In an embodiment, the invention comprises a method of treating or lessening the severity of a JAK-mediated condition or disease in a patient. The term "JAK-mediated disease," as used herein, means any disease or other deleterious condition in which a JAK family kinase, in particular JAK-2 or JAK-3, is known to play a role. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as familial amyotrophic lateral sclerosis (FALS), as well as in solid and hematologic malignancies such as leukemias and lymphomas.

A compound or composition of the invention may also be used to treat a myeloproliferative disorder. In one embodiment, the myeloproliferative disorder is polycythemia vera, essential thrombocythemia, or chronic idiopathic myelofibrosis. In another embodiment, the myeloproliferative disorder is myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound of this invention are another embodiment of the present invention. The compounds may also be coated on implantable medical devices, such as beads, or co-formulated with a polymer or other molecule, to provide a "drug depot," thus permitting the drug to be released over a longer time period than administration of an aqueous solution of the drug.

Preparation of the Compounds of the Invention

The following definitions describe terms and abbreviations used herein:
ATP adenosine triphosphate
Boc t-butoxylcarbonyl
dba dibenzylideneacetone
DCM dichloromethane
DME 1,2-dimethoxyethane
DMF dimethylformamide
dppf 1,1'-bis(diphenylphosphino)-ferrocene
DTT dithiothreitol
ESMS electrospray mass spectrometry
Ether ethyl ether
EtOAc ethyl acetate
Glu glutamic acid
HEPES 4-(2-hydroxyethyl)-1-piperazineethanesulfonic acid
HPLC high performance liquid chromatography
LC-MS liquid chromatography-mass spectrometry
Me methyl
MeOH methanol
NMP N-methylpyrrolidone
o-tol ortho-toluoyl
Ph phenyl
tBu tertiary butyl
Tf trifluorosulfonyl
TFA trifluoacetic acid
Ts toluenesulfonyl In general, the compounds of this invention may be prepared by methods described herein or known to those skilled in the art for the preparation of analogous compounds. The following non-limiting schemes and examples are presented to further exemplify the invention.

General Synthetic Procedures

As shown in Scheme 1, a compound of formula III, containing leaving group Z (such as, for example, a halogen, phosphonate, tosylate, or triflate) is reacted with a palladium catalyst/ligand system (such as, for example, Pd(PPh$_3$)$_4$, Pd(PtBu$_3$)$_4$, Pd[P(Me)(tBu$_3$)]$_4$, PdCl$_2$(PPh$_3$)$_2$, PdCl$_2$(dppf)$_2$, Pd$_2$(dba)$_3$BINAP, or Pd$_2$(dba)$_3$P(o-tol)$_3$ (see Fu and Littke, *Angew. Chem. Int. Ed.* 41:4176-4211, 2002; Nicolaou et al., *Angew. Chem. Int. Ed.* 44:4442-4489, 2005; or Hassen et al., *Chemical Reviews* 102(5):1359-1469, 2002) in the presence of a base and a compound of formula IV, where M is —B(OAlkyl)$_2$ or —B(OH)$_2$(Suzuki reaction); —Mg-Hal (Kumada reaction); —Zn-Hal (Negishi reaction); —Sn (Alkyl)$_3$ (Stille reaction); —Si(Alkyl)$_3$ (Hiyama reaction); —Cu-Hal; —ZrCp$_2$Cl; or —AlMe$_2$; and P is a nitrogen protection group, to produce a compound of formula V, where X$^2$, X$^4$, X$^5$, X$^6$, X$^7$, and R$^F$ can be defined as indicated elsewhere herein.

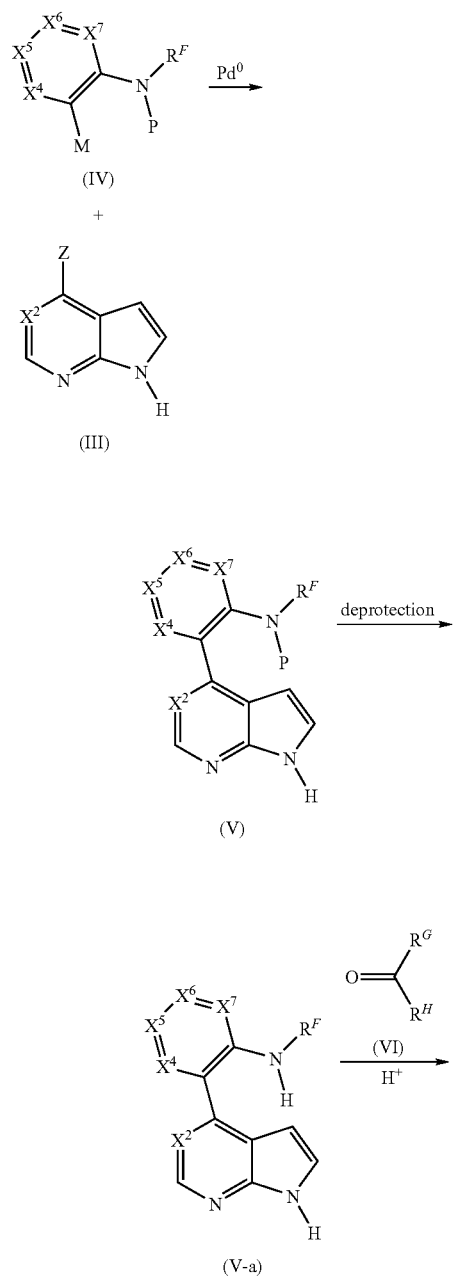

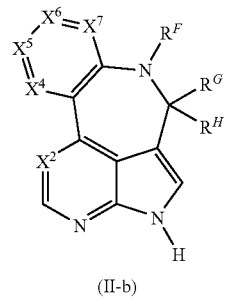

(II-b)

The protecting group, P, which can be, for example, an acetate or a Boc group, is removed by the requisite deprotection conditions and the resulting compound of formula V-a is reacted with a compound of formula VI, where R$^G$ and R$^H$ are as defined elsewhere herein, under acidic conditions to produce a compound of formula II-b. The acid used can be a mineral acid, such as, for example, hydrochloric or sulfuric acid; an organic acid, such as, for example, acetic acid or trifluoroacetic acid; or a Lewis acid, such as, for example, boron trifluoride. Typically, the reaction mixture is heated, optionally under microwave radiation, to affect the cyclization. If desired, the reaction mixture can be further heated, optionally under microwave irradiation, in the presence of atmospheric oxygen or another oxidant to produce a compound in which R$^F$, R$^G$, and the carbon and nitrogen atoms between them form a carbon-nitrogen double bond.

An alternate procedure useful for the preparation of a compound of formula II-b, where R$^G$ is hydrogen (e.g., a compound of formula II-d), or a compound of formula II-e, is shown in Scheme 2. The coupling of a compound of formula IV-a to a compound of formula III is performed as described above for the coupling of a compound of formula IV to a compound of formula III. The resulting compound of formula V-b is subjected to dehydration conditions to produce a compound of formula II-c, where X$^2$, X$^4$, X$^5$, X$^6$, X$^7$, R$^F$, and R$^H$ can be defined as indicated elsewhere herein. Suitable reagents for this reaction include, for example, phosphorus oxychloride, thionyl chloride, phosphorous tribromide, phosphorous pentoxide, or any other suitable reagent for effecting a Bischler-Napieralski-like reaction (see, for example, Schmutz et al., *Helv. Chem. Acta* 50:245, 1967 or Whaley and Govindachari, *Org. React.* 6:74, 1951). Typically, the reaction mixture is heated to affect the cyclization. The compound of formula II-c can then be reduced to produce a compound of formula II-d. Suitable reducing agents include hydride reducing agents, such as, for example, sodium borohydride. Chiral borohydride reagents can also be used to influence the chirality of the carbon bearing R$^H$. Alternatively, when R$^F$ is hydrogen, the reduction step can be omitted, thereby producing a compound of formula II-e.

Scheme 2

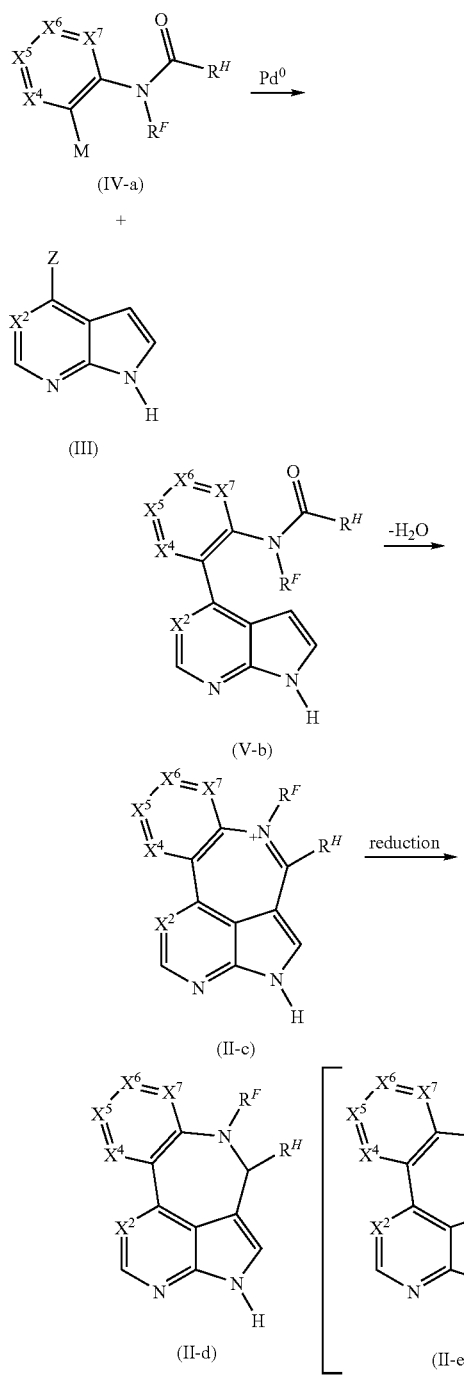

When the compound of formula VI in Scheme 1 is an alpha-keto ester and it is reacted with a compound of formula V-a, the result is a compound of V-c, where $R^G$ is —C(O)OR (R is defined as indicated elsewhere herein). The 7-membered ring of a compound of formula V-c can be opened up by reduction, such as, for example, by hydrogenation, to give a compound of formula VII. Hydrolysis of the ester to the carboxylic acid of formula VIII and ring closure via condensation of the carboxylic acid with the amine yields a compound of formula IX. Such a ring closure can be performed using conventional condensation reagents known to a person skilled in the art, including, for example, 1-benzotriazol-1-yloxy-bis(pyrrolidino)uronium hexafluorophosphate (BBC), O-(7-azabenzotriazol-1-yl)-1,1,3,3-tetramethyluronium hexafluorophosphate (HATU), O-(7-azabenzotriazol-1-yl)-1,1,3,3-bis(tetramethylene)uronium hexafluorophosphate (HAPyU), O-(benzotriazol-1-yl)-1,1,3,3-tetramethyluronium hexafluorophosphate (HBTU), 1,3-diisopropylcarbodiimide (DIC), 1-ethyl-3-(3'-dimethylaminopropyl)carbodiimide hydrochloride, (EDCI)O-(7-azabenzotriazol-1-yl)-tris(dimethylamino)phosphonium hexafluorophosphate (AOP), 1-benzotriazolyoxytris(dimethylamino)phosphonium hexafluorophosphate (BOP), 7-azobenzotriazolyoxytris(pyrrolidino)phosphonium hexafluorophosphate (PyABOP), and 1-benzotriazolyoxytris(pyrrolidino)phosphonium hexafluorophosphate (PyBOP). When $R^F$ is hydrogen, compounds of formula IX can be further elaborated by forming an imino triflate (by treatment with triflic anhydride and base) and using this intermediate in a catalyzed metallation reaction, such as described above in Scheme 1, to produce compounds of formula I-a in which W is —NHC(=X)—, where X is [hydrogen, R].

Scheme 3

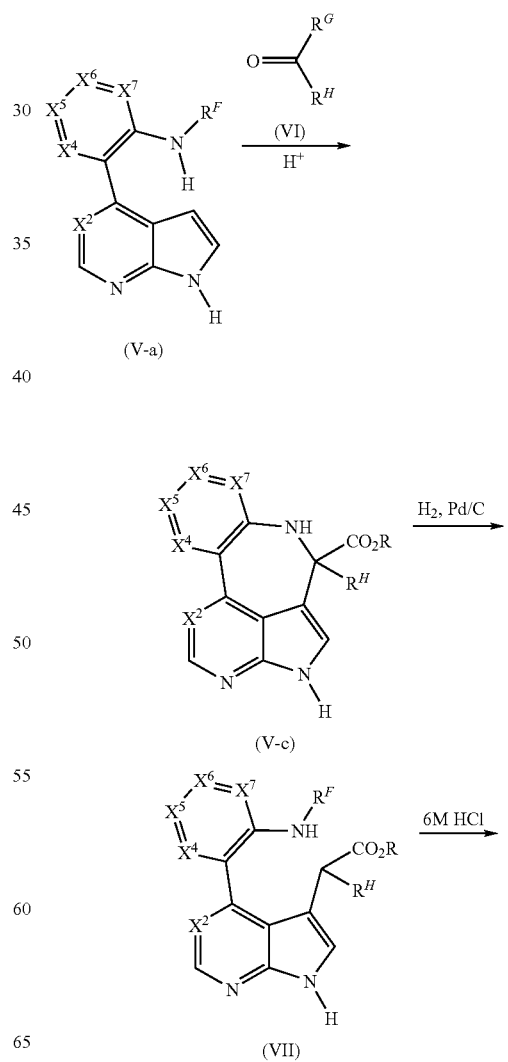

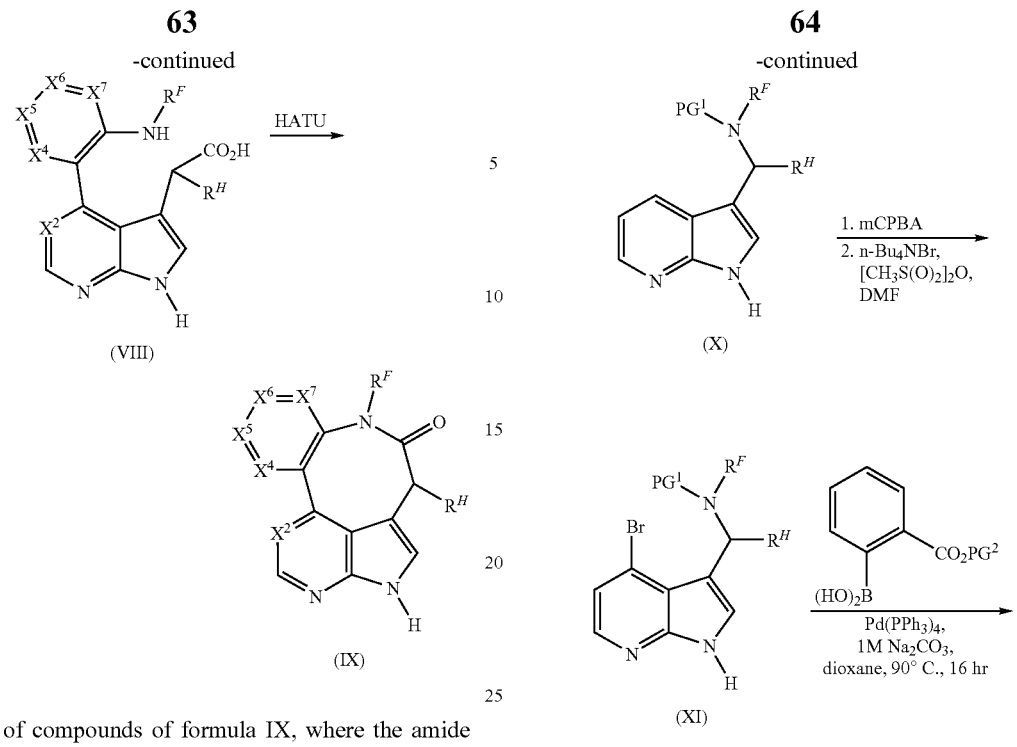

Isomers of compounds of formula IX, where the amide bond has the reverse orientation, can be prepared as shown in Scheme 4. Metallation of 1H-pyrrolo[2,3-b]pyridine followed by reaction with an appropriately substituted imine, forms a compound of formula X, where $R^F$ is a suitable amine protecting group, such as, for example, 4-methoxybenzyl or trifluoromethylsulfonyl. Optionally, $R^F$ is as defined for a compound of formula I-a and the amine is subsequently protected with protecting group $PG^1$. A compound of formula X is reacted with meta-chloroperbenzoic acid (mCPBA), or another suitable oxidant, to form an N-oxide intermediate. Subsequent reaction of this intermediate with tetramethylammonium bromide and methylsulfonyl anhydride forms a compound of formula XI, which is then treated with a phenylboronic acid analog that contains an alpha carboxylic acid, which is protected with a suitable carboxylic acid protecting group $PG^2$, to produce a compound of formula XII. Methods for the preparation of aryl and alkenyl boronic acid analogs and their use in subsequent coupling reactions has been described in U.S. Pat. Nos. 6,939,985 and 6,559,310, and in U.S. Patent Application No. 20040133028. Deprotection of both carboxylic acid and amine protecting groups, followed by amide bond formation, such as, for example, described above in Scheme 3, forms a compound of formula XIII. When $R^F$ is hydrogen, compounds of formula IX can be further elaborated by forming an imino triflate and using this intermediate in a catalyzed metallation reaction, such as described above in Scheme 1, to produce compounds of formula I-a in which W is —C(=X)NH—, where X is [hydrogen, R].

Scheme 4

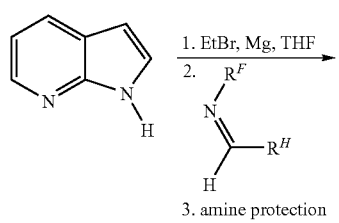

Alternatively, as shown in Scheme 5, a compound of formula XIV can be reacted with a compound of formula XV in a palladium catalyzed metallation reaction to produce a compound of formula XVI. Subsequent reaction of this intermediate with an aldehyde, such as, for example, $R^H$—CHO, under acidic conditions produces a compound of formula XIII. Compounds 126, 127, and 129 were prepared in such a manner.

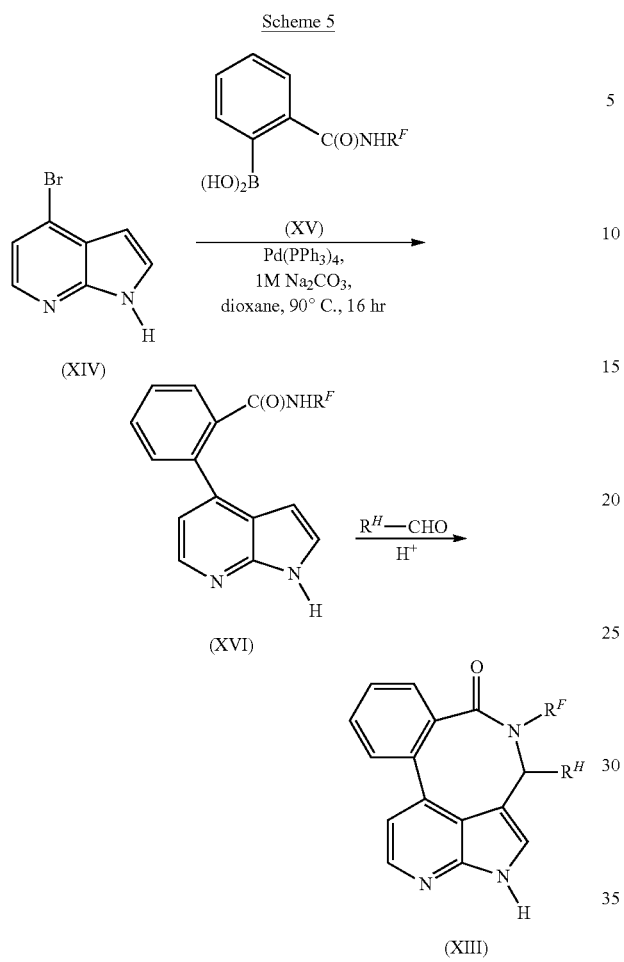

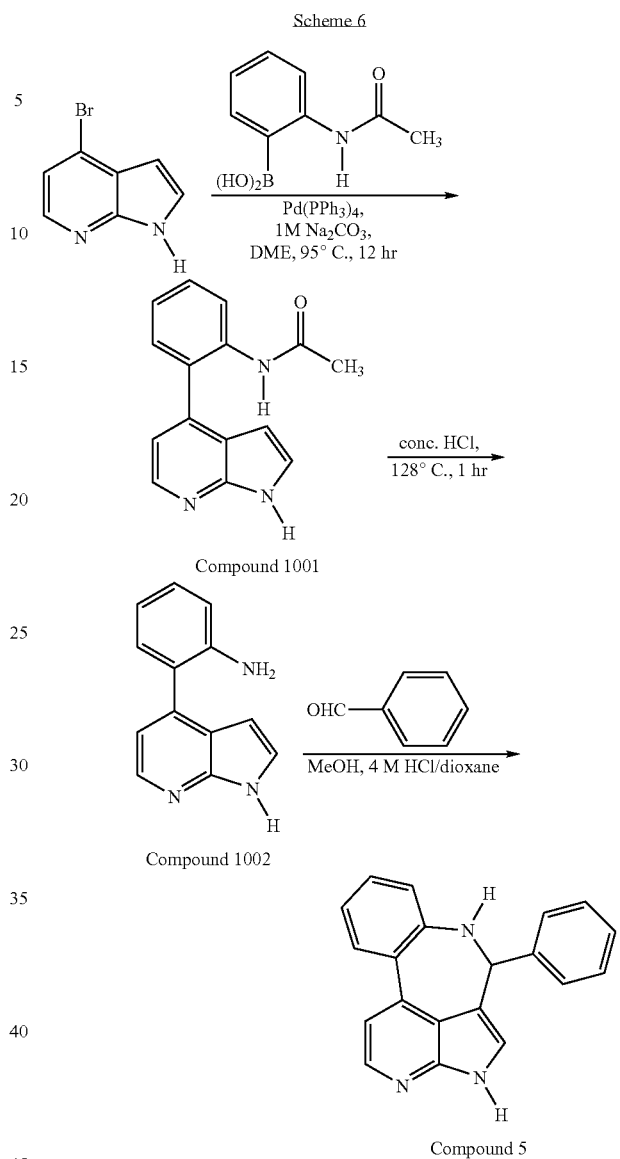

EXAMPLE 1

Synthesis of Compound 5

As shown in Scheme 6,4-bromo-1H-pyrrolo[2,3-b]pyridine (1.01 g), 2-acetamidophenylboronic acid (1.63 g), Pd(PPh$_3$)$_4$ (0.345 mg), and 1M Na$_2$CO$_3$ (8 mL) were mixed in DME (20 mL) and heated at 95° C. overnight. The reaction was cooled and water (60 mL) added. Extraction with dichloromethane (3×) and concentration of the combined organic extracts gave N-(2-(1H-pyrrolo[2,3-b]pyridin-4-yl)phenyl) acetamide (compound 1001), which was treated with concentrated hydrochloric acid (20 mL) and toluene (1 mL) and heated at 128° C. for 30 min. Evaporation of the volatiles gave a residue, to which saturated sodium bicarbonate was added. The resulting mixture was extracted with dichloromethane (3×). Concentration of the organics and purification of the residue via silica gel chromatography (50 to 80% EtOAc/hexane) gave 2-(1H-pyrrolo[2,3-b]pyridin-4-yl)benzenamine (compound 1002, 1.07 g). To compound 1002 (14 mg) in methanol (1 mL) was added 4N HCl-dioxane (0.05 mL) and benzaldehyde (16 mg). The reaction mixture was capped and heated at 90° C. for 1 h. About 75% of the methanol was removed by evaporation, followed by the addition of ethyl ether (5 mL). The resulting solid was filtered and washed with ether (2×) to yield compound 5 as the hydrochloride salt (22.5 mg).

Compounds 1, 6-22, 24-43, 45-46, 60, 64-80, 86-89, 91, 104-108, 110-112, 114, and 119-124, and 128 (see Table 1 for compound structures) were prepared from compound 1002 by varying the aldehyde and using a procedure similar to that for the synthesis of compound 5.

Compound 23 was obtained by treating compound 8 with refluxing 6M HCl for 1 hour.

Compound 90 was obtained by hydrogenation of compound 89 over 10% Pd/C.

In the preparation of compound 43, compound 44 was also obtained by HPLC purification.

Compound 93 was obtained by treating compound 83 with SnCl$_2$.2H$_2$O in refluxing ethanol for 4 hours.

Compound 58 was obtained via reaction of compound 1002 with 2-ethoxytetrahydropyran in methanol/4M HCl-dioxane at 90° C. When the same components were reacted in a microwave at 120° C. for 20 minutes, compound 59 was obtained. Substituting 2-ethoxytetrahydrofuran for 2-ethoxytetrahydropyran in an analogous microwave procedure produced compound 60.

Compound 63 was obtained by heating compound 46 in methanol for 3 days at 90° C.

EXAMPLE 2

Synthesis of Compound 102

As shown in Scheme 7, compound 1002 (66 mg), 4-nitrophenylglyoxylic acid (135 mg), 4M HCl-dioxane (0.4 mL), and methanol (4 mL) were mixed together and heated at 90° C. overnight. After cooling, addition of ether, and filtration, compound 98 was obtained as a solid (106 mg). To compound 98 (64 mg) in 3 mL of methanol was added $SnCl_2 \cdot 2H_2O$ (0.3 g). After heating at 80° C. for 1 hour, followed by cooling, the reaction mixture was filtered through Celite™ and concentrated to give compound 102 after purification via silica gel chromatography.

(8 mg). The resulting suspension was stirred under a hydrogen balloon for 24 hours. Filtration through Celite™ and evaporation under vacuum gave compound 1003 (25 mg). Compound 1003 (20 mg) was refluxed in 6 M hydrochloric acid for 6 hours. Evaporation under vacuum gave the intermediate carboxylic acid, which was dissolved in DMF (2 mL), followed by the addition of 2-(7-aza-1H-benzotriazole-1-yl)-1,1,3,3-tetramethyluronium hexafluorophosphate (HATU) (40 mg) and diisopropylethylamine (DIEA, 0.02 mL). The resulting mixture was stirred at 40° C. overnight, followed by the addition of water (20 mL) and TFA (0.1 mL). The crude product was extracted with ethyl acetate (3×), dried over $Na_2SO_4$, concentrated in vacuo, and purified by HPLC to obtain compound 125.

Scheme 7

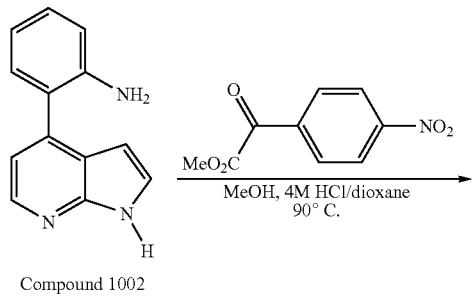

Compound 1002

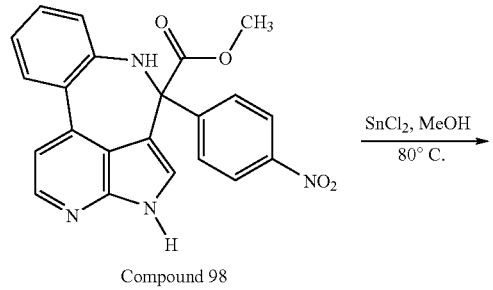

Compound 98

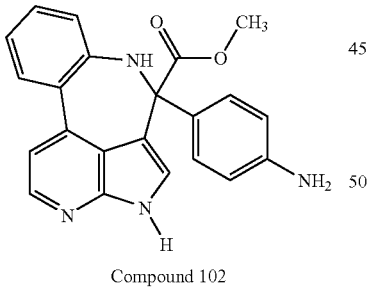

Compound 102

EXAMPLE 3

Synthesis of Compound 125

As shown in Scheme 8, compound 1002 (58 mg), 4-hydroxyphenylglyoxylic acid (69 mg), 4M HCl-dioxane (0.4 mL), and methanol (4 mL) were mixed together and heated at 90° C. overnight. After cooling, the addition of ether and filtration, compound 103 (0.11 g) was obtained as a yellow solid. To compound 103 (24.4 mg), methanol (2 mL), and 2 drops of concentrated hydrochloric acid was added 10% Pd/C Scheme 8

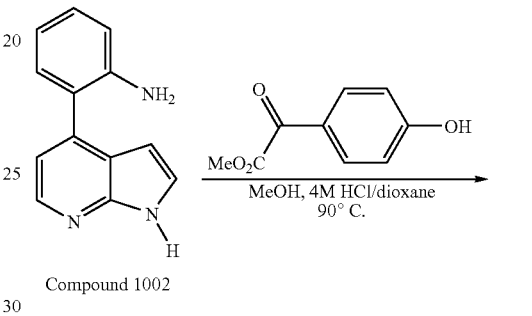

Compound 1002

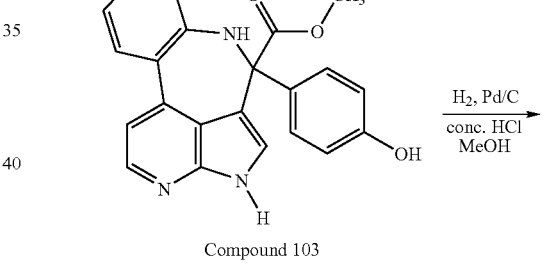

Compound 103

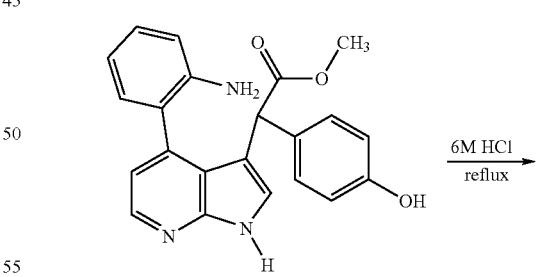

Compound 1003

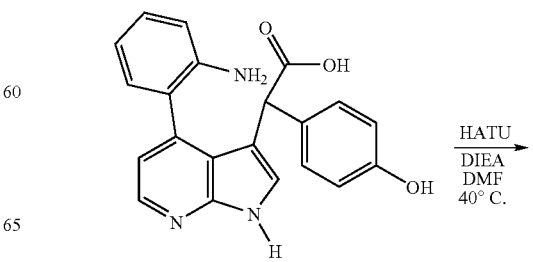

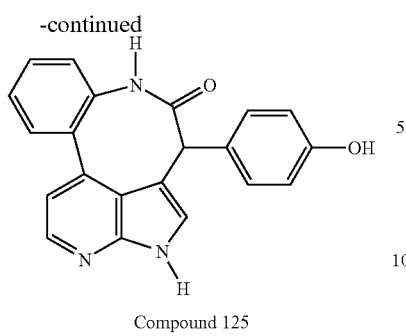

Compound 125

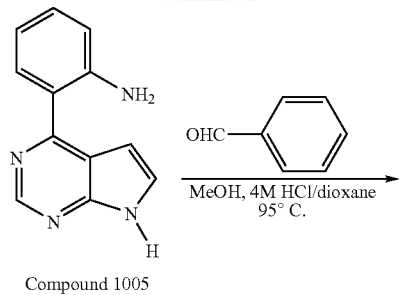

Compound 1005

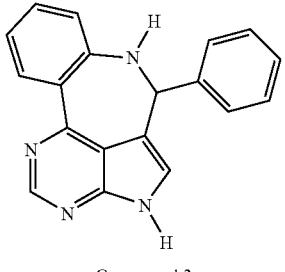

Compound 3

EXAMPLE 4

Synthesis of Compound 3

As shown in Scheme 9, 4-chloro-7H-pyrrolo[2,3-d]pyrimidine (1.02 g, mmol), 2-acetamidophenylboronic acid (1.80 g), Pd(PPh$_3$)$_4$ (0.4 g), and 1M Na$_2$CO$_3$ (8 mL) were mixed in DME (20 mL) and heated at 95° C. overnight. The reaction was cooled and the solvents were removed in vacuo, followed by the addition of water (60 mL). Extraction with dichloromethane (3×) and concentration of the combined organic extracts gave, after silica gel chromatography, N-(2-(7H-pyrrolo[2,3-c/]pyrimidin-4-yl)phenyl)acetamide (compound 1004), which was subsequently treated with concentrated hydrochloric acid (20 mL) and toluene (1 mL). The resulting mixture was heated for 30 min at 128° C. The volatiles were removed in vacuo to give a solid, to which saturated sodium bicarbonate was added. Extraction with 5% MeOH/DCM (3×) and concentration under reduced pressure gave a residue, to which ether was added. The resulting solid was filtered and washed with ether (2×) to give 2-(7H-pyrrolo[2,3-d]pyrimidin-4-yebenzenamine (compound 1005) as a yellow solid (1.17 g).

A mixture of compound 1005 (10 mg), benzaldehyde (20 mg), 4M HCl-dioxane (0.1 mL), and methanol (1 mL) were heated at 95° C., and the progress of the reaction was monitored by LC-MS. When the reaction was judged complete, the reaction mixture was concentrated and ether was added. Compound 3 was filtered off and obtained as an HCl salt.

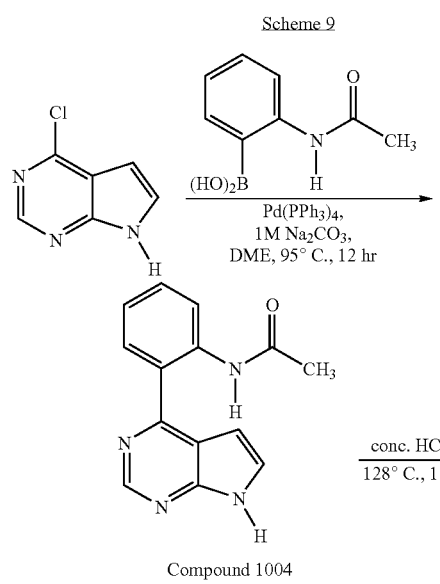

Scheme 9

Compound 1004

Compounds 2, 4, 49-50, 55-56, 81-85, 115-116, and 118 (see Table 1 for compound structures) were prepared from compound 1005 by varying the aldehyde and using a procedure similar to that for the synthesis of compound 3. Compound 117 was isolated as a side product during the purification of compound 116

Compound 92 was prepared by reacting compound 1005 (10.5 mg), 4-hydroxybenzaldehyde (15 mg), and TFA (1 mL) at 140° C. for 20 minutes under microwave radiation. The crude product was isolated by removal of the solvents in vacuo, followed by HPLC purification.

EXAMPLE 5

Synthesis of Compound 48

As shown in Scheme 10, 4-bromo-1H-pyrrolo[2,3-b]pyridine (0.11 g, mmol), 2,2-dimethyl-N-[3-(4,4,5,5-tetramethyl-[1,3,2]dioxaborolan-2-yl)-pyridin-2-yl]-propionamide (0.304 g), Pd(PPh$_3$)$_4$ (0.04 mg), and 1M Na$_2$CO$_3$ (0.8 mL) were mixed in DME (3 mL) and heated at 95° C. overnight. The reaction mixture was cooled and water (20 mL) was added. Extraction with dichloromethane (3×) and concentration of the combined organic extracts gave, after silica gel chromatography (1:1 ethyl acetate/hexanes), compound 1006, which was subsequently treated with refluxing concentrated hydrochloric acid (10 mL) for two days. The liquid was removed under vacuum to give a solid, to which saturated sodium bicarbonate was added. Extraction with dichloromethane (3×) and concentration under a reduced pressure gave a residue, to which ether was added. Filtration gave compound 1007 (48 mg).

A mixture of compound 1007 (10 mg), 3-fluorobenzaldehyde (20 mg), 4M HCl-dioxane (0.1 mL), and methanol (1 mL) was heated at 160° C. under microwave radiation for 40 minutes. The reaction mixture was concentrated in vacuo and ether was added. Compound 48 was filtered off and subsequently purified by HPLC.

Scheme 10

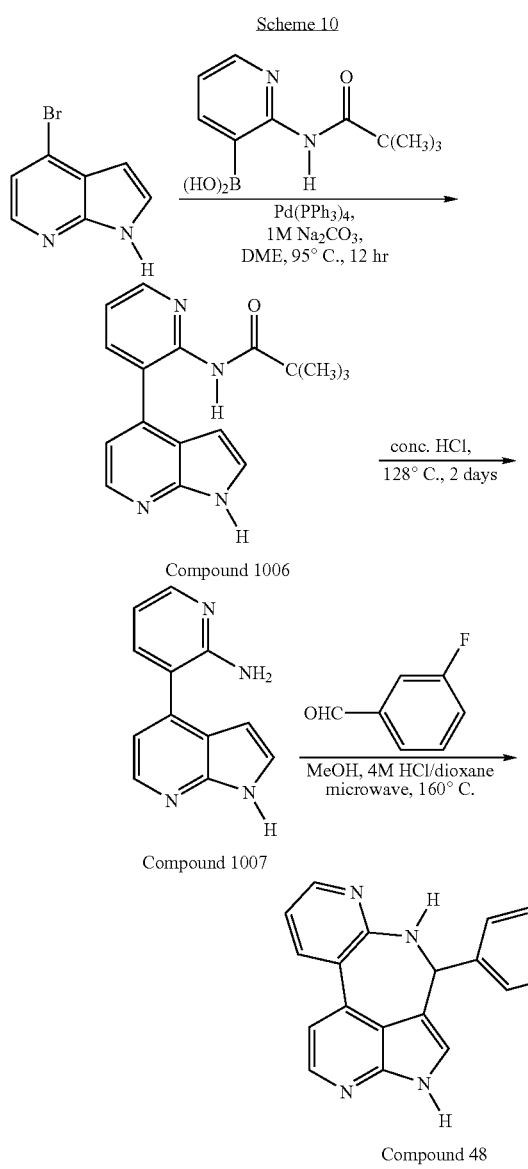

Compound 1006

Compound 1007

Compound 48

Compounds 47, 95, and 97 (see Table 1 for compound structures) were prepared from compound 758545 by varying the aldehyde and using a procedure similar to that for the synthesis of compound 48. Compound 96 was isolated as a by-product during the purification of compound 97.

EXAMPLE 6

Synthesis of Compound 52

As shown in Scheme 11, mCPBA (4.75 g) was added to a solution of 5-chloro-1H-pyrrolo[2,3-b]pyridine (3.00 g) in ethyl acetate (20 mL) at 0° C. The reaction mixture was stirred at room temperature for 12 hours and the solvents removed in vacuo to leave a residue, to which aqueous 30% potassium carbonate was added. Extraction with 10% MeOH/DCM (5×) and evaporation gave the crude N-oxide, which was used directly in the next reaction.

To the N-oxide in DMF at 0° C. (10 mL) was added tetramethyl ammonium bromide (1.00 g) and methylsulfonyl anhydride (1.5 g). The reaction mixture was stirred at 0° C. for 30 minutes and brought to room temperature over 2 hours. Water (40 mL) was added, followed by extraction with dichloromethane (3×) and concentration of the combined organics in vacuo. Silica gel chromatography (0 to 40% EtOAc/DCM) gave 4-bromo-5-chloro-1H-pyrrolo[2,3-b]pyridine, which was contaminated with the corresponding 3-bromo and 3,4-dibromo compounds.

To the mixture of the bromides (0.128 g) in 1,4-dioxane (4 mL) was added 2-acetamidophenylboronic acid (0.20 g), $PdCl_2dppf_2$ (0.04 mg) and potassium phosphate (0.47 g). The reaction mixture was heated at 90° C. overnight. The reaction mixture was cooled and water (20 mL) was added. Extraction with dichloromethane (3×) and concentration of the combined organic extracts gave a mixture of 3- and 4-regional isomers, which were separated by silica gel chromatography (0 to 100% EtOAc/hexane) to produce the 4-isomer (compound 1008, 26 mg) as a pure compound. Compound 1008 was refluxed in concentrated hydrochloric acid for 50 min. Concentration of the reaction mixture in vacuo gave compound 1009.

Compound 1009 (6 mg) was mixed with the 2,6-difluorobenzaldehyde (20 mg) in methanol and 4N HCl-dioxane (0.1 mL). The resulting solution was heated at 95° C. and the progress of the reaction was monitored by LC-MS. When the reaction was judged to be complete, the mixture was concentrated in vacuo and ether was added. Compound 52 was isolated as the HCl salt.

Scheme 11

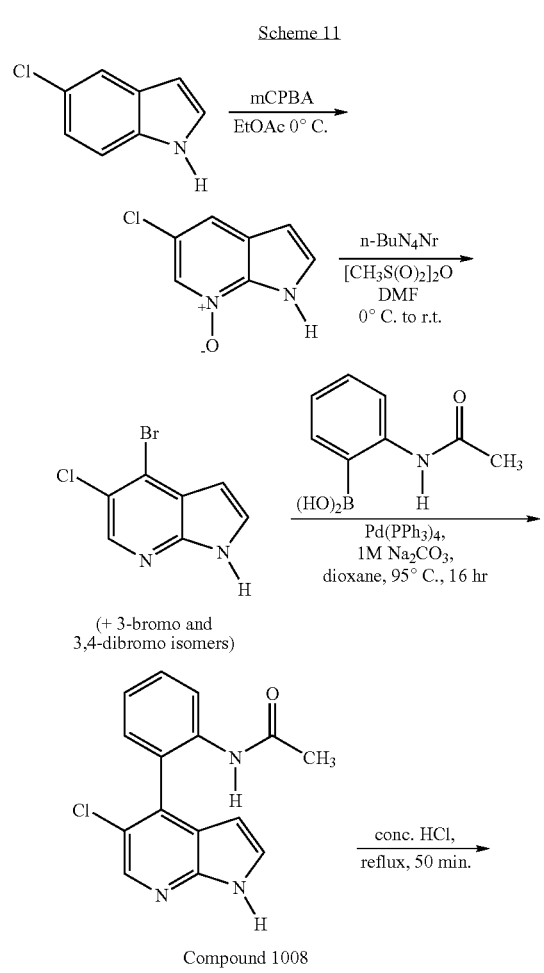

(+ 3-bromo and 3,4-dibromo isomers)

Compound 1008

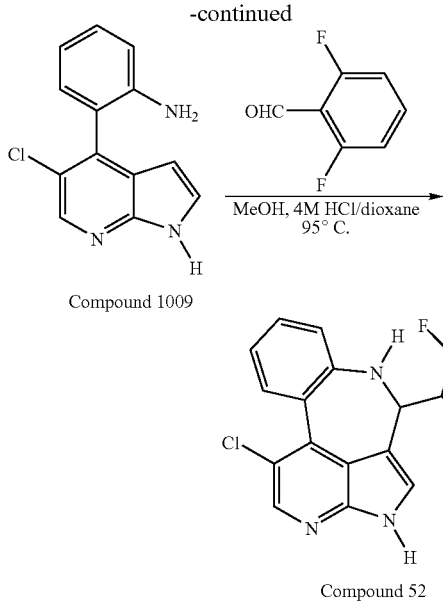

Compound 1009

Compound 52

Compounds 53 and 54 (see Table 1 for compound structures) were prepared from compound 1009 by varying the aldehyde and using a procedure similar to that for the synthesis of compound 52.

EXAMPLE 7

Synthesis of Compound 51

As shown in Scheme 12, a solution of compound 1010 (19 mg) in benzene and $POCl_3$ (0.2 mL) was heated at 90° C. for 2 hours. Additional $POCl_3$ (0.2 mL) was added and heating was continued for and additional 2 hours. Evaporation, addition of saturated sodium bicarbonate, extraction with dichloromethane (3×), and silica gel chromatography (EtOAc) gave compound 51 (7.3 mg).

Scheme 12

Compound 1010

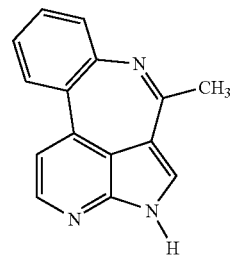

Compound 51

Analytical Characterization

Spectral data for selected compounds of the invention are presented in Table 2. $^1$H-NMR spectra were taken at 500 MHz unless indicated otherwise.

TABLE 2

| Cmpd. No. | ESMS (M + 1) | $^1$H-NMR NMR peaks given as δ values |
|---|---|---|
| 1 | 342.90 | (methanol-$d_4$) 8.40 (d, 1H), 8.16 (d, 1H), 7.89 (d, 1H), 7.59 (s, 1H), 7.54 (dd, 1H), 7.41 (d, 1H), 7.36 (dd, 1H), 7.31-7.27 (m, 5H), 4.99 (dd, 1H), 4.49 (d, 1H), 4.42 (d, 1H), 3.73 (dd, 1H), 3.51 (dd, 1H) |
| 2 | 343.20 | (methanol-$d_4$) 8.90 (s, 1H), 8.18 (d, 1H), 7.88 (d, 1H), 7.57 (dd, 1H), 7.35 (d, 1H), 7.12-6.98 (m, 5 H), 6.25 (dd, 1H), 4.49 (m, 2H), 4.28 (d, 1H), 3.80 (dd, 1H), 3.70 (dd, 1H) |
| 3 | 299.20 | (methanol-$d_4$) 8.93 (s, 1H), 8.32 (d, 1H), 7.94 (d, 1H), 7.61 (dd, 1H), 7.46 (d, 1H), 7.41-7.31 (m, 5H), 7.15 (m, 3H) |
| 4 | 291.20 | (methanol-$d_4$) 9.11 (s, 1H), 8.43 (d, 1H), 7.98 (d, 1H), 7.69 (dd, 1H), 7.59 (d, 1H), 7.18 (d, 1H), 7.07 (dd, 1H) |
| 5 | 297.90 | (methanol-$d_4$) 8.59 (d, 1H), 8.26 (d, 1H), 8.09 (d, 1H), 7.54 (dd, 1H), 7.37-7.33 (m, 8 H), 6.18 (s, 1H) |
| 6 | 278.20 | (methanol-$d_4$) 8.33 (d, 1H), 8.10 (d, 1H), 7.88 (d, 1H), 7.48 (s, 1H), 7.46 (dd, 1H), 7.25 (d, 1H), 7.18 (dd, 1H), 3.64 (s, 1H), 0.89 (s, 9H) |
| 7 | 315.90 | (methanol-$d_4$) 8.46 (d, 1H), 8.14 (d, 1H), 7.97 (d, 1H), 7.40 (dd, 1H), 7.33-7.16 (m, 5H), 7.00 (dd, 1H), 6.90 (dd, 1H), 6.18 (s, 1H), 3.66 (s, 1H) |
| 8 | 294.20 | (methanol-$d_4$) 8.35 (d, 1H), 8.09 (d, 1H), 7.90 (d, 1H), 7.61 (s, 1H), 7.45 (dd, 1H), 7.21 (dd, 1H), 7.19 (dd, 1H), 5.37 (s, 1H), 4.04 (q, 2H), 1.08 (t, 3H) |
| 9 | 328.20 | (methanol-$d_4$) 8.60 (d, 1H), 8.22 (d, 1H), 8.06 (d, 1H), 7.55 (dd, 1H), 7.53-7.31 (m, 4H), 7.12 (d, 1H), 6.74 (m, 2H), 6.48 (s, 1H), 4.03 (s, 3H) |
| 10 | 304.30 | (methanol-$d_4$) 8.36-7.30 (m, 7H), 4.39 (m, 1H), 2.08-0.97 (m, 11H) |
| 11 | 316.20 | (methanol-$d_4$) 8.49-6.99 (m, 11 H), 5.93 (s, 1H), 3.66 (s, 1H) |
| 12 | 316.20 | (methanol-$d_4$) 8.56-7.07 (m, 11 H), 6.13 (s, 1H), 3.66 (s, 1H) |
| 13 | 222.20 | (methanol-$d_4$) 8.49 (d, 1H), 8.28 (d, 1H), 7.97 (d, 1H), 7.67 (s, 1H), 7.65 (d, 1H), 7.58 (dd, 1H), 7.53 (d, 1H), 4.73 (s, 2H) |
| 14 | 250.10 | (methanol-$d_4$) 8.82 (d, 1H), 8.30 (d, 1H), 8.02 (d, 1H), 7.78 (s, 1H), 7.70 (d, 1H), 7.65 (dd, 1H), 7.64 (d, 1H), 4.91 (dd, 1H), 1.90 (m, 1H), 1.60 (m, 1H), 1.08 (t, 3H) |

TABLE 2-continued

| Cmpd. No. | ESMS (M + 1) | ¹H-NMR NMR peaks given as δ values |
|---|---|---|
| 15 | 278.20 | (methanol-$d_4$) 8.52(d, 1H), 8.31 (d, 1H), 8.03 (d, 1H), 7.74 (s, 1H), 7.70 (d, 1H), 7.64 (dd, 1H), 7.60 (d, 1H), 5.08 (dd, 1H), 1.76 (m, 1H), 1.62(m, 1H), 1.37 (m, 1H), 1.03 (d, 3H), 0.92 (d, 3H) |
| 16 | 264.20 | (methanol-$d_4$) 8.37-7.26 (m, 6H), 4.34 (dd, 1H), 1.79 (m, 1H), 1.10 (d, 3H), 0.86 (d, 3H) |
| 17 | 332.00 | (methanol-$d_4$) 8.41 (d, 1H), 8.09 (d, 1H), 7.93 (d, 1H), 7.47 (d, 1H), 7.33 (dd, 1H), 7.24 (dd, 1H), 7.19 (s, 1H), 7.17-7.05 (m, 3H), 6.91 (d, 1H), 6.12 (s, 1H) |
| 18 | 334.00 | (methanol-$d_4$) 8.49 (d, 1H), 8.21 (d, 1H), 8.02 (d, 1H), 7.51 (dd, 1H), 7.49 (dd, 1H), 7.42 (dd, 1H), 7.31 (d, 1H), 7.26 (s, 1H), 7.07 (d, 1H), 7.05 (d, 1H), 6.21 (s, 1H) |
| 19 | 366.10 | (methanol-$d_4$) 8.49 (d, 1H), 8.24 (d, 1H), 8.03 (d, 1H), 7.88 (d, 1H), 7.74 (dd, 1H), 7.65 (s, 1H), 7.64 (d, 1H), 7.52 (dd, 1H), 7.39 (dd, 1H), 7.30 (d, 1H), 6.87 (s, 1H), 5.86 (s, 1H) |
| 20 | 314.20 | (methanol-$d_4$) 8.62-6.61 (m, 10 H), 6.49 (s, 1H) |
| 21 | 375.90 | (methanol-$d_4$) 8.42-6.95 (m, 10 H), 6.07 (s, 1H) |
| 22 | 342.20 | (methanol-$d_4$) 8.45-6.74 (m, 10 H), 5.94 (s, 2 H), 5.75 (s, 1H) |
| 23 | 266.20 | (methanol-$d_4$) 8.41-7.21 (m, 7H), 5.41 (s, 1 H) |
| 24 | 312.20 | (methanol-$d_4$) 8.32 (d, 1H), 8.14 (d, 1H), 7.84 (d, 1H), 7.40 (dd, 1H), 7.29-7.21 (m, 5H), 7.08 (s, 1H), 7.07 (d, 1H), 6.93 (d, 1H), 4.86 (dd, 1H), 3.05 (dd, 1H), 2.97 (dd, 1H) |
| 25 | 334.20 | (methanol-$d_4$) 8.41 (d, 1H), 8.07 (d, 1H), 7.92 (d, 1H), 7.34 (dd, 1H), 7.31 (s, 1H), 7.15 (m, 2H), 7.07 (d, 1H), 6.90 (m, 1H), 6.61 (dd, 1H), 6.08 (s, 1H) |
| 26 | 334.20 | (methanol-$d_4$) 8.40 (dd, 1H), 8.08 (d, 1H), 7.91 (d, 1H), 7.67-7.54 (m, 2H), 7.35 (dd, 1H), 7.26 (s, 1H), 7.17 (dd, 1H), 7.08 (d, 1H), 7.00 (d, 1H), 6.01 (s, 1H) |
| 27 | 334.20 | (methanol-$d_4$) 8.40 (dd, 1H), 8.09 (d, 1H), 7.91 (dd, 1H), 7.34 (dd, 1H), 7.31 (s, 1H), 7.16 (m, 2H), 7.07 (d, 1H), 6.98 (m, 1H), 6.51 (m, 1H), 6.03 (s, 1H) |
| 28 | 334.20 | (methanol-$d_4$) 8.39 (dd, 1H), 8.09 (d, 1H), 7.91 (dd, 1H), 7.37 (dd, 1H), 7.27 (s, 1H), 7.16 (dd, 1H), 7.08 (d, 1H), 6.82 (m, 3H), 5.75 (s, 1H) |
| 29 | 352.10 | (methanol-$d_4$) 8.40 (d, 1H), 8.07 (d, 1H), 7.91 (d, 1H), 7.36 (dd, 1H), 7.33 (s, 1H), 7.16 (dd, 1H), 7.07 (d, 1H), 6.86 (m, 1 H), 6.61 (m, 1H), 6.04 (s, 1H) |
| 30 | 352.10 | (methanol-$d_4$) 8.39 (d, 1H), 8.12 (d, 1H), 7.93 (d, 1H), 7.38 (dd, 1H), 7.30 (m, 1H), 7.26 (s, 1H), 7.22 (dd, 1H), 7.10 (d, 1H), 6.97 (m, 1 H), 6.06 (s, 1H) |
| 31 | 352.10 | (methanol-$d_4$) 8.41 (d, 1H), 8.09 (d, 1H), 7.91 (d, 1H), 7.36 (dd, 1H), 7.33(s, 1H), 7.21 (ddd, 1H), 7.17 (dd, 1H), 7.07 (d, 1H), 6.71 (ddd, 1H), 6.00 (s, 1H) |
| 32 | 350.10 | (methanol-$d_4$) 8.41 (d, 1H), 8.08 (d, 1H), 7.92 (d, 1H), 7.34 (dd, 1H), 7.30 (dd, 1H), 7.22 (s, 1H), 7.16 (dd, 1H), 7.07 (s, 1H), 6.91 (dd, 1H), 6.86 (ddd, 1H), 6.08 (s, 1H) |
| 33 | 350.10 | (methanol-$d_4$) 8.39 (d, 1H), 8.13 (d, 1H), 7.92 (d, 1H), 7.41 (m, 3H), 7.24 (dd, 1H), 7.17 (dd, 1H), 7.08 (dd, 1H), 7.05 (s, 1H), 7.18 (s, 1H) |
| 34 | 384.10 | (methanol-$d_4$) 8.40 (d, 1H), 8.16 (d, 1H), 7.93 (d, 1H), 7.74-7.50 (m, 4 H), 7.27 (dd, 1H), 7.23 (d, 1H), 6.70 (s, 1H), 5.83 (s, 1H) |
| 35 | 343.20 | (methanol-$d_4$) 8.43 (d, 1H), 8.10 (d, 1H), 7.95 (d, 1H), 7.46 (d, 1H), 7.31 (dd, 1H), 7.29 (s, 1H), 7.16 (dd, 1H), 7.06 (d, 1H), 6.96 (d, 1H), 6.16 (s, 1H) |
| 36 | 316.80 | (methanol-$d_4$) 8.39 (d, 1H), 8.03 (d, 1H), 8.01 (d, 1H), 7.81 (d, 1H), 7.33 (s, 1H), 7.28 (dd, 1H), 7.24 (dd, 1H), 7.11 (dd, 1H), 7.03 (d, 1H), 7.02 (dd, 1H), 6.01 (s, 1H) |
| 37 | 298.90 | (methanol-$d_4$) 8.59 (d, 1H), 8.42 (d, 1H), 8.06 (dd, 1H), 7.88 (d, 1H), 7.56 (dd, 1H), 7.50 (d, 1H), 7.38 (s, 1H), 7.33 (dd, 1H), 7.16 (dd, 1H), 7.07 (d, 1H), 6.06 (s, 1H) |
| 38 | 299.20 | (methanol-$d_4$) 8.60 (d, 1H), 8.54 (s, 1H), 8.40 (d, 1H), 8.19 (d, 1H), 8.07 (d, 1H), 7.83 (d, 1H), 7.77 (dd, 1H), 7.31 (dd, 2H), 7.13 (dd, 1H), 7.02 (d, 1H), 5.96 (s, 1H) |
| 39 | 350.10 | (methanol-$d_4$) 8.39 (d, 1H), 8.08 (d, 1H), 7.90 (d, 1H), 7.37 (m, 2H), 7.21 (s, 1H), 7.16 (dd, 1H), 7.10 (d, 1H), 7.07 (d, 1H), 7.04 (d, 1H), 5.72 (s, 1H) |
| 40 | 332.20 | (methanol-$d_4$) 8.39 (d, 1H), 8.10 (d, 1H), 7.90 (d, 1H), 7.64-7.55 (m, 2 H), 7.35 (m, 2 H), 7.27 (s, 2 H), 7.17 (dd, 1H), 7.07 (d, 1H), 5.70 (s, 1H) |
| 41 | 366.00 | (methanol-$d_4$) 8.42 (d, 1H), 8.07 (d, 1H), 7.92 (d, 1H), 7.40 (d, 1H), 7.32 (dd, 1H), 7.29 (s, 1H), 7.14 (dd, 1H), 7.03 (d, 1H), 7.02 (dd, 1H), 6.77 (d, 1H). 6.17(s, 1H) |
| 42 | 366.00 | (methanol-$d_4$) 8.38 (d, 1H), 8.15 (d, 1H), 7.92 (d, 1H), 7.66-7.50 (m, 2 H), 7.44 (d, 1H), 7.42 (dd, 1H), 7.25 (d, 1H), 7.22 (d, 1H), 6.84 (s, 1H), 6.36 (s, 1H) |
| 43 | 299.20 | (methanol-$d_4$) 8.61 (d, 2H), 8.40 (d, 1H), 8.04 (d, 1H), 7.80 (d, 1H), 7.70 (d, 2H), 7.44 (s, 1H), 7.28 (dd, 1H), 7.10 (d, 1H), 6.98 (d, 1H), 6.05 (s, 1H) |

TABLE 2-continued

| Cmpd. No. | ESMS (M + 1) | $^1$H-NMR NMR peaks given as δ values |
|---|---|---|
| 44 | 297.20 | (methanol-d$_4$) 8.88 (d, 2H), 8.29 (d, 1H), 8.11 (m, 1H), 7.86 (m, 3H), 7.58 (d, 1H), 7.46 (dd, 2H), 7.37 (dd, 1H) |
| 45 | 346.20 | (methanol-d$_4$) 8.48 (d, 2H), 8.18 (d, 1H), 7.98 (d, 1 H), 7.46 (dd, 1H), 7.37 (dd, 1H), 7.26 (s, 1H), 7.23 (dd, 1H), 7.05 (m, 3 H), 5.89 (s, 1H), 3.84 (s, 3H) |
| 46 | 348.20 | (methanol-d$_4$) 8.45 (d, 2H), 8.14 (d, 1H), 7.96 (d, 1 H), 7.43 (dd, 1H), 7.31 (dd, 1H), 7.21 (s, 1H), 7.20 (d, 1H), 6.92 (d, 1H), 6.81 (d, 1H), 6.57 (dd, 1H), 6.12 (s, 1H); Lot 3: (d4-MeOH) 6.24 (1H, s), 6.60 (1H, dd), 6.85 (1H, d), 6.95 (1H, d), 7.28 (1H, d), 7.31 (1H, s), 7.41 (1H, dd), 7.50 (1H, dd), 8.02 (1H, d), 8.20 (1H, dd), 8.52 (1H, d) |
| 47 | 335.20 | (methanol-d$_4$) 8.92 (d, 1H), 8.43 (d, 1H), 8.29 (d, 1H), 7.88 (d, 1H), 7.46-7.32 (m, 2H), 7.20 (s, 1H), 7.03 (dd, 2H), 6.38 (s, 1H) |
| 48 | 317.20 | (methanol-d$_4$) 8.83 (d, 1H), 8.42 (d, 1H), 8.29 (d, 1H), 7.82 (d, 1H), 7.35-7.26 (m, 2 H), 7.24 (s, 1H), 7.09 (d, 1 H), 7.02 (m, 2 H), 5.96 (s, 1H) |
| 49 | 335.20 | (CDCl$_3$) 10.41 (s, 1H), 9.00 (s, 1H), 8.75 (d, 1H), 7.34 (dd, 1H), 7.31 (dd, 1H), 7.26 (s, 1H), 7.19 (dd, 1H), 6.97 (dd, 2H), 6.88 (d, 1H), 6.80 (s, 1H), 6.04 (s, 1H) |
| 50 | 317.20 | (methanol-d$_4$) 9.06 (s, 1H), 8.32 (d, 1H), 7.95 (d, 1H), 7.63 (dd, 1H), 7.46 (d, 1H), 7.38 (dd, 1H), 7.27 (s, 1H), 7.20-7.07 (m, 3 H), 7.03 (d, 1H) |
| 51 | 234.20 | (methanol-d$_4$, for free base) 8.13 (d, 1H), 7.99 (d, 1H), 7.98 (s, 1H), 7.42-7.28 (m, 4 H), 2.47 (s, 3H) |
| 52 | 368.10 | (methanol-d$_4$) 8.55 (s, 1H), 8.54 (d, 1 H), 7.74 (dd, 1 H), 7.68-7.56 (mn, 3 H), 7.20 (dd, 2 H), 7.14 (s, 1 H), 6.28 (s, 1 H) |
| 53 | 382.00 | (methanol-d$_4$) 8.50 (s, 1H), 8.41 (d, 1 H), 7.52 (dd, 1 H), 7.46 (dd, 1H), 7.31-7.22 (m, 2 H), 6.95 (dd, 1H), 6.81-6.56 (m, 2H), 6.31(s, 1 H) |
| 54 | 386.10 | (methanol-d$_4$) 8.56 (s, 1H), 8.52 (d, 1 H), 7.70 (dd, 1 H), 7.63 (dd, 1H), 7.54 (m, 2 H), 7.26 (s, 1H), 7.18 (m, 1H), 6.0 (s, 1 H) |
| 55 | 349.20 | (methanol-d$_4$) 8.94 (s, 1H), 8.11 (d, 1H), 7.48 (dd, 1H), 7.27 (s, 1H), 7.21 (dd, 1H), 7.19 (d, 1H), 6.90 (d, 1H), 6.83 (d, 1H), 6.58 (dd, 1H), 6.04 (s, 1H) |
| 56 | 353.10 | (CDCl$_3$) 9.60 (s, 1H), 9.01 (s, 1H), 8.75 (d, 1H), 7.37-6.81 (m, 6H), 6.05 (s, 1H), 4.49 (s, 1H) |
| 57 | 349.20 | (methanol-d$_4$) 8.45 (d, 1H), 8.32 (d, 1H), 8.12 (d, 1H), 7.54 (d, 1H), 7.09 (dd, 1H), 6.96 (s, 1H), 6.86 (d, 1H), 6.77 (d, 1H), 6.51 (d, 1H), 6.02 (s, 1H) |
| 58 | 292.30 | (methanol-d$_4$) 8.70 (s, 1H), 8.29 (d, 1H), 8.12 (d, 1H), 7.58 (d, 1H), 7.48 (m, 2H), 7.41 (d, 1H), 3.68 (t, 2H), 3.03 (t, 2H), 1.97 (m, 2H), 1.77 (m, 2H) |
| 59 | 294.30 | (methanol-d$_4$) 8.33 (d, 1H), 8.14 (d, 1H), 7.80 (d, 1H), 7.48 (dd, 1H), 7.47 (s, 1H), 7.29 (d, 1H), 4.62 (dd, 1H), 3.52 (t, 2 H), 1.76-1.48 (m, 6 H) |
| 60 | 280.30 | (methanol-d$_4$) 8.33 (d, 1H), 8.14 (d, 1H), 7.79 (d, 1H), 7.49 (dd, 1H), 7.48 (s, 1H), 7.30 (d, 1H), 4.65 (dd, 1H), 3.56 (t, 2 H), 1.82-1.64 (m, 4 H) |
| 61 | 348.20 | |
| 62 | 348.20 | |
| 63 | 346.20 | (methanol-d$_4$) 8.31 (d, 1H), 8.12 (d, 1H), 7.82 (s, 1H), 7.60 (d, 1H), 7.56 (d, 1H), 7.48 (m, 2H), 7.32 (m, 1H), 7.11 (s, 1H), 6.99 (d, 1H) |
| 64 | 360.20 | (methanol-d$_4$) 8.39 (d, 1H), 8.14 (d, 1H), 7.83 (d, 1H), 7.41 (dd, 1H), 7.35-6.41 (m, 5 H), 5.61 (s, 1H), 3.66 (s, 3H) |
| 65 | 314.20 | (methanol-d$_4$) 8.59 (d, 1H), 8.28 (d, 1H), 8.09 (d, 1H), 7.62 (dd, 1H), 7.58 (dd, 1H), 7.38 (s, 1H), 7.37 (d, 1H), 7.17 (d, 2H), 6.78 (d, 2H), 6.13, (s, 1H) |
| 66 | 330.20 | (methanol-d$_4$) 8.42 (d, 1H), 8.16 (d, 1H), 7.86 (d, 1H), 7.44 (dd, 1H), 7.36 (dd, 1H), 7.23 (s, 1H), 7.08 (s, 1H), 6.77-6.69 (m, 3H), 5.65 (s, 1H) |
| 67 | 382.00 | (methanol-d$_4$) 8.39 (d, 1H), 8.11 (d, 1H), 7.90 (d, 1H), 7.39 (dd, 1H), 7.22-7.10 (m, 3 H), 7.17 (s, 2H), 5.61 (s, 1H) |
| 68 | 362.20 | (methanol-d$_4$) 8.43 (d, 1H), 8.16 (d, 1H), 7.93(d, 1H), 7.44 (dd, 1H), 7.31 (dd, 1H), 7.20 (d, 1H), 7.20 (s, 1H), 6.77 (s, 1H), 6.60 (d, 1H), 5.73 (s, 1H), 3.77 (s, 3H) |
| 69 | 330.20 | (methanol-d$_4$) 8.61 (d, 1H), 8.25 (d, 1H), 8.07(d, 1H), 7.64(dd, 1H), 7.58 (dd, 1H), 7.53 (d, 1H), 7.52 (dd, 1H), 6.80 (d, 1H), 6.50 (dd, 1H), 6.48 (s, 1H), 6.21 (br s, 1H) |
| 70 | 378.10 | (methanol-d$_4$) 8.41 (d, 1H), 8.09 (d, 1H), 7.90 (d, 1H), 7.36 (dd, 1H), 7.22 (s, 1H), 7.21 (d, 1H), 7.10 (d, 1H), 6.66 (d, 1H), 6.34 (d, 1H), 6.10 (s, 1H), 3.83 (s, 3H) |
| 71 | 359.10 | (methanol-d$_4$) 8.44 (d, 1H), 8.10 (d, 1H), 8.04 (d, 1H), 7.96 (d, 1H), 7.40 (s, 1H), 7.32 (dd, 1H), 7.18 (dd, 1H), 6.92 (d, 1H), 6.72 (dd, 1H), 6.46 (s, 1H), 6.28 (d, 1H) |
| 72 | 330.20 | (methanol-d$_4$) 8.61 (d, 1H), 8.25 (d, 1H), 8.06 (d, 1H), 7.62 (dd, 1H), 7.60 (dd, 1H), 7.56 (dd, 1H), 7.50 (d, 1H), 6.76 (d, 1H), 6.62 (d, 1H), 6.43 (s, 1H), 6.10 (s, 1H) |

TABLE 2-continued

| Cmpd. No. | ESMS (M + 1) | ¹H-NMR NMR peaks given as δ values |
|---|---|---|
| 73 | 344.20 | (methanol-d₄) 8.57 (d, 1H), 8.27 (d, 1H), 8.06 (d, 1H), 7.58 (m, 2H), 7.38 (d, 1H), 7.36 (s, 1H), 6.97 (s, 1H), 6.77 (m, 2H), 6.07 (s, 1H), 3.77 (s, 3H) |
| 74 | 348.20 | (methanol-d₄) 8.50 (d, 1H), 8.20 (d, 1H), 7.99 (d, 1H), 7.50 (dd, 1H), 7.42 (dd, 1H), 7.26 (m, 3H), 7.09 (d, 1H), 6.88 (d, 1H), 5.88 (s, 1H) |
| 75 | 440.10 | (methanol-d₄) 8.51 (d, 1H), 8.22 (d, 1H), 8.01 (d, 1H), 7.65 (s, 1H), 7.51 (dd, 1H), 7.45 (dd, 1H), 7.28 (d, 1H), 7.26 (s, 1H), 7.15 (d, 1H), 6.80 (d, 1H), 5.88 (s, 1H) |
| 76 | 422.10 | (methanol-d₄) 8.40 (d, 1H), 8.13 (d, 1H), 7.90 (d, 1H), 7.66-7.07 (m, 4H), 7.04 (s, 1H), 6.65 (s, 1H), 5.92 (s, 1H), 3.56 (s, 3H) |
| 77 | 392.00 | (methanol-d₄) 8.38 (d, 1H), 8.10 (d, 1H), 7.87 (d, 1H), 7.66-7.10 (m, 6H), 6.85 (d, 1H), 5.60 (s, 1H) |
| 78 | 469.90 | (methanol-d₄) 8.38 (d, 1H), 8.10 (d, 1H), 7.87 (d, 1H), 7.66-7.10 (m, 5H), 6.85 (d, 1H), 5.60 (s, 1H) |
| 79 | 342.20 | (methanol-d₄) 8.41 (d, 1H), 8.17 (d, 1H), 7.85 (d, 1H), 7.66-6.91 (m, H), 5.61 (s, 1H), 2.18 (s, 6H) |
| 80 | 332.30 | (methanol-d₄) 8.40 (d, 1H), 8.10 (d, 1H), 7.82 (d, 1H), 7.53-7.09 (m, 5H), 6.53 (s, 1H) |
| 81 | 349.20 | (methanol-d₄) 8.92 (s, 1H), 8.09 (d, 1H), 7.50 (dd, 1H), 7.25 (s, 2H), 7.21 (d, 1H), 7.06 (d, 1H), 6.86 (d, 1H), 5.62 (s, 1H) |
| 82 | 393.00 | (methanol-d₄) 8.80 (s, 1H), 8.53 (d, 1H), 7.44 (s, 1H), 7.29 (dd, 1H), 7.10 (dd, 1H), 7.08 (d, 1H), 7.04 (d, 1H), 6.83 (d, 1H), 6.82 (s, 1H), 5.43 (s, 1H) |
| 83 | 329.20 | (methanol-d₄) 8.88 (s, 1H), 8.19 (d, 1H), 7.45 (dd, 1H), 7.19 (m, 2H), 7.08 (s, 1H), 7.03 (s, 1H), 6.98 (d, 1H), 6.72 (d, 1H), 5.49 (s, 1H), 2.10 (s, 3H) |
| 84 | 345.20 | (methanol-d₄) 8.92 (s, 1H), 8.11 (d, 1H), 7.50 (dd, 1H), 7.24 (d, 1H), 7.20 (s, 2H), 6.96 (s, 1H), 6.75 (d, 1H), 6.70 (d, 1H), 5.60 (s, 1H), 3.79 (s, 3H) |
| 85 | 375.20 | (methanol-d₄) 8.92 (s, 1H), 8.13 (d, 1H), 7.51 (dd, 1H), 7.25 (d, 1H), 7.23 (s, 1H), 7.21 (d, 1H),. 6.63 (s, 2H), 5.60 (s, 1H), 3.75 (s, 6H) |
| 86 | 342.70 | (methanol-d₄) 8.43 (d, 1H), 8.12 (d, 2H), 8.10 (d, 1H), 7.94 (d, 1H), 7.46 (d, 2H), 7.35 (dd, 1H), 7.29 (s, 1H), 7.17 (dd, 1H), 7.09 (d, 1H), 5.93 (s, 1H) |
| 87 | 356.10 | (methanol-d₄) 8.43 (d, 1H), 8.12 (d, 1H), 7.94 (dd, 1H), 7.93 (d, 2H), 7.38 (dd, 1H), 7.36 (d, 2H), 7.22 (s, 1H), 7.21 (d, 1H), 7.12 (d, 1H), 5.88 (s, 1H), 3.87 (s, 3H) |
| 88 | 342.20 | (D₂O) 8.46 (d, 1H), 8.08 (d, 1H), 7.92 (d, 1H), 7.89 (d, 2H), 7.46 (dd, 1H), 7.38 (dd, 1H), 7.33 (s, 1H), 7.27 (d, 2H), 7.15 (s, 1H), 5.95 (s, 1H) |
| 89 | 438.90 | (methanol-d₄) 8.44-7.25 (m, 12 H), 5.07 (s, 2H), 4.60 and 4.51 (2 br s, 1H), 4.14 and 4.03 (2d, 2H), 2.75-1.28 (m, 7H) |
| 90 | 305.30 | (methanol-d₄) 8.31 (br s, 1H), 8.10 (d, 1H), 7.75 (br s, 1H), 7.40 (m, 3H), 7.17 (d, 1H), 7.12 (dd, 1H), 4.31 (br s, 1H), 3.38 (dd, 2H), 2.71 (m, 2H), 2.21 (d, 1H), 1.72 (m, 2H), 1.58 (m, 2H) |
| 91 | 355.20 | (CDCl₃) 8.73 (s, 1H), 8.39 (d, 1H), 8.01 (d, 1H), 7.80 (d, 2H), 7.49 (d, 2H), 7.46 (d, 1H), 7.24 (dd, 1H), 7.15 (dd, 1H), 6.87 (d, 1H), 6.47 (s, 1H), 6.12 (br s, 1H), 5.47 (s, 1H), 3.05 (d, 3H) |
| 92 | 313.20 | (methanol-d₄) 8.90 (d, 1H), 8.85 (s, 1H), 8.21 (s, 1H), 7.82 (d, 2H), 7.63 (dd, 1 H), 7.57 (m, 2 H), 7.10 (d, 2 H) |
| 93 | 313.20 | (methanol-d₄) 8.25 (d, 1H), 7.95 (d, 1H), 7.48 (d, 1H), 7.21 (dd, 1H), 7.11 (d, 2H), 7.10 (dd, 1H), 7.03 (d, 1H), 6.70 (d, 2H), 6.65 (s, 1H), 5.27 (s, 1H) |
| 94 | 310.80 | (methanol-d₄) 8.31 (d, 1H), 8.12 (s, 1H), 8.07 (d, 1H), 7.62 (d, 1H), 7.61 (d, 2H), 7.50-7.42 (m, 2H), 7.39 (dd, 1H), 6.85 (d, 2H) |
| 95 | 362.80 | (methanol-d₄) 8.65 (d, J = 8.0 Hz, 1 H), 8.49 (d, J = 6.8 Hz, 1 H), 8.35 (d, J = 4.6 Hz, 1 H), 7.96 (d, J = 6.8 Hz, 2 H), 7.36 (s, 1 H), 7.20-7.18 (m, 2 H), 7.05 (dd, J = 8.4, 2.0 Hz, 1 H), 6.83 (d, J = 8.4 Hz, 1 H), 5.80 (s, 1 H), 4.41 (s, 3 H) |
| 96 | 328.80 | (methanol-d₄) 8.60 (d, 1H), 8.46 (d, 1H), 8.33 (d, 1H), 7.94 (d, 2 H), 7.20 (s, 1H), 7.16 (dd, 1H), 7.14 (d, 2H), 6.74 (d, 2H), 5.71 (s, 1H), 4.39 (s, 3 H) |
| 97 | 314.80 | (methanol-d₄) 8.94 (dd, J = 8.0, 1.4 Hz, 1 H), 8.41 (d, J = 5.9 Hz, 1 H), 8.28 (dd, J = 5.5, 1.6 Hz, 1 H), 7.81 (d, J = 6.0 Hz, 1 H), 7.33 (dd, J = 8.0, 5.5 Hz, 1 H), 7.19 (d, J = Hz, 2 H), 7.04 (s, 1 H), 6.80 (d, J = Hz, 2H), 5.80 (s, 1 H) |
| 98 | 400.80 | (methanol-d₄) 8.42 (d, J = 6.6 Hz, 1 H), 8.13 (d, J = 8.9 Hz, 2 H), 8.00 (d, J = 8.1 Hz, 1 H), 7.90 (d, J = 6.6 Hz, 1 H), 7.47 (d, J = 8.9 Hz, 2 H), 7.41-7.38 (m, 1 H), 7.34 (s, 1 H), 7.28 (d, J = 8.1 Hz, 1 H), 7.14 (t, J = 7.1 Hz, 1 H), 3.80 (s, 3 H) |
| 99 | 371.50 | (CDCl₃) 8.82 (s, 1 H), 8.38 (d, J = 5.1 Hz, 1 H), 8.01 (d, J = 8.0 Hz, 1 H), 7.51-7.39 (m, 4 H), 7.20 (s, 1 H), 7.16-7.13 (m, 1 H), 6.89 (d, J = 7.9 Hz, 1 H), 6.73 (s, 1 H), 6.68 (s, 1 H), 6.49 (s, 1 H), 5.50 (s, 1 H), 5.36 (s, 1 H), 3.71 (s, 3 H) |

TABLE 2-continued

| Cmpd. No. | ESMS (M + 1) | $^1$H-NMR NMR peaks given as δ values |
|---|---|---|
| 100 | 429.50 | (methanol-d$_4$) 8.48 (d, 1 H), 8.07 (d, 1 H), 7.96 (d, 1 H), 7.43 (d, 2 H), 7.34 (dd, 1 H), 7.26 (s, 1H), 7.23 (d, 2 H), 7.18 (dd, 1 H), 7.13 (d, 1 H), 5.50 (s, 1 H), 4.10 (s, 3 H), 3.73 (s, 3 H) |
| 101 | 487.50 | (methanol-d$_4$) 8.50-7.04 (m, 11 H), 5.68 (s, 1 H), 4.14 (s, 3 H), 4.08 (s, 3 H), 3.67 (s, 3 H) |
| 102 | 370.90 | (CDCl$_3$) 9.58 (s, 1 H), 8.29 (d, J = 5.3 Hz, 1 H), 7.78 (d, J = 7.8 Hz, 1 H), 7.33 (d, J = 5.3 Hz, 1 H), 7.12 (t, J = 7.2 Hz, 1 H), 7.02 (s, 1 H), 6.98 (d, J = 8.5 Hz, , 2 H), 6.84 (d, J = 7.9 Hz, 1 H), 6.46 (d, J = 8.5 Hz, 2 H), 5.29 (s, 1 H), 3.70 (d, J = 4.0 Hz, H), 3.66 (s, 3 H), 3.55 (br s, 2H) |
| 103 | 372.50 | (methanol-d$_4$) 8.37 (d, J = 6.6 Hz, H), 8.02 (d, J = 8.1 Hz, H), 7.88 (d, J = 6.7 Hz, H), 7.40(dd, J= 7.6 Hz, 1H), 7.26 (d, J = 7.9 Hz, 1H), 7.16 (dd, J = 7.9 Hz, 1H), 7.14 (s, 1H), 7.06 (dd, J = 1.9, 6.8 Hz, 2 H), 6.71 (d, J = 6.8 Hz, 2 H), 3.70 (s, 3 H) |
| 104 | 382.40 | (methanol-d$_4$) 8.39 (d, J = 6.4 Hz, 1 H), 8.12-8.11 (m, 1 H), 7.87 (d, J = 6.5 Hz, 1 H), 7.45 (d, J = 2.0 Hz, 1 H), 7.39 (dd, J = 6.6 and 1.2 Hz, , 1 H), 7.31 (dd, J = 2.1, 8.5 Hz, 1 H), 7.22 (ddd, J = 8, 8 and 0.9 Hz, 1 H), 7.13 (dd, J = 0.9, 8.1 Hz, 1 H), 7.05 (s, 1 H), 6.90 (d, J = 8.5 Hz, 1 H), 5.65 (s, 1 H) |
| 105 | 332.40 | (methanol-d$_4$) 8.58 (d, J = 6.4 Hz, 1 H), 8.26 (dd, J = 3.4, 6.0 Hz, 1 H), 8.08 (d, J = 6.5 Hz, 1 H), 7.55 (m, 2 H), 7.42 (s, 1 H), 7.35 (dd, J = 3.4, 5.9 Hz, 1 H), 7.04 (dd, J = 1.9, 11.7 Hz, 1 H), 6.97 (d, J = 8.4 Hz, 1 H), 6.89 (dd, J = 7.9 and 7.9 Hz, H), 6.12 (s, 1 H) |
| 106 | 350.40 | (methanol-d$_4$) 8.41 (d, J = 6.5 Hz, 1 H), 8.12 (d, J = 8.0 Hz, 1 H), 7.92 (d, J = 6.5 Hz, 1 H), 7.41 (dd, J = 8 and 8 Hz, 1 H), 7.23 (d, J = 6.0 Hz, 2 H), 7.14 (d, J = 8.1 Hz, 1 H), 6.81 (d, J = 8.8 Hz, 2 H), 5.70 (s, 1 H) |
| 107 | 332.40 | (methanol-d$_4$) 8.60 (d, 1 H), 8.27 (d, 1 H), 8.10 (d, 1 H), 7.64-7.57 (m, 2 H), 7.49 (s, 1 H), 7.42-7.39 (m, 1 H), 6.81 (dd, 1 H), 6.64 (dd, 1 H), 6.48 (dd, 1 H), 6.36 (s, 1 H) |
| 108 | 426.50 | (methanol-d$_4$) 8.61 (d, J = 6.2 Hz, 1 H), 8.30 (d, J = 7.9 Hz, 1 H), 8.08 (d, J = 6.2 Hz, 1 H), 7.63 (d, J = 7.7 Hz, 1 H), 7.56 (d, J = 7.6 Hz, 1 H), 7.42 (s, 1 H), 7.29 (d, J = 7.7 Hz, 1 H), 7.12 (s, 1 H), 6.17 (s, 1 H), 1.33 (s, 18 H) |
| 109 | 220.30 | (methanol-d$_4$) 8.39 (s, 1 H), 8.26 (d, J = 5.4 Hz, 1 H), 8.22 (s, 1 H), 8.10-8.08 (m, 1 H), 7.52 (d, J = 5.5 Hz, 1 H), 7.47-7.44 (m, 2H), 7.18-7.16 (m, 1 H) |
| 110 | 358.40 | (methanol-d$_4$) 8.40 (d, H), 8.11 (d, 1 H), 7.87 (d, 1, H), 7.80 (s, 1H), 7.43-7.36 (m, 2 H), 7.22 (dd, 1 H), 7.14 (d, 1 H), 7.07 (s, 1 H), 6.90 (d, 1 H), 5.66 (s, 1 H) |
| 111 | 372.50 | (methanol-d$_4$) 8.39 (d, J = 6.4 Hz, 1 H), 8.11 (d, J = 8.1 Hz, 1 H), 7.88 (d, J = 6.5 Hz, 1 H), 7.80 (d, J = 2.3 Hz, 1 H), 7.44 (dd, J = 2.3, 8.6 Hz, 1 H), 7.38 (dd, J = 9 and 9 Hz, 1 H), 7.22 (dd, J = 9.1 and 9.1 Hz, H), 7.13 (d, J = 8.0 Hz, 1 H), 7.06 (s, 1 H), 6.93 (d, J = 8.6 Hz, 1 H), 5.65 (s, 1 H), 3.89 (s, 3 H) |
| 112 | 378.40 | (methanol-d$_4$) 8.39 (d, 1 H), 8.11 (d, 1 H), 7.87 (d, 1 H), 7.41-7.36 (m, 1 H), 7.24 (dd, 1 H), 7.14 (d, 1 H), 7.13 (s, 1H), 6.86 (d, 1 H), 6.79 (d, 1 H), 5.62 (s, 1 H), 3.77 (s, 3 H) |
| 113 | 396.40 | (methanol-d$_4$) 8.31 (d, J = 5.4 Hz, 1 H), 8.10 (dd, J = 4.8 Hz, 1 H), 7.98 (s, 1 H), 7.80 (d, J = 0.9 Hz, 1 H), 7.70 (dd, J = 2.3, 8.5 Hz, 1 H), 7.61 (d, J = 5.5 Hz, 1 H), 7.48-7.36 (m, 3 H), 7.25 (d, J = 8.5 Hz, 1 H) |
| 114 | 398.40 | (methanol-d$_4$) 8.39 (d, J = 5.9 Hz, 1 H), 8.10 (d, J = 7.2 Hz, 1 H), 7.87 (d, J = 6.4 Hz, 1 H), 7.37-7.07 (m, 6 H), 6.90 (d, J = 8.4 Hz, 1 H), 5.67 (s, 1 H) |
| 115 | 351.30 | (methanol-d$_4$) 8.90 (s, 1H), 8.14 (d, 1H), 7.47 (dd, 1H), 7.30 (s, 1H), 7.18 (dd, 1H), 7.16 (d, 1H), 6.81 (d, 2H), 5.65 (s, 1H) |
| 116 | 333.30 | (methanol-d$_4$) 8.91 (s, 1 H), 8.10 (d, J = 8.3 Hz, 1 H), 7.48 (t, J = 7.6 Hz, 1 H), 7.24 (s, 1 H), 7.20-7.18 (m, 2 H), 7.00 (d, J = 12.0 Hz, 1 H), 6.91 (d, J = 8.3 Hz, 1 H), 6.86 (t, J = 8.5 Hz, 1 H), 5.62 (s, 1 H) |
| 117 | 347.30 | (methanol-d$_4$) 9.03 (s, 1H), 8.72 (d, 1H), 7.41 (dd, 1H), 7.19 (d, 1H), 7.08 (d, 1H), 7.07 (dd, 1H), 6.99 (d, 1H), 6.92 (d, 1H), 6.85 (dd, 1H), 5.63 (s, 1H), 4.30 (s, 3H) |
| 118 | 333.30 | (methanol-d$_4$) 8.94 (s, 1 H), 8.07 (dd, 1H), 7.49 (ddd, 1H), 7.33 (s, 1H), 7.21 (dd, 1H), 7.20 (d, 1H), 6.78 (dd, 1H), 6.57 (dd, 1H), 6.45 (dd, 1H), 5.94 (s, 1H) |
| 119 | 364.30 | |
| 120 | 365.30 | (DMSO-d$_6$) 12.00 (s, H), 11.96 (s, H), 9.20 (s, H), 8.36 (d, J = 5.7 Hz, H), 8.18 (s, H), 8.00 (d, J = 7.8 Hz, H), 7.72 (d, J = 8.4 Hz, H), 7.65 (s, H), 7.61 (d, J = 5.6 Hz, 2H), 7.53 (d, J = 8.5 Hz, 2H), 7.22-7.17 (m, H), 7.09 (d, J = 8.0 Hz, H), 5.75 (s, H). |
| 121 | 376.30 | (DMSO-d$_6$) 11.82 (s, H), 10.14 (s, H), 8.33 (d, J = 5.5 Hz, H), 8.16 (s, H), 7.97 (d, J = 8.1 Hz, H), 7.79 (d, J = 8.3 Hz, 2H), 7.55 (d, J = 5.7 Hz, H), 7.45-7.41 (m, 2H), 7.19-7.16 (m, H), 7.04 (d, J = 8.0 Hz, H), 7.00-6.97 (m, H), 5.74 (s, H), 3.14 (s, 3H). |

TABLE 2-continued

| Cmpd. No. | ESMS (M + 1) | ¹H-NMR NMR peaks given as δ values |
|---|---|---|
| 122 | 315.20 | |
| 123 | 391.30 | (DMSO-d₆) 11.89 (s, H), 9.66 (s, H), 8.35 (d, J = 5.6 Hz, H), 8.00 (d, J = 7.9 Hz, 2H), 7.59 (d, J = 5.6 Hz, 2H), 7.23-7.21 (m, H), 7.17 (d, J = 8.3 Hz, H), 7.12 (s, H), 7.09 (d, J = 8.4 Hz, H), 7.03 (s, H), 5.61 (s, H), 3.17 (s, 3H). |
| 124 | 332.20 | (DMSO-d₆) 11.92 (s, H), 11.87 (s, H), 8.32 (d, J = 5.7 Hz, H), 7.98 (d, J = 8.0 Hz, H), 7.56 (d, J = 5.6 Hz, H), 7.36 (s, H), 7.25-7.22 (m, H), 7.09 (d, J = 7.9 Hz, H), 7.02 (t, J = 7.5 Hz, H), 6.43 (s, H), 5.81 (s, H), 2.23 (s, 3H), 1.91 (s, 3H) |
| 125 | 342.40 | (methanol-d₄) 8.41 (d, J = 5.8 Hz, 1 H), 7.76-7.72 (m, 1 H), 7.67-7.65 (m, 2 H), 7.44 (d, = 8.5 Hz, 2 H), 7.42-7.38 (m, 2 H), 7.12 (d, J = 1.0 Hz, 1 H), 6.81 (d, J = 8.5 Hz, 2 H), 5.25 (s, 1 H) |
| 126 | 356.10 | |
| 127 | 360.10 | |
| 128 | 342.40 | (methanol-d₄) 8.53 (d, J = 6.1 Hz, 1 H), 8.21 (d, J = 7.8 Hz, 1 H), 8.03 (d, J = 6.3 Hz, 1 H), 7.67-7.27 (m, 8 H), 6.04 (s, 1 H) |
| 129 | 370.10 | (methanol-d₄) 8.39 (d, H), 7.77-7.64 (m, 3H), 7.53 (d, H), 7.37 (d, H), 7.28 (m, 2H), 6.96 (d, H), 6.76 (s, H), 5.95 (s, H), 4.88 (s, H), 4.72 (s, H), 3.87 (s, 3H), 2.21 (s, 3H). |
| 130 | 418.40 | (methanol-d₄) 8.25 (d, 1 H), 7.83 (d, 1 H), 7.41 (d, 1 H), 7.37-6.85 (m, 7 H), 4.27-4.15 (m, 2 H), 3.74 (s, 3 H), 1.15 (t, 3 H) |
| 131 | 438.10 | (DMSO-d₆) 11.90 (s, H), 8.35 (d, J = 5.6 Hz, H), 7.98 (d, J = 7.9 Hz, H), 7.71-7.57 (m, H), 7.51-7.46 (m, 2H), 7.39-7.32 (m, 2H), 7.22-7.15 (m, 2H), 7.10-7.07 (m, 2H), 7.03-7.00 (m, H), 6.85 (d, J = 6.6 Hz, 2H), 6.78 (d, J = 7.6 Hz, H), 5.66 (s, H). |
| 132 | 418.10 | (DMSO-d₆) 11.92 (s, H), 8.37 (d, J = 5.6 Hz, H), 8.00 (d, J = 7.8 Hz, H), 7.61 (d, J = 5.5 Hz, H), 7.39 (d, J = 7.3 Hz, 2H), 7.30-6.95 (m, 8H), 6.73 (s, 2H), 6.04 (s, H), 2.30 (s, 3H), 2.12 (s, 2H). |
| 133 | 328.10 | (DMSO-d₆) 11.99 (s, H), 8.39 (m, H), 8.08 (d, H), 7.68 (d, H), 7.36-7.09 (m, 3H), 6.92-6.73 (m, 2H), 6.65 (s, H), 6.50 (s, H), 2.35 (s, 3H). |
| 134 | 382.10 | |
| 135 | 328.10 | (DMSO-d₆) 11.96 (s, H), 8.37 (d, J = 5.6 Hz, H), 8.02 (d, J = 7.9 Hz, H), 7.64 (dd, J = 5.7, 16.8 Hz, H), 7.26-7.22 (m, 2H), 6.82 (d, J = 8.4 Hz, 2H), 5.66 (s, H), 3.69 (s, 3H). |
| 136 | 366.10 | (DMSO-d₆) 11.91 (s, H), 8.35 (d, J = 5.6 Hz, H), 7.98 (d, J = 8.1 Hz, H), 7.61-7.57 (m, 3H), 7.38 (d, J = 8.0 Hz, 2H), 7.22-7.14 (m, 2H), 6.99 (t, J = 7.5 Hz, 2H), 6.86 (s, br, H), 5.75 (s, H). |
| 137 | 312.10 | (DMSO-d₆) 12.04 (s, H), 8.38 (d, J = 5.7 Hz, H), 8.03 (t, J = 8.0 Hz, H), 7.64 (d, J = 5.8 Hz, H), 7.33-6.99 (9H), 5.68 (s, H), 2.23 (s, 3H). |
| 138 | 330.40 | |
| 139 | 359.40 | |
| 140 | 328.40 | |
| 141 | 340.40 | |
| 142 | 358.40 | |
| 143 | 415.40 | |
| 144 | 356.40 | |
| 145 | 356.40 | |
| 146 | 356.40 | |
| 147 | 390.40 | |
| 148 | 358.10 | |
| 149 | 378.10 | |
| 150 | 360.30 | (methanol-d₄) 8.39 (d, 1H), 7.71 (dd, 1H), 7.64 (d, 1H), 7.65 (d, 1H), 7.58 (d, 1H), 7.41 (dd, 1H), 7.33 (d, 1H), 7.13 (d, 1H), 7.06 (s, 1H), 6.91 (dd, 1H), 5.27 (s, 1H) |
| 151 | 401.40 | (methanol-d₄) 8.93 (s, 1 H), 8.02 (d, 1 H), 7.55 (dd, 1H), 7.43 (d, 1H), 7.40 (s, 1H), 7.22 (dd, 1H), 7.18 (d, 2H), 6.86 (d, 2H), 4.23 (q, 2H), 3.65 (s, 3 H), 1.14 (t, 3H) |
| 152 | 403.90 | |
| 153 | 375.90 | |
| 154 | 328.00 | |
| 155 | 261.00 | |
| 156 | 294.00 | |
| 157 | 413.10 | |
| 158 | 342.90 | (methanol-d₄) 8.92 (s, 1H); 7.88 (d, 1H); 7.80 (dd, 1H); 7.72 (dd, 1H); 7.50 (d, 1H); 7.42 (d, 2H); 7.20 (s, 1H); 6.82 (d, 2H); 5.15 (s, 1H) |
| 159 | 357.00 | (methanol-d₄) 8.90 (s, 1H); 7.88 (d, 1H); 7.82 (dd, 1H); 7.75 (dd, 1H); 7.62 (d, 1H); 7.42 (d, 2H); 7.15 (s, 1H); 7.78 (d, 2H); 5.22 (s, 1H); 3.15 (s, 3H) |
| 160 | 361.30 | (DMSO-d₆) 12.35 ppm (bs, 0.5H), 12.1 (bs, 0.5H), 8.9 (s, 0.5H), 8.85 (s, 0.5H), 7.9 (dd, 0.5H), 7.8 (s, 0.5H), 7.5 to 7.65 (m, 3H), 7.3 (dd, 0.5H), 7.1 to 7.2 (m, 2H), 6.85 to 6.95 (m, 1.5H), 6.7 (dd, 0.5H), 6.5 (t, 0.5H), 6.25 to 6.4 (m, 1H), 5.1 (s, 0.5H), 5.05 (s, 0.5H). |

TABLE 2-continued

| Cmpd. No. | ESMS (M + 1) | 1H-NMR NMR peaks given as δ values |
|---|---|---|
| 161 | 341.30 | (DMSO-d$_6$) 12.3 ppm (bs, 0.63H), 12.1 (bs, 0.37H), 9.55 (s, 0.37H), 9.35 (s, 0.63H), 8.9 (s, 1H), 7.9 (dd, 0.37H), 7.75 (d, 0.63H), 7.6 (m, 1H), 7.5 (t, 2H), 7.3 (dd, 0.37H), 7.0 to 7.2 (m, 2H), 6.9 (s, 0.37H), 6.5 to 6.7 (m, 2.25H), 5.15 (s, 1H), 2.35 (s, 1.13H), 2.0 (s, 1.9H). |
| 162 | 465.30 | (DMSO-d$_6$, 300 MHz) 12.75 (s, 1H), 8.46 (d, J = 11 Hz, 1H), 8.06 (d, J = 12.5 Hz, 1H), 7.82 (d, J = 11 Hz, 1H), 7.41 (m, 6H), 7.30 (m, 2H), 7.19 (m, 2H), 7.11 (m, 2H), 6.93 (d, J = 14 Hz, 1H), 5.89 (s, 1H), 3.31 (br s, 3H). |

EXAMPLE 8

JAK-3 Inhibition Assay

Compounds were screened for their ability to inhibit JAK using the assay shown below. Reactions were carried out in a kinase buffer containing 100 mM HEPES (pH 7.4), 1 mM DTT, 10 mM MgCl$_2$, 25 mM NaCl, and 0.01% BSA.

Substrate concentrations in the assay were 5 µM ATP (200 µCi/µmole ATP) and 1 µM poly(Glu)$_4$Tyr. Reactions were carried out at 25° C. and 1 nM JAK-3.

To each well of a 96 well polycarbonate plate was added 1.5 µL of a candidate JAK-3 inhibitor along with 50 µL of kinase buffer containing 2 µM poly(Glu)$_4$Tyr and 10 µM ATP. This was then mixed and 50 µL of kinase buffer containing 2 nM JAK-3 enzyme was added to start the reaction. After 20 minutes at room temperature (25° C.), the reaction was stopped with 50 µL of 20% trichloroacetic acid (TCA) that also contained 0.4 mM ATP. The entire contents of each well were then transferred to a 96 well glass fiber filter plate using a TomTek Cell Harvester. After washing, 60 µL of scintillation fluid was added and $^{33}$P incorporation detected on a Perkin Elmer TopCount. After removing the mean background values for all of the data points, the data were fit using Prism software to obtain a K$_i$ value (app).

EXAMPLE 9

JAK-2 Inhibition Assay

The JAK-2 assays were performed as described above in Example 8 except that JAK-2 enzyme was used, the final poly(Glu)$_4$Tyr concentration was 15 µM, and final ATP concentration was 12 µM. Selected results are presented in Table 1.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

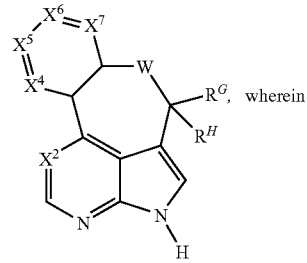

(I-a)

wherein

W is —N(R$^F$)-, —C(X)N(R$^F$)- or —N(R$^F$)C(X)-;

X is O, S, [hydrogen, hydrogen] or [hydrogen, R];

X$^2$ is N or C—R$^{X2}$, wherein R$^{X2}$ is hydrogen, halogen, —CN, —NO$_2$, —OR$^{X2B}$, —OC(O)R$^{X2B}$, —OC(O)OR$^{X2B}$, —OC(O)NR$^{X2A}$R$^{X2B}$, —OC(S)R$^{X2B}$, —SR$^{X2B}$, —SC(O)R$^{X2B}$, —SC(S)R$^{X2B}$, —C(O)OR$^{X2B}$, —C(O)NR$^{X2A}$R$^{X2B}$, —C(S)NR$^{X2A}$R$^{X2B}$, —NR$^{X2A}$R$^{X2B}$, —S(O)R$^{X2B}$, —S(O)$_2$R$^{X2B}$, —S(O)$_2$NR$^{X2A}$R$^{X2B}$, C$_{1-4}$ haloaliphatic, optionally substituted C$_{3-8}$ cycloaliphatic, C$_{1-6}$ aliphatic;

X$^4$ is N or C—R$^{B4}$, X$^5$ is N or C—R$^{B5}$, X$^6$ is N or C—R$^{B6}$, and X$^7$ is N or C—R$^{B7}$, where optionally up to two of X$^4$, X$^5$, X$^6$, and X$^7$ are N and each of R$^{B4}$, R$^{B5}$, R$^{B6}$, and R$^{B7}$ is, independently, hydrogen, halogen, —CN, —NO$_2$, —OR, —OC(O)R, —OC(O)OR, —OC(O)NRR', —OC(S)R, —SR, —SC(O)R, —SC(S)R, —C(O)OR, —C(O)NRR', —C(S)NRR', —NRR', —S(O)R, —S(O)$_2$R, —S(O)$_2$NRR', optionally substituted C$_{1-4}$ haloaliphatic, C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl;

each of R$^F$ and R$^G$ is, independently, hydrogen, optionally substituted C$_{1-6}$ aliphatic, C$_{1-4}$ haloaliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, 8- to 12-membered bicyclic heteroaryl, or when W is N(R$^F$), R$^F$ and R$^G$ and the intervening atoms together optionally form a N=C bond;

R$^H$ is hydrogen, optionally substituted C$_{1-6}$ aliphatic, C$_{1-4}$ haloaliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl;

$R^{X2A}$ is hydrogen, optionally substituted $C_{1-6}$ aliphatic, $C_{3-8}$ cycloaliphatic, $C_{6-10}$ aryl, 3- to 8-membered monocyclic heterocyclyl, 8- to 12-membered bicyclic heterocyclyl, 5- to 8-membered monocyclic heteroaryl, 8- to 12-membered bicyclic heteroaryl, —C(O)R, —C(O)NRR', —C(O)OR, —S(O)R, —S(O)$_2$R, or —S(O)$_2$NRR';

each of R, R', and $R^{X2B}$ is, independently, hydrogen, optionally substituted $C_{1-6}$ aliphatic, $C_{3-8}$ cycloaliphatic, $C_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl;

each of said heterocyclyl and heteroaryl rings contains one to four heteroatoms independently selected from oxygen, sulfur, or nitrogen;

the optional substituents on one or more carbon atoms of each of said aryl and heteroaryl groups are: halogen; —R°; —OR°; —SR°; 1,2-methylenedioxy; 1,2-ethylenedioxy; phenyl optionally substituted with R°; —O(Ph) optionally substituted with R°; —(CH$_2$)$_{1-2}$(Ph) optionally substituted with R°; —CH=CH(Ph) optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°C(O)OR°; —NR°NR°C(O)R°; —NR°NR°C(O)N(R°)$_2$; —NR°NR°C(O)OR°; —C(O)C(O)R°; —C(O)CH$_2$C(O)R°; —C(O)OR°; —C(O)R°; —C(S)R°; —C(O)N(R°)$_2$; —C(S)N(R°)$_2$; —B(OR°)$_2$; —OC(O)N(R°)$_2$; —OC(O)R°; —C(O)N(OR°)R°; —C(=NOR°)R°; —S(O)$_2$R°; —S(O)$_2$OR°; —S(O)$_2$N(R°)$_2$; —S(O)R°; —NR°S(O)$_2$N(R°)$_2$; —NR°S(O)$_2$R°; —N(OR°)R°; —C(=NH)—N(R°)$_2$; or —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$haloalkoxy, C$_{1-4}$ haloalkyl, -L-NO$_2$, -L-CN, -L-OH, -L-CF$_3$; or two substituents, on the same carbon or on different carbons, together with the carbon or intervening carbons to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)C(O)—, —C(O)—, —C(O)NH—, —C(O)NR°—, —C(=N—CN)—, —NHC(O)—, —NR°C(O)—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each occurrence of R° is independently selected from hydrogen, optionally substituted C$_{1-6}$ aliphatic, an unsubstituted 5- to 6-membered heteroaryl or heterocyclic ring, phenyl, or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3- to 8-membered cycloalkyl ring, wherein said heteroaryl or heterocyclyl ring has 1 to 3 heteroatoms independently selected from nitrogen, oxygen, or sulfur, wherein optional substituents on the aliphatic group of R° are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, C(O)O(C$_{1-4}$ aliphatic), O(haloC$_{1-4}$ aliphatic), or haloC$_{1-4}$ aliphatic, wherein each of the C$_{1-4}$ aliphatic groups of R° is unsubstituted; and the optional substituents on one or more carbon atoms of each of said aliphatic, haloaliphatic, cyclo aliphatic, and heterocyclyl groups are as defined for said aryl and heteroaryl groups and additionally comprise: =O, =S, =NNHR*, =NN(R*)$_2$, =NNHC(O)R*, =NNHC(O)O(alkyl), =NNHS(O)$_2$(alkyl), or =NR*, wherein each R* is independently selected from hydrogen or an optionally substituted C$_{1-6}$ aliphatic, and where optional substituents on said aliphatic group of R* are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo-C$_{1-4}$ aliphatic), and halo(C$_{1-4}$ aliphatic), wherein each of the foregoing C$_{1-4}$ aliphatic groups of R* is unsubstituted.

2. The compound according to claim 1, or a pharmaceutically acceptable salt thereof, having the formula:

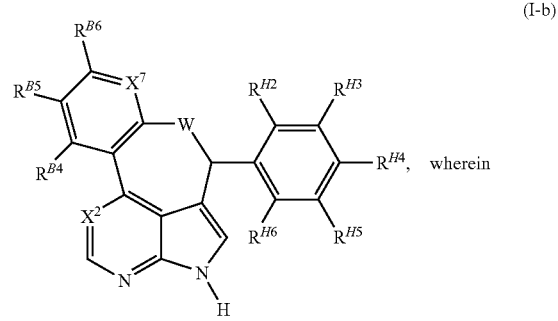

(I-b)

each of $R^{H2}$, $R^{H3}$, $R^{H4}$, $R^{H5}$, and $R^{H6}$ is, independently, hydrogen, halogen, —CN, —NO$_2$, —OR, —B(OR)$_2$, —OC(O)R, —OC(O)OR, —OC(S)R, —SR, —SC(O)R, —SC(S)R, —C(O)OR, —C(O)NRR', —C(S)NRR', —NRR', —S(O)R, —S(O)$_2$R, —S(O)$_2$NRR', optionally substituted C$_{1-4}$ haloaliphatic, C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl; and each of R and R' is, independently, hydrogen, optionally substituted C$_{1-6}$ aliphatic, C$_{3-8}$ cycloaliphatic, C$_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl.

3. The compound according to claim 2, wherein $R^{H4}$ is —OR, —B(OR)$_2$, —OC(O)R, —OC(O)OR, or —OC(S)R; each of $R^{B4}$, $R^{B5}$, and $R^{B6}$ is hydrogen; and $X^2$ is N or C—H.

4. The compound according to claim 3, wherein $R^{H4}$ is —OH.

5. The compound according to claim 1, wherein W is —N(R$^F$)—.

6. The compound according to claim 1, wherein at least one of $R^G$ or $R^H$ is not hydrogen.

7. The compound according to claim 6, wherein $R^H$ is an optionally substituted C$_{1-6}$ aliphatic, C$_{3-8}$ cycloaliphatic, C$_{6-10}$ aryl, 3- to 8-membered monocyclic heterocyclyl, or 5- to 8-membered monocyclic heteroaryl.

8. The compound according to claim 7, wherein $R^H$ is an optionally substituted $C_{6-10}$ aryl or 5- to 8-membered monocyclic heteroaryl.

9. The compound according to claim 8, or a pharmaceutically acceptable salt thereof, having the formula:

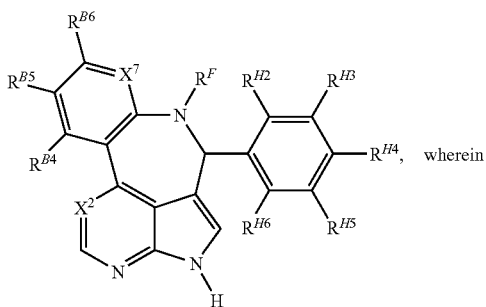
(II-d)

wherein $R^F$ is hydrogen, optionally substituted $C_{1-6}$ aliphatic, $C_{1-4}$haloaliphatic, $C_{3-8}$ cycloaliphatic, $C_{6-10}$ aryl, 3- to 8-membered monocyclic heterocyclyl, 8- to 12-membered bicyclic heterocyclyl, 5- to 8-membered monocyclic heteroaryl, 8- to 12-membered bicyclic heteroaryl;

each of $R^{H2}$, $R^{H3}$, $R^{H4}$, $R^{H5}$, and $R^{H6}$ is, independently, hydrogen, halogen, —CN, —NO$_2$, —OR, —B(OR)$_2$, —OC(O)R, —OC(O)OR, —OC(S)R, —SR, —SC(O)R, —SC(S)R, —C(O)OR, —C(O)NRR', —C(S)NRR', —NRR', —S(O)R, —S(O)$_2$R, —S(O)$_2$NRR', optionally substituted $C_{1-4}$ haloaliphatic, $C_{1-6}$ aliphatic, $C_{3-8}$ cycloaliphatic, $C_{6-10}$ aryl, 3- to 8-membered monocyclic heterocyclyl, 8- to 12-membered bicyclic heterocyclyl, or 5- to 8-membered monocyclic heteroaryl, 8- to 12-membered bicyclic heteroaryl; and each of R and R' is, independently, hydrogen, optionally substituted $C_{1-6}$ aliphatic, $C_{3-8}$ cycloaliphatic, $C_{6-10}$ aryl, 3- to 8-membered monocyclic heterocyclyl, 8- to 12-membered bicyclic heterocyclyl, 5- to 8-membered monocyclic heteroaryl, or 8- to 12-membered bicyclic heteroaryl.

10. The compound according to claim 9, wherein $R^{H4}$ is —OR, —B(OR)$_2$, —OC(O)R, —OC(O)OR, or —OC(S)R; each of $R^{B4}$, $R^{B5}$, and $R^{B6}$ is hydrogen; and $X^2$ is N or C—H.

11. The compound according to claim 10, wherein $R^{H4}$ is —OH.

12. The compound according to claim 8, or a pharmaceutically acceptable salt thereof, having the formula

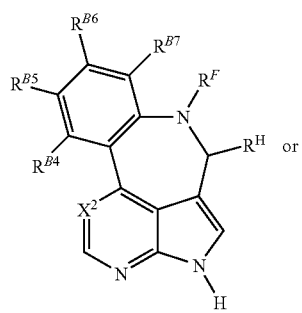
(II-f)

or

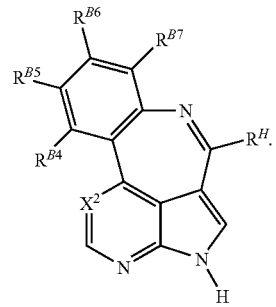
(II-g)

13. The compound according to claim 12, wherein each of $R^{B4}$, $R^{B5}$, $R^{B6}$, and $R^{B7}$ is hydrogen.

14. The compound according to claim 1, wherein each of $R^{B4}$, $R^{B5}$, and $R^{B6}$ is hydrogen; $X^7$ is N or C—H; $X^2$ is N or C—H; and each of $R^{H2}$, $R^{H3}$, $R^{H5}$, and $R^{H6}$ is, independently, hydrogen, halogen, —CN, —NO$_2$, —OR, —B(OR)$_2$, —OC(O)R, —OC(O)OR, —C(O)OR, —C(O)NRR', —C(S)NRR', —NRR', —S(O)$_2$R, —S(O)$_2$NRR', optionally substituted $C_{1-4}$ haloaliphatic, $C_{1-6}$ aliphatic, $C_{3-8}$ cycloaliphatic, wherein each of R and R' is, independently, hydrogen or optionally substituted $C_{1-6}$ aliphatic.

15. A compound selected from the following group of compounds:

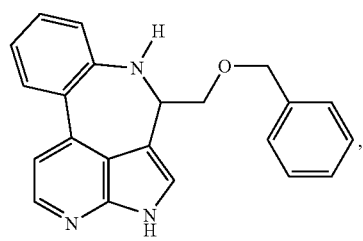
1

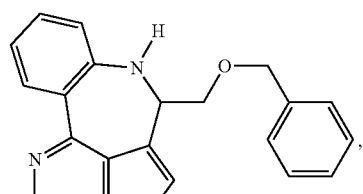
2

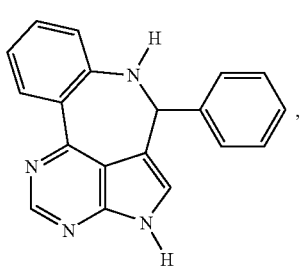
3

-continued
4
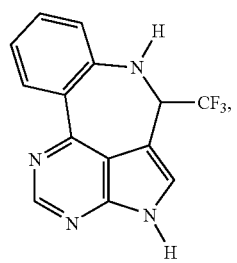
5
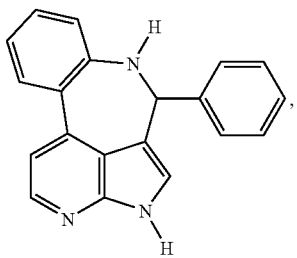
6
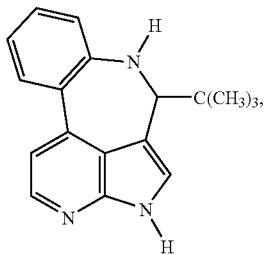
7
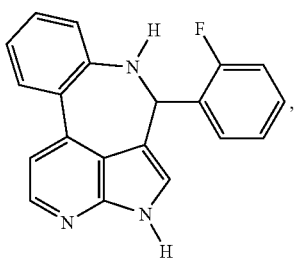
8
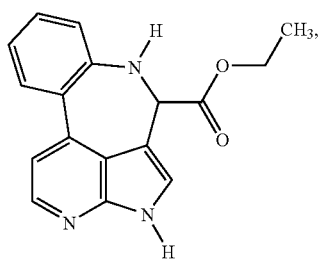
9
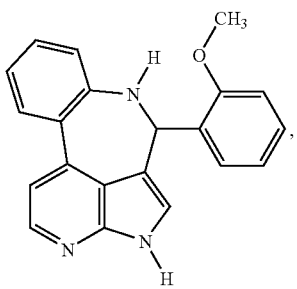
-continued
10
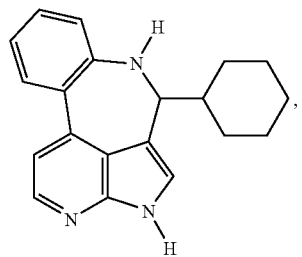
11
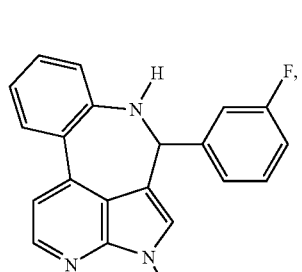
12
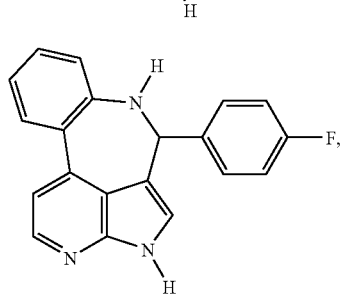
13
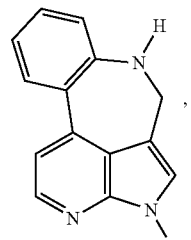
14
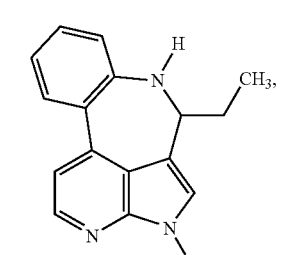
15
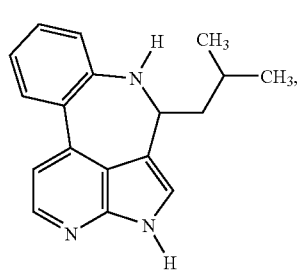

16 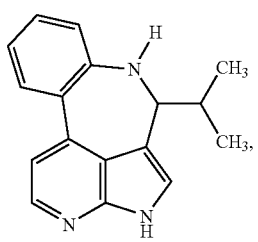
17 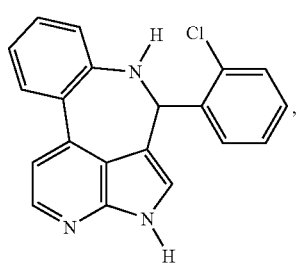
18 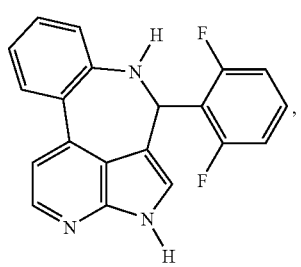
19 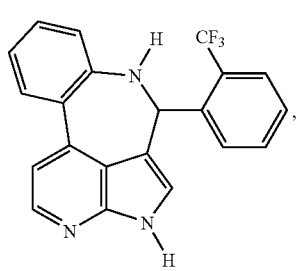
20 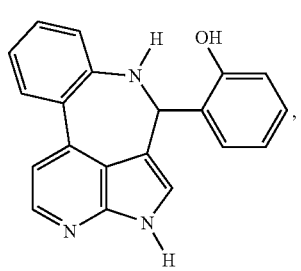
21 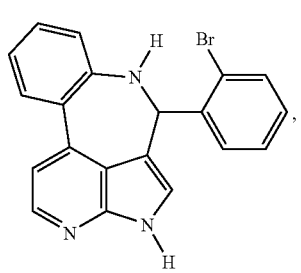
22 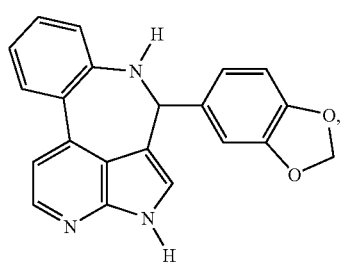
23 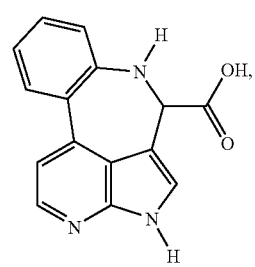
24 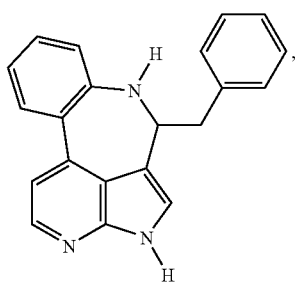
25 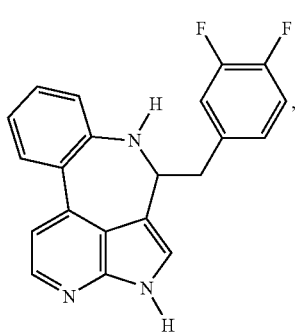
26 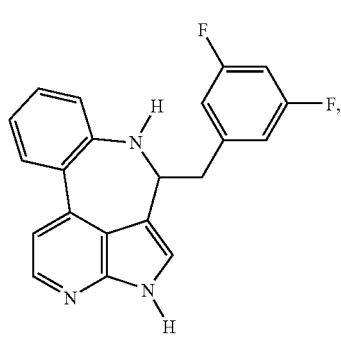

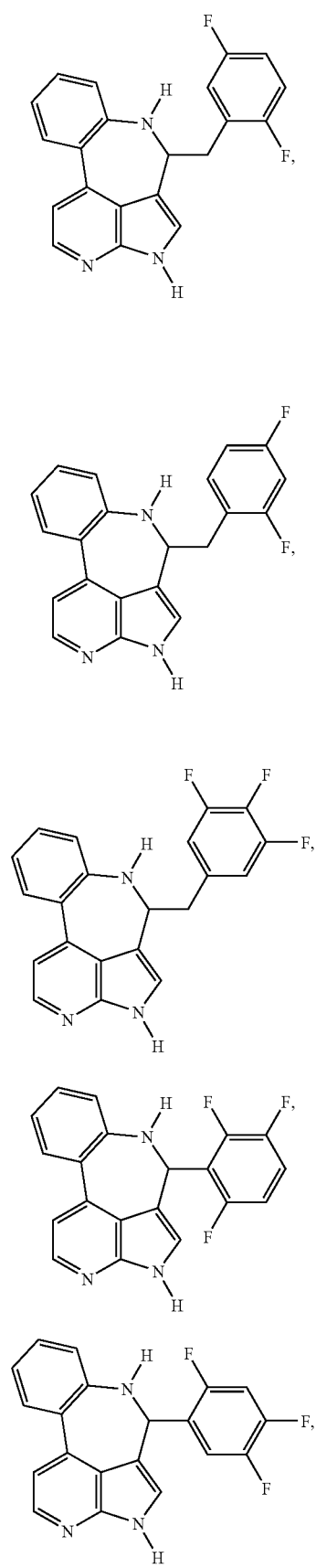
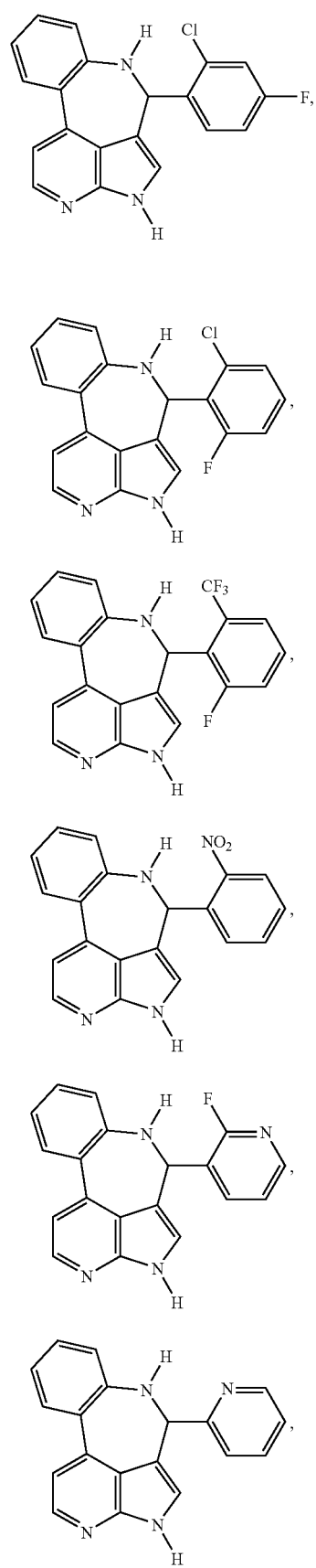

38 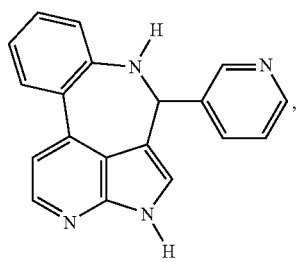
39 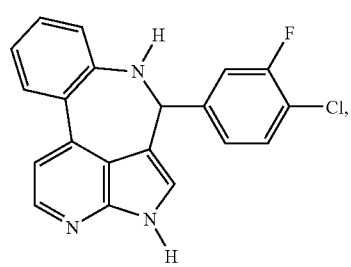
40 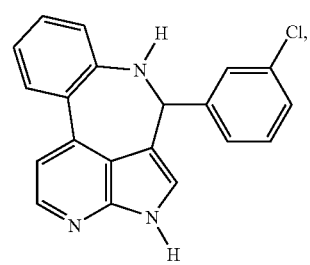
41 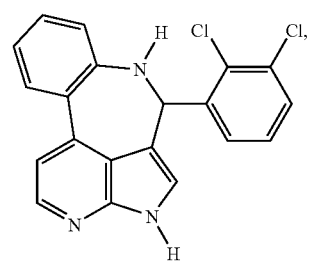
42 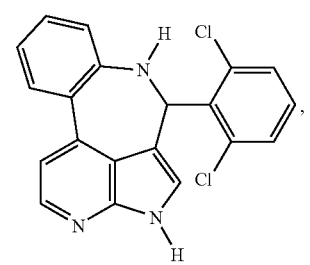
43 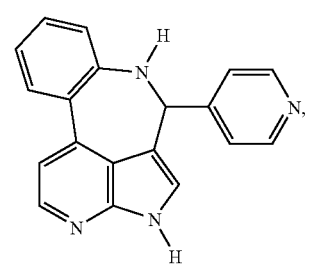
44 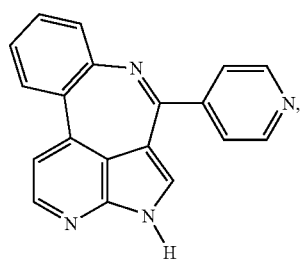
45 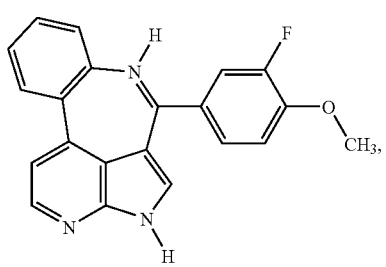
46 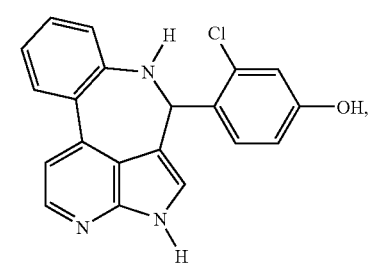
47 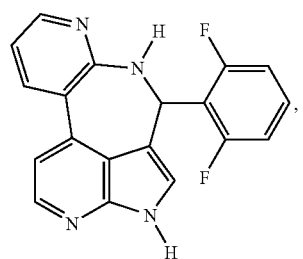
48 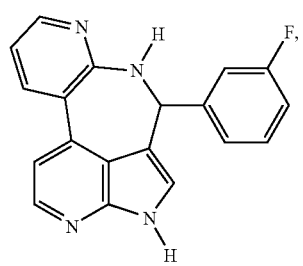
49 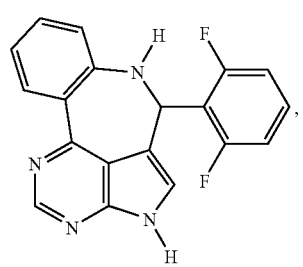

-continued
50
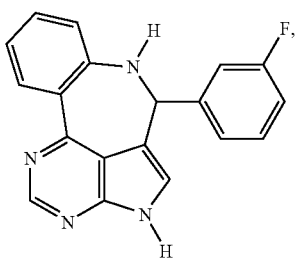
51
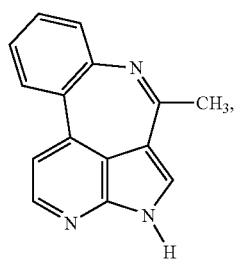
52
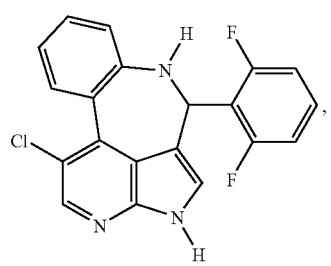
53
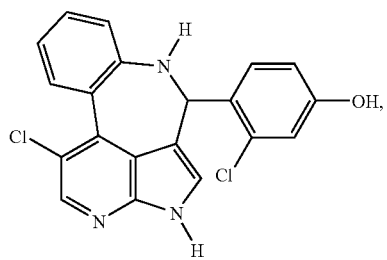
54
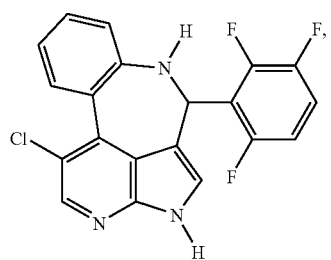
55
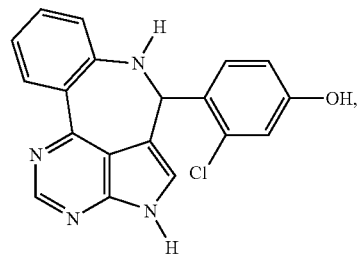
-continued
56
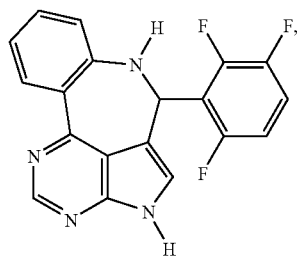
57
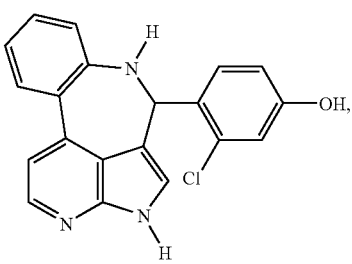
58
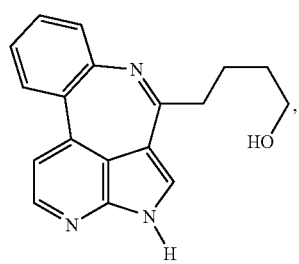
59
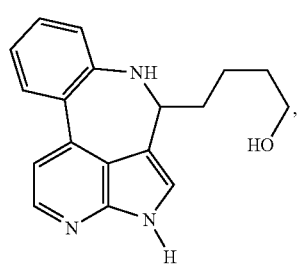
60
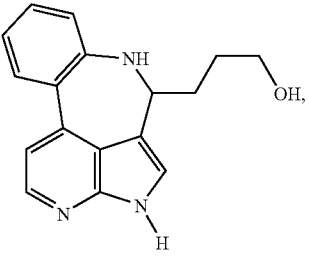
61
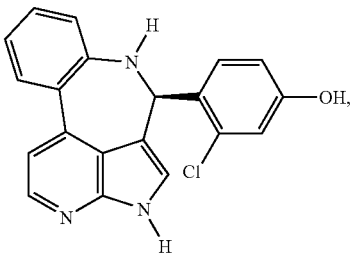

101
-continued
62
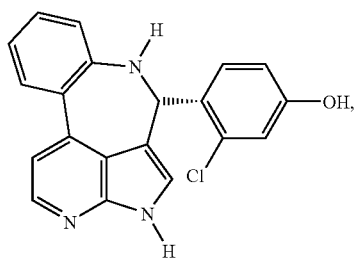
63
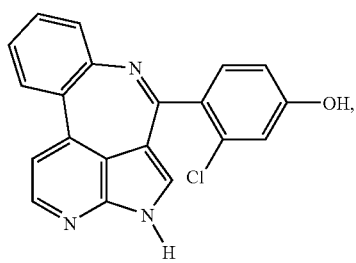
64
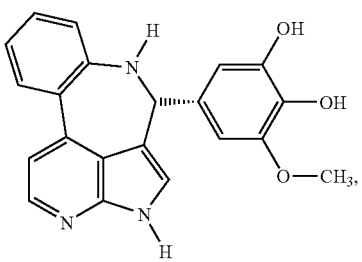
65
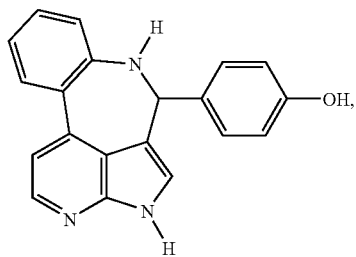
66
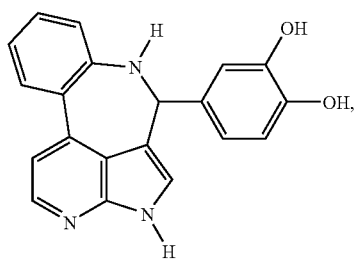
67
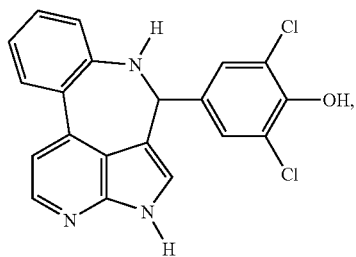
102
-continued
68
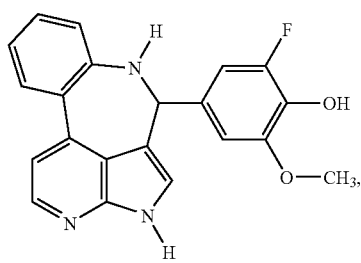
69
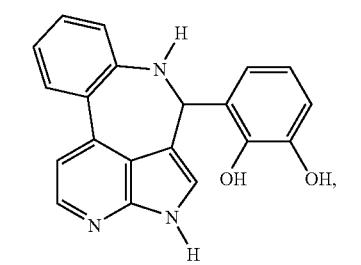
70
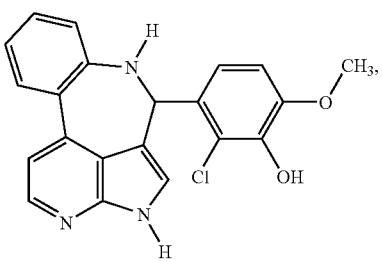
71
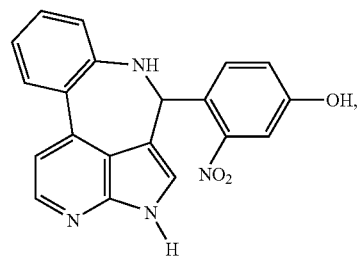
72
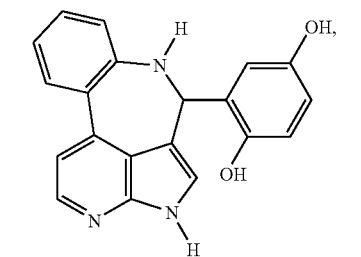
73
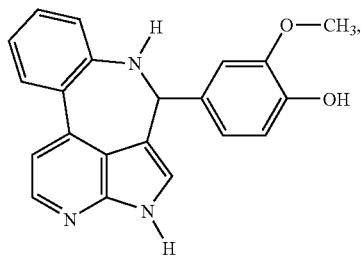

| 74 | 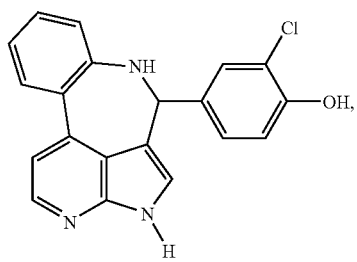 | 80 | 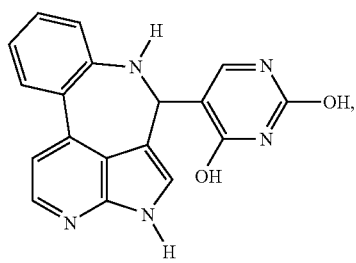 |
| 75 | 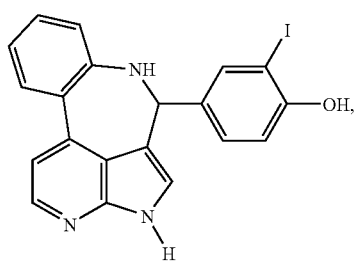 | 81 | 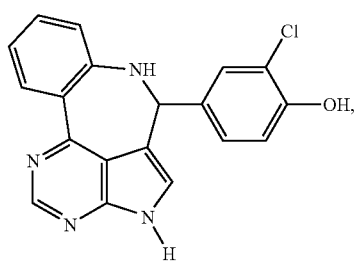 |
| 76 | 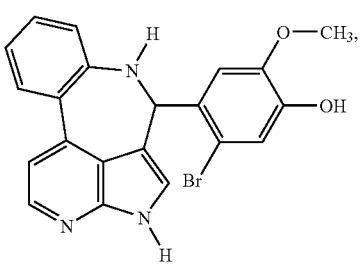 | 82 | 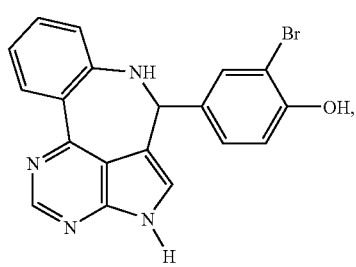 |
| 77 | 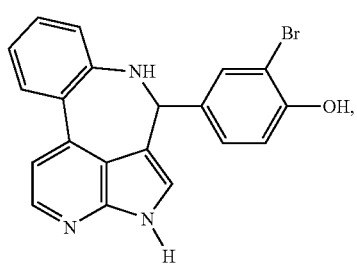 | 83 | 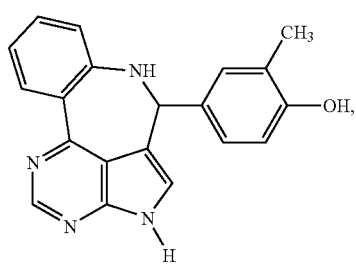 |
| 78 | 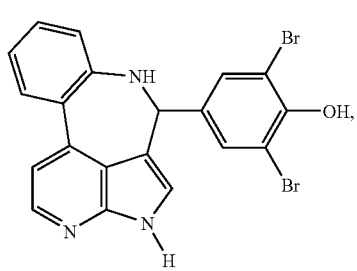 | 84 | 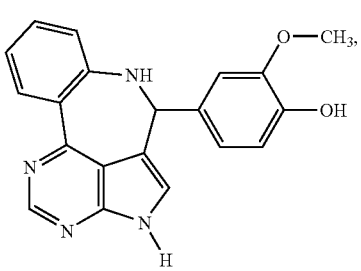 |
| 79 | 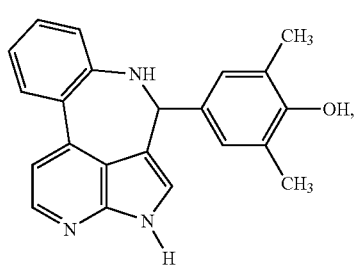 | 85 | 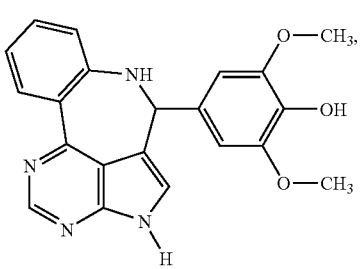 |

| 105 | 106 |
|---|---|
| -continued | -continued |
86
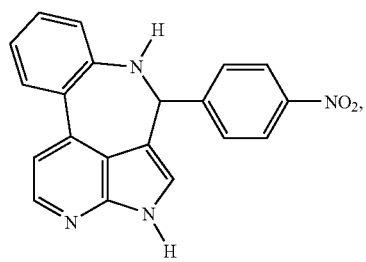
92
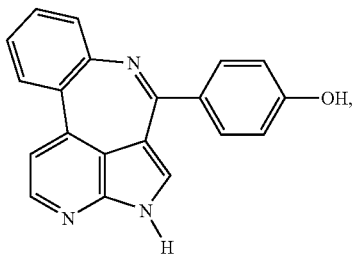
87
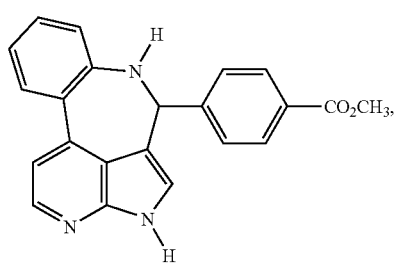
93
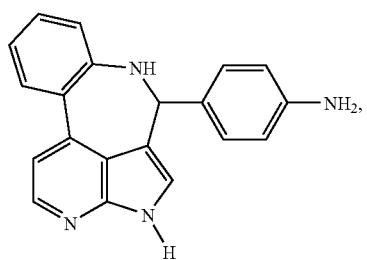
88
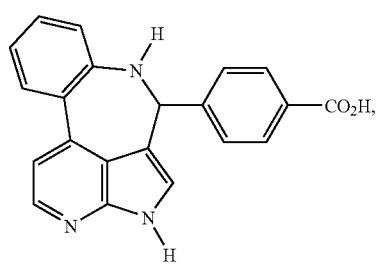
94
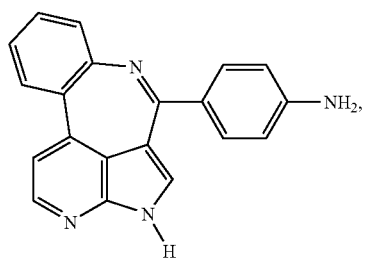
89
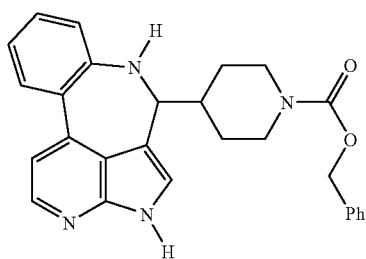
95
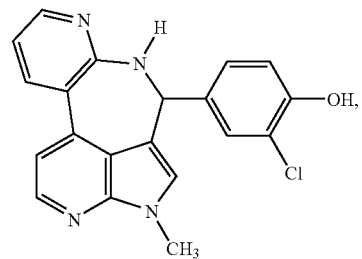
90
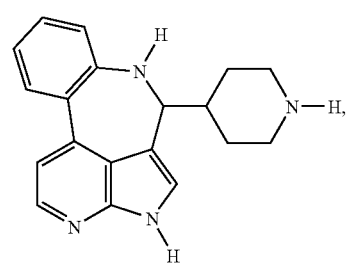
96
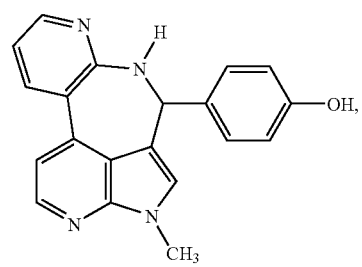
91
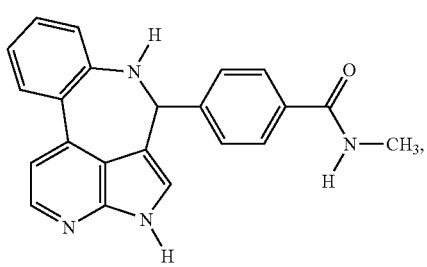
97
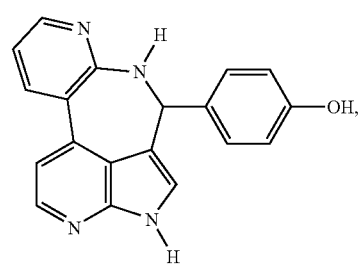

107
-continued
98
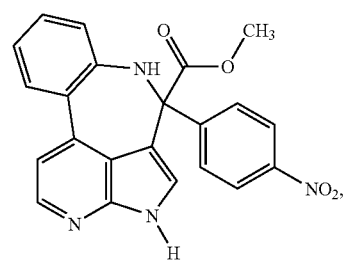
99
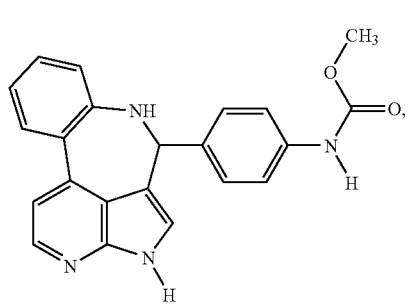
100
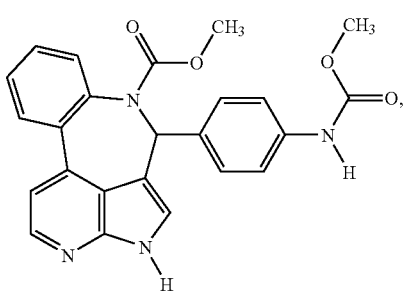
101
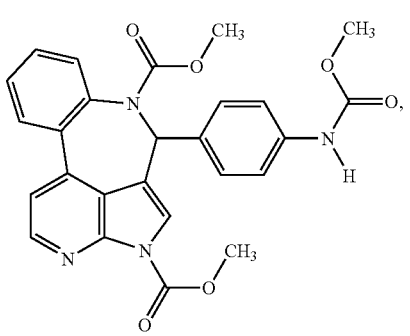
102
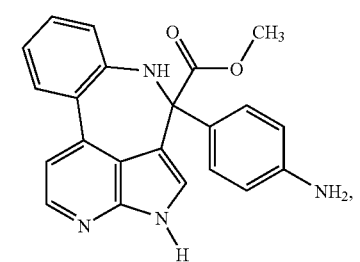
108
-continued
103
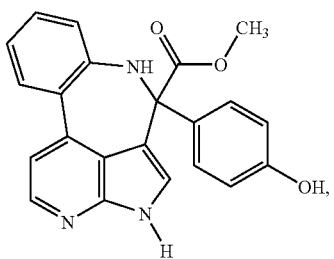
104
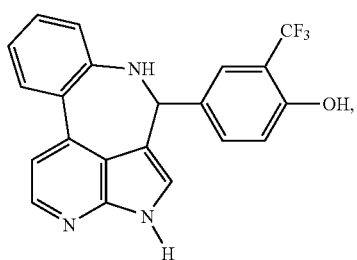
105
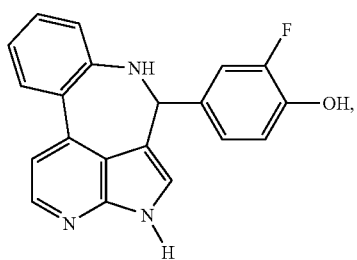
106
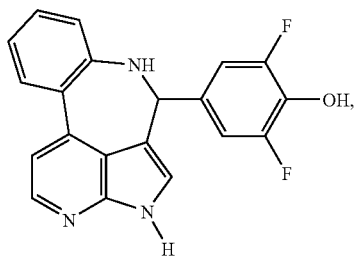
107
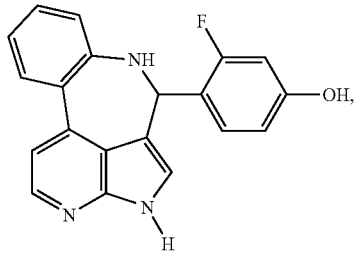
108
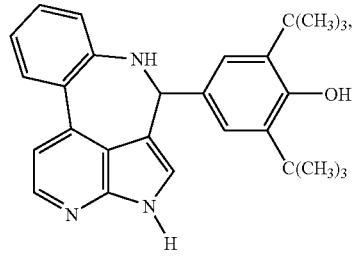

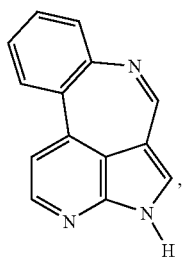
109
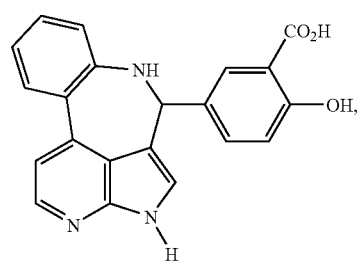
110
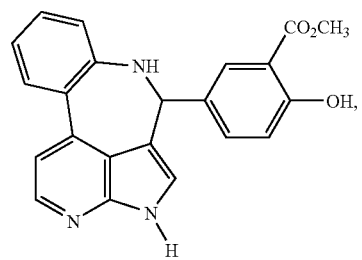
111
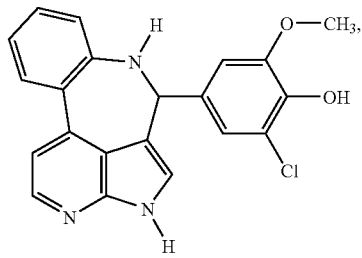
112
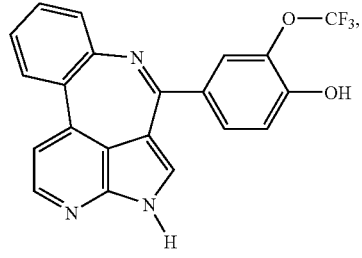
113
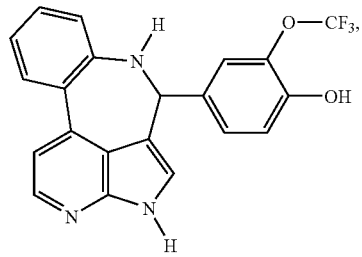
114
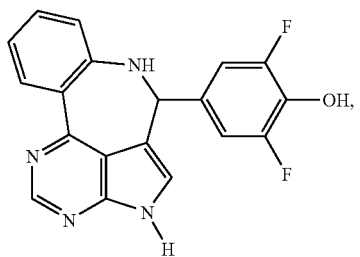
115
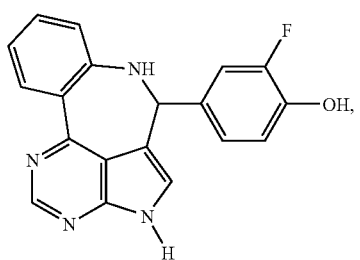
116
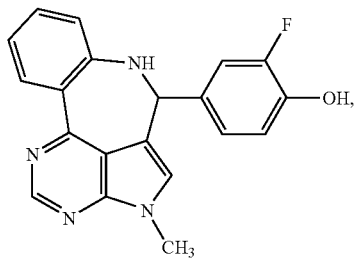
117
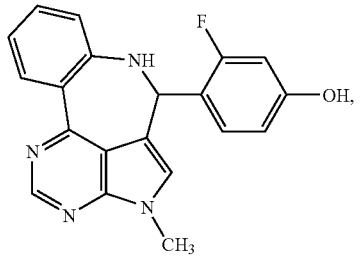
118
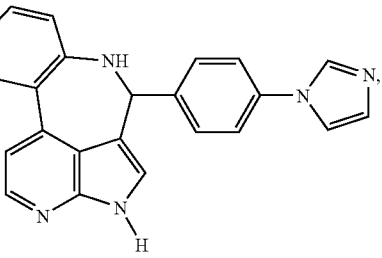
119
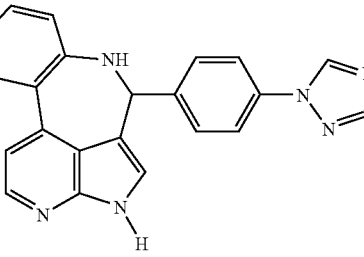
120

121
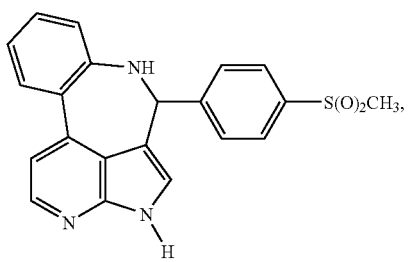
122
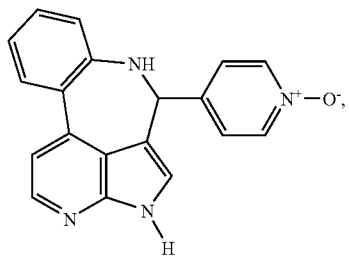
123
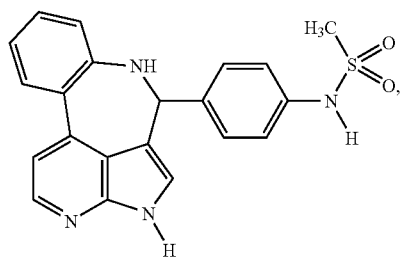
124
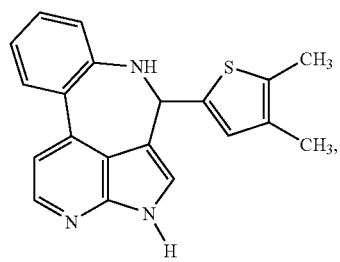
125
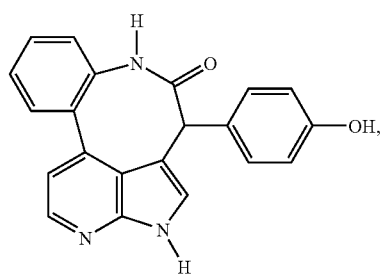
126
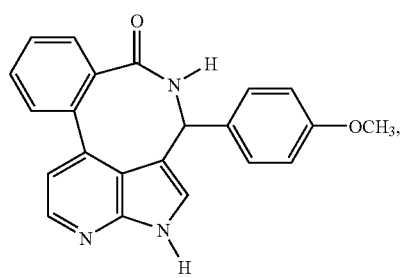
127
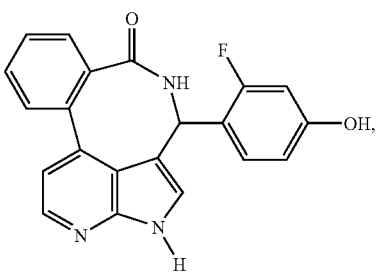
128
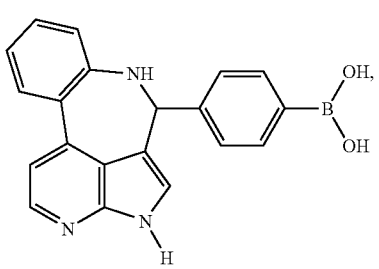
129
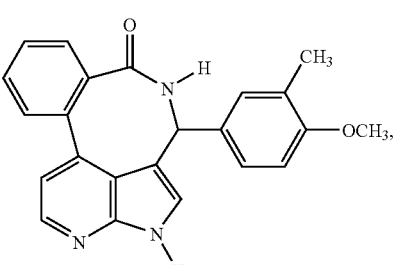
130
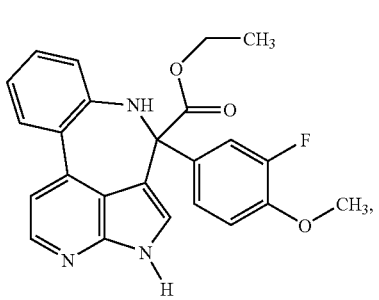
131
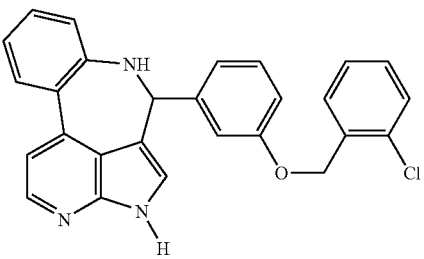
132
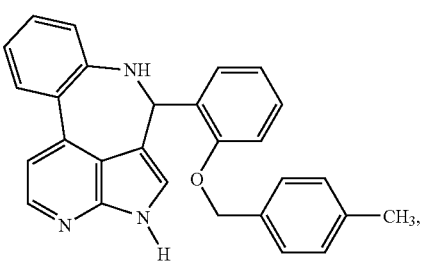

133 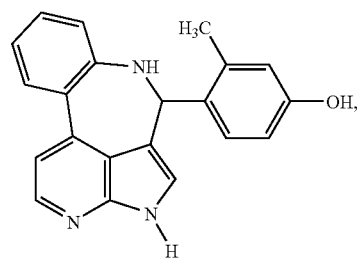
134 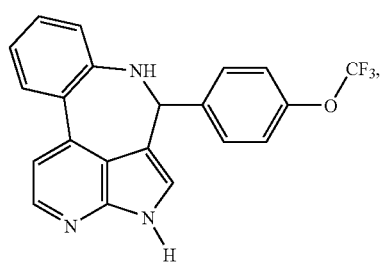
135 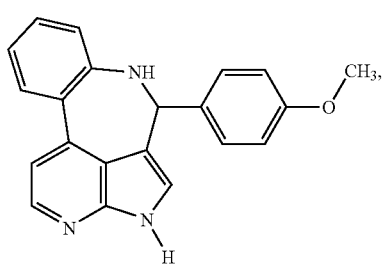
136 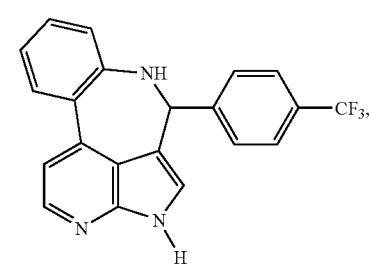
137 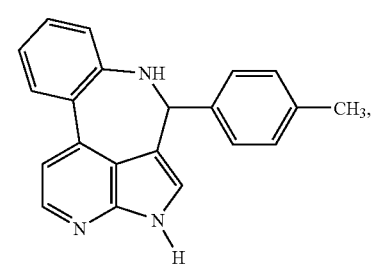
138 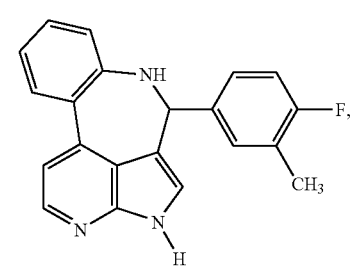
139 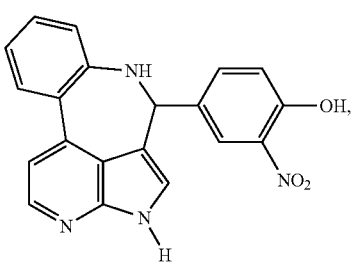
140 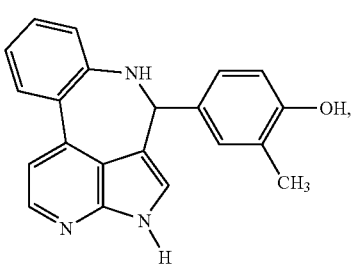
141 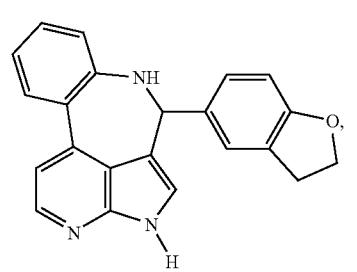
142 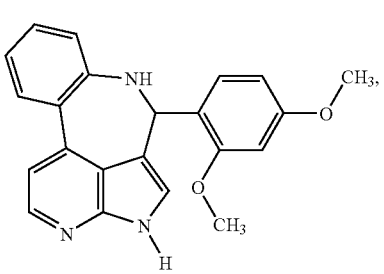
143 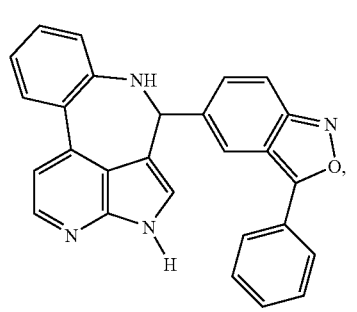
144 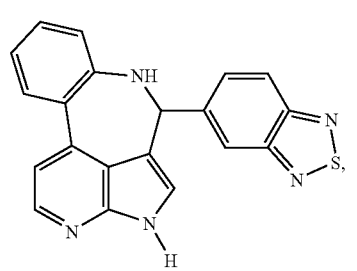

145 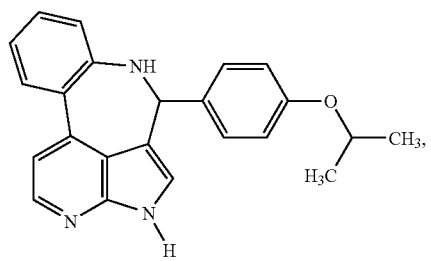
146 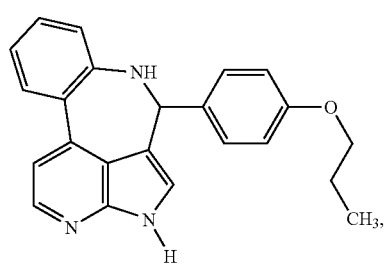
147 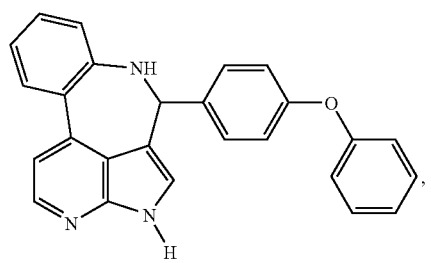
148 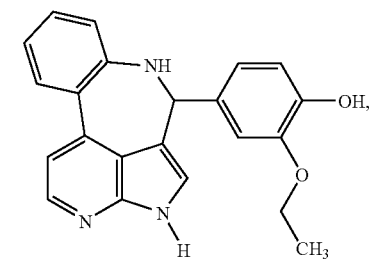
149 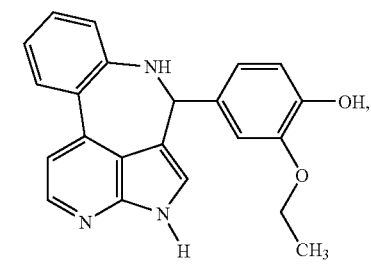
150 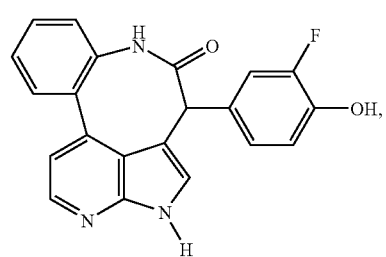
151 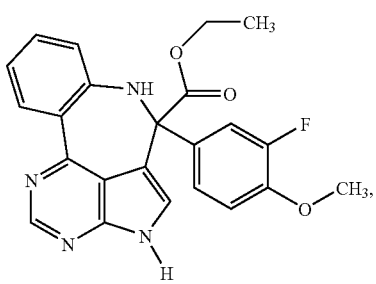
152 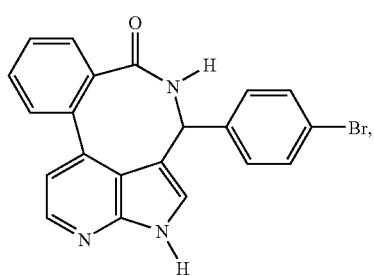
153 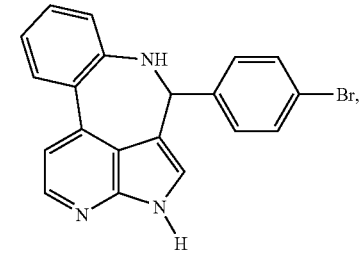
154 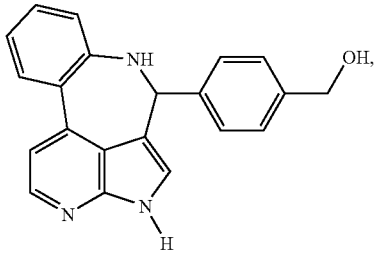
155 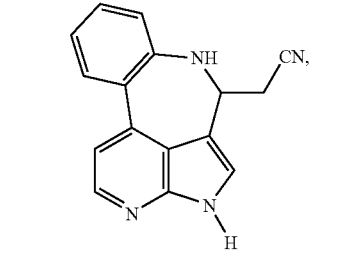
156 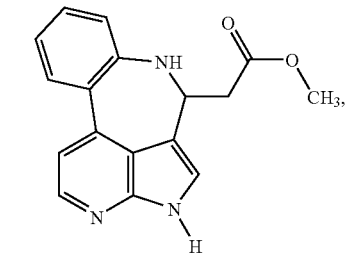

157 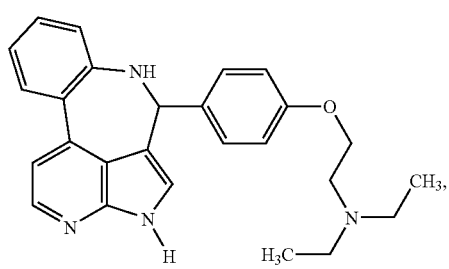
158 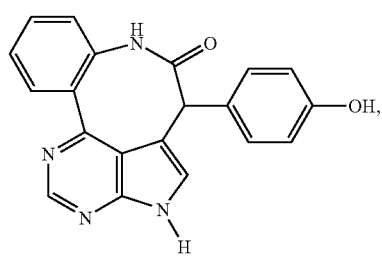
159 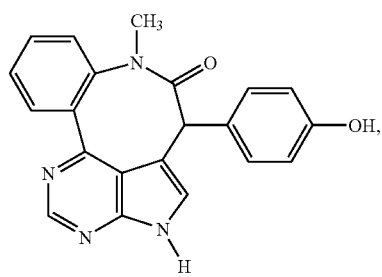
160 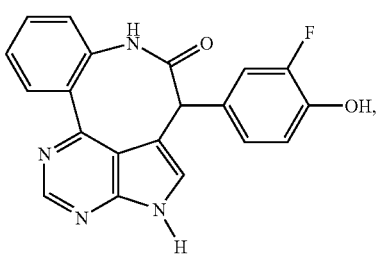
161 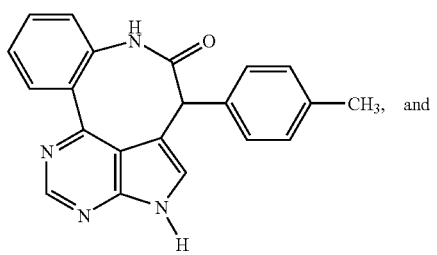
162 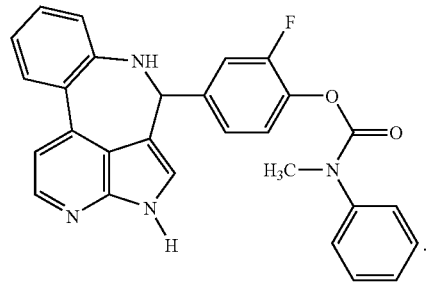
16. A pharmaceutical composition comprising a compound according to any one of claims 1-13 and a pharmaceutically acceptable carrier, adjuvant, or vehicle.
* * * * *